United States Patent [19]

Mitchell et al.

[11] Patent Number: 4,713,347

[45] Date of Patent: Dec. 15, 1987

[54] MEASUREMENT OF LIGAND/ANTI-LIGAND INTERACTIONS USING BULK CONDUCTANCE

[75] Inventors: David H. Mitchell; Ralph M. Mitchell, both of Pacific Palisades, Calif.

[73] Assignee: Sensor Diagnostics, Inc., Irvine, Calif.

[21] Appl. No.: 691,271

[22] Filed: Jan. 14, 1985

[51] Int. Cl.$^4$ .................. G01N 33/566; G01N 27/26; G01N 27/02; G01N 33/544

[52] U.S. Cl. .................................... 436/501; 204/403; 324/439; 324/61 P; 935/78; 435/6; 435/311; 435/291; 436/149; 436/527; 436/530; 436/533; 436/806; 436/807; 422/68

[58] Field of Search ............. 204/403; 324/439, 61 P; 422/68, 69; 435/173, 291, 311, 807, 6; 436/149, 150, 501, 536, 806, 807, 829, 530, 533

[56] References Cited

U.S. PATENT DOCUMENTS

| | | |
|---|---|---|
| 3,555,143 | 1/1971 | Axen et al. . |
| 3,646,346 | 2/1972 | Catt . |
| 3,654,090 | 4/1972 | Schuurs et al. . |
| 3,791,932 | 2/1974 | Schuurs et al. . |
| 3,850,752 | 11/1974 | Schuurs et al. . |
| 3,939,408 | 2/1976 | Brown . |
| 3,963,979 | 6/1976 | Dauphinee . |
| 3,975,238 | 8/1976 | Bean et al. . |
| 4,053,646 | 10/1977 | Wright et al. . |
| 4,054,646 | 10/1977 | Giaever . |
| 4,081,334 | 3/1978 | Suzuki et al. . |
| 4,092,408 | 5/1978 | Litt . |
| 4,151,049 | 4/1979 | Janata . |
| 4,191,739 | 3/1980 | Uzgiris et al. . |
| 4,219,335 | 8/1980 | Ebersole . |
| 4,233,144 | 11/1980 | Pace et al. . |
| 4,236,893 | 12/1980 | Rice . |
| 4,238,757 | 12/1980 | Schenck . |
| 4,242,096 | 12/1980 | Oliveira et al. . |
| 4,321,057 | 3/1982 | Buckles . |
| 4,334,880 | 6/1982 | Malmros . |
| 4,350,660 | 9/1982 | Robinson et al. ..................... 422/90 |
| 4,376,110 | 3/1983 | David et al. . |
| 4,402,819 | 9/1983 | Rechnitz et al. ................. 204/403 X |
| 4,444,892 | 4/1984 | Malmros ......................... 436/531 X |
| 4,452,773 | 6/1984 | Molday ........................... 436/530 X |
| 4,473,456 | 9/1984 | Hawkins ......................... 324/439 X |
| 4,554,257 | 11/1985 | Aladjem et al. ................. 436/517 X |
| 4,562,157 | 12/1985 | Lowe et al. ..................... 436/806 X |
| 4,571,543 | 2/1986 | Raymond et al. .............. 436/178 X |
| 4,652,830 | 3/1987 | Brown ................................ 324/439 |

FOREIGN PATENT DOCUMENTS

WO84/03945 3/1983 PCT Int'l Appl. .

OTHER PUBLICATIONS

Brown, N. L. et al, *Deep-Sea Research*, vol. 8, 1961, pp. 65-75.
Jay, F. et al, *IEEE Standard Dictionary of Electrical and Electronics Terms*, Wiley-Interscience, N.Y., 1984, p. 402.
Analytical Chem. 56, 801 (1984).
Chem. & Eng. News, Apr. 2, 1984, p. 32.
Introduction to Bioinstrumentation, C. D. Ferris, 1978, pp. 109-116.
IEEE Journal on Ocean Engineering, vol. OE-4, No. 3, Pederson & Greg, 1979.

*Primary Examiner*—Esther M. Kepplinger
*Assistant Examiner*—Jeremy M. Jay
*Attorney, Agent, or Firm*—Gregory D. Williams; David G. Conlin

[57] ABSTRACT

Methods, apparatus and sensors are described for detection of specific ligands in a fluid sample by measuring ligand-specific changes in the bulk electrical conductance (or resistance) of a fixed test volume, with antiligand or ligand localized in or near that volume.

85 Claims, 41 Drawing Figures

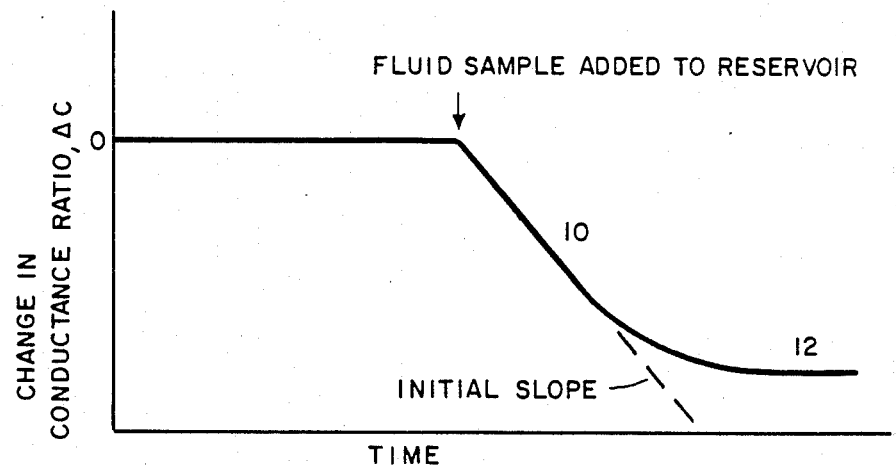
FIG. IA
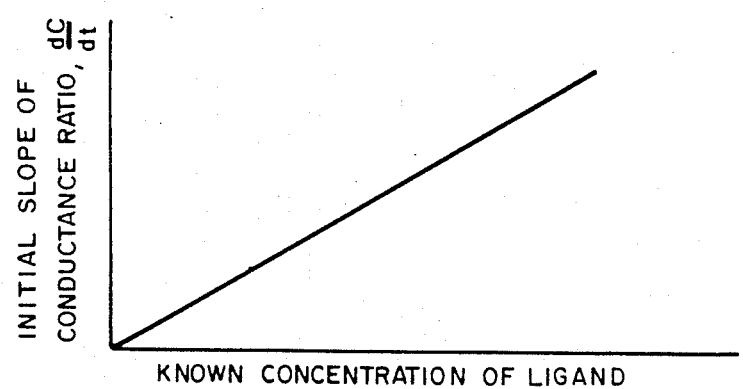
FIG. IB

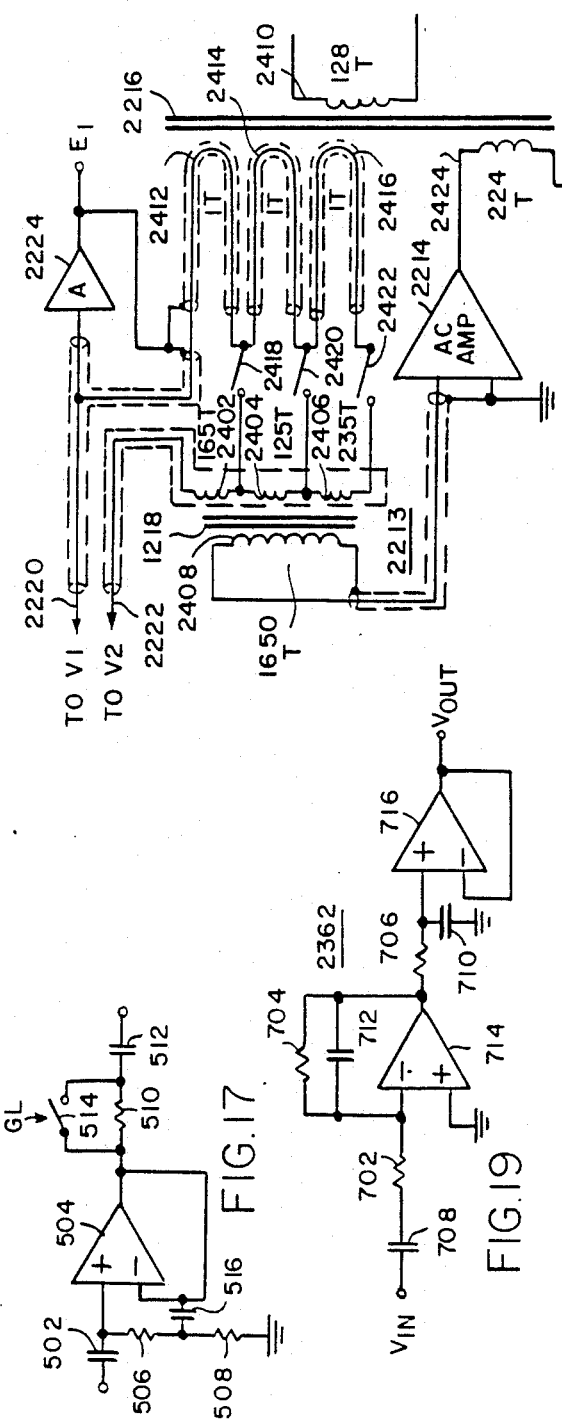

MEASUREMENT OF LIGAND/ANTI-LIGAND INTERACTIONS USING BULK CONDUCTANCE

BACKGROUND OF THE INVENTION

This invention relates to analytical methods and apparatus, more particularly to methods, apparatus and sensors for detection of a substance of interest in a fluid sample.

There are many types of standard tests or assays for detection of the presence and/or concentration of specific substances in fluids. Until recently many of these assays required development of different reagents and protocols for each substance to be detected. Examples of these approaches include various enzyme assay protocols in biochemistry laboratories and the Technicon SMAC machines, duPont Automated Clinical Analyzer, and Kodak Ektachem 700 machines in clinical chemistry laboratories.

In the last two decades a new type of diagnostic test or assay has gained increasing use—the antibody-based assay, or immunoassay. In immunoassays, an antibody may be used, for example, to probe for the presence of a particular antigen, hapten, or other molecule. Immunoassays have several potential advantages over previous assays:

(a) they are procedurally generalizable; that is, the same type of assay procedures and reagents can be used to detect most antigens no matter what the chemical properties of a particular antigen are.

(b) they are highly specific; that is, they can potentially distinguish well between structurally related compounds.

(c) they are potentially very sensitive.

Immunoassays are a specific type of a more general assay strategy, the ligand/antiligand assay. All ligand-/antiligand assays are based on two premises: (1) that certain pairs of substances (the ligand and the antiligand) have a strong and specific affinity for each other, that is, they will tend to bind to each other, while binding little or not at all to other substances; and (2) that methods and apparatus can be developed that allow detection of ligand/antiligand binding interactions once complexes have formed. As used herein, ligand is defined as the substance to be detected, and antiligand the substance used to probe for the presence of the ligand. (In some ligand/antiligand assays, an additional, perhaps modified, ligand may be used that competes with the substance to be detected for binding sites on the antiligand.)

In many cases, detection of a ligand/antiligand complex is made possible by labelling one component of the complex in some way, to make the entire complex "visible" to an appropriate detecting instrument. For example, radioimmunoassay (RIA) uses a radioisotope as a label. See U.S. Pat. Nos. 3,555,143 and 3,646,346. Enzyme immunoassays (EIA) use an enzyme that can produce a detectable color under appropriate conditions. See U.S. Pat. Nos. 3,654,090, 3,791,932 and 3,850,752. Similarly, fluorescence immunoassays (FIA) use a fluorescent label.

Yet another ligand/antiligand assay that is becoming increasingly important is the nucleic acid hybridization assay, e.g., the DNA probe assay, which uses a "probe" strand of nucleic acid as an antiligand to test for the presence of a complementary DNA sequence. DNA probe assays, like immunoassays, often use radioactive labels, fluorescent labels or enzyme labels.

Recently, other ligand/antiligand assay techniques have been developed that use less standard tags. For example, particle counting immunoassay uses small latex spheres which scatter light in known ways when the spheres agglutinate due to antigen-antibody interaction. Both immunoassays and DNA probe assays have used luminescent labels as well.

Labels can greatly increase the sensitivity of ligand-/antiligand assays by associating the presence of the labelled complex with a detectable signal. However, label-using assays also often have associated disadvantages. First of all, the labelled immunoreagents must be prepared, which may require time and expense. Also, several processing steps may be necessary during the assay, such as addition of label, incubation to allow reaction between components, washing away of excess label, transfer to a detecting instrument, and detection of the labelled complex. Because of their relative complexity, many of these assays may consume considerable time and require skilled technical help. Such assays also may be relatively hard to automate, except by means of expensive equipment. Further, these assays generally monitor the level of only one ligand at a time. Further still the labelled reagents may be unstable, inconvenient, or dangerous to handle, as with the isotopes $I^{125}$ or $p^{32}$ and carcinogenic enzyme substrates. Also, using the above and other currently available label-dependent assays, it is not possible to monitor the level of antigen continuously; thus in order to follow the level of an antigen or antibody over an extended time, samples must be withdrawn at intervals, treated with label, and tested.

A number of techniques are in commercial use or under development that seek to avoid some of the problems noted above by avoiding the use of labels or by modifying how lables are used. Many such techniques probe for the formation of ligand/antiligand complexes by optical means. For example, rate nephelometry, a type of immunoassay, measures changes in the angular distribution of scattered light as antigens and antibodies form aggregates under certain conditions. This method is not very sensitive, however, and requires testing of two dilutions of the sample.

Pregnancy testing, syphilis testing, and blood antigen testing, among others, are often done by visual inspection for formation of precipitated or agglutinated antigen/antibody complexes. Strictly speaking, however, the cells or particles often used in these tests to make aggregation visible could be called labels. In any case they have some of the disadvantages associated with labels noted above, such as the lack of potential for continuous measurement or for making simultaneous determinations of multiple ligands in the same sample. A number of other immunoassay systems use some form of optical detection without relying on precipitin formation, agglutination or standard labels. See U.S. Pat. Nos. 3,975,238, 4,054,646 and 4,321,057.

There are also several types of immunoassays based on electrical detection of ligand/antiligand complexes. These assays focus on overcoming one or more of the disadvantages noted above. One such method is the resistive pulse technique taught by U.S. Pat. No. 4,191,739, which makes a bulk conductance measurement. This technique is a modification of the Coulter counter approach, whereby a conducting fluid containing nonconducting particles is passed through a narrow constricted channel, whose overall (bulk) resistance is measured. The overall resistance increases whenever a nonconducting particle traverses the channel, and the size of the "pulse" produced is proportional to the particle's volume. Thus, if particles coated with antibody, for example, are exposed to antigen under appropriate conditions, they will aggregate, and the increased size and number of the aggregates can be related to the amount of antigen present. However, the sensitivity of this technique is limited by the presence of self-aggregates that form during the manufacture of the antibody-coated particles themselves. U.S. Pat. No. 4,191,739 seeks to eliminate this problem and hence increases the sensitivity of this technique by coating two particle preparations of different sizes with antibody, and counting only aggregates containing both large and small particles as indicative of the presence of antigen. However, the technique, as disclosed, requires an expensive apparatus. Also, it requires a label (the particles to which antibody or other antiligand is attached), and it cannot easily be adapted to measure multiple ligands at the same time in a single sample fluid, nor to measure a continuously varying sample.

U.S. Pat. Nos. 4,236,893 and 4,242,096 relate to the use of a piezoelectric oscillator that has been coated with antigen to detect the presence of antigen or antibody in a fluid sample. More specifically, there is a change in the frequency of the oscillator as its mass changes due to binding of antibody to the antigen on its surface. Although this assay does not require labelled reagents or sophisticated instrumentation, as disclosed it requires a complex protocol including removing the sensor from solution after exposure to the fluid sample and drying it before measurements can be made.

U.S. Pat. No. 4,0543,646 relates to the use of capacitance as one of several ways to measure the relative thickness of an antigen/antibody bimolecular layer. In particular, conducting substrate is exposed to an antigen, antibody, or other antiligand, whereby a monomolecular layer of antiligand forms on the conducting surface that will in general be an electrical insulator when dry. This surface is then exposed to a solution containing the ligand of interest, a layer of which is also an insulator when dry. Finally, a mercury drop or other electrode is contacted with the dry ligand layer. The conducting substrate and the mercury drop comprise the two conducting plates of a capacitor separated by an insulating layer whose thickness depends on the amount of ligand that has bound to the antiligand. The capacitance of this capacitor is then measured by means of a suitable instrument. This technique does not require labelled immunoreagents or expensive instrumentation. However, like the piezoelectric assay above, it requires that the ligand-containing capacitor be removed from solution and dried before measurements can be made.

Other types of electrical assays have sought to simplify ligand/antiligand assay procedures by measuring changes in electrical properties associated with a surface or interface in contact with an electrolyte. For example, when a surface such as a metal electrode is exposed to an electrolyte solution, strong local gradients of electrical charge and potential arise in the region of the electrode/electrolyte interface. Because the gradients and associated electrical potentials are strong, ligand molecules that interact with an immunoreagent or other antiligand immobilized at the interface can have a considerable effect on the overall electrical properties at the interface and thus can generate strong electrical signals of various kinds. Examples of assays based on the above phenomena include voltammetric assay as taught in U.S. Pat. No. 4,233,144; field effect transistor-based assays and other semiconductor-based assays as taught in U.S. Pat. Nos. 4,238,757 and 4,334,880; electrical reactance assays as taught in U.S. Pat. No. 4,219,335; antibody electrode assays (Analytical Chem. 56,801 (1984); Chem. & Eng. News, Apr. 2, 1984, p. 32) and other potentiometric assays, e.g., as taught in U.S. Pat. Nos. 4,151,049 and 4,081,334.

Such interface-based assays can be fast, simple to perform, and continuous, since a sample can be monitored as long as it is in contact with the interface. Such assays can also be label-independent and can be adapted to monitor multiple analytes simultaneously. However, interface electrical properties can be affected in many non-specific ways, such as by variations in pH or electrolyte composition or by non-specific adsorption of species in solution onto, or into, the surface or interface. Thus, methods based on measurement of such properties are often subject to interferences that are unpredictable or hard to control. Further, many of these methods require preparation of a membrane or molecular layer at or on the interface that contains ligand or antiligand, and this can be hard to do reproducibly.

It would therefore be advantageous to have a ligand-/antiligand assay system which retains the advantages while overcoming the disadvantages associated with the above-described assays. More specifically, it would be advantageous to have an economical assay which is quick (can be completed in less than a minute), capable of being continuous, capable of detecting the presence of multiple ligands simultaneously in a fluid sample, simple to perform and label-independent. It would also be advantageous to have an apparatus which enables such an assay to be performed and which is miniaturizable in the sense that it allows measurement of ligand/antiligand interaction in an extremely small volume.

SUMMARY

In accordance with the present invention, there are provided methods, apparatus and sensors for determining the presence of a ligand in a fluid sample by measuring changes in the bulk electrical conductance of a test volume. The conductance changes are made ligand-specific by the presence in or near the test volume of a predetermined region containing localized antiligand or ligand. This predetermined region is exposed to the fluid sample, ligand/antiligand interaction occurs, and the resulting conductance changes are monitored by any suitable conductance-measuring instrument.

This invention also relates to methods and apparatus for eliminating non-specific noise and drift by (i) comparing the bulk conductance of a test volume with nearby negative or positive control volumes, and/or (ii) minimizing effects of phenomena occurring at electrode/electrolyte interfaces through use of a zero-current, four-electrode measuring technique and recessed electrodes.

More specifically, in one embodiment, the fluid sample flows through a predetermined region consisting of a matrix on which antiligand or ligand is immobilized. A suitable control molecule may be immobilized in a nearby predetermined region. Both test and control predetermined regions are small (typically on the order of 0.1 microliter), and the conductances of the test volumes are monitored using a zero-current four electrode technique, recessed electrodes, and an appropriate conductance measuring instrument.

Advantages of the present invention include its speed and ease of use. The measurement can be continuous and is capable of monitoring several ligands simultaneously. If desired, it can be label-independent, yet it can also use a variety of convenient, safe, inexpensive labels to increase sensitivity with little or no loss in speed and ease of use. The present invention also minimizes effects of phenomena that occur at electrode/electrolyte interfaces. Furthermore, the electrodes can be physically separate from the region containing localized antiligand or ligand; that allows the separate preparation of electrodes and localized antiligand or ligand compositions, allows their preparation to be potentially simple and inexpensive, and allows flexibility in choosing methods, techniques and materials. Finally, a variety of instruments exists which can be used or modified to measure changes in bulk conductance due to ligand/antiligand interactions.

BRIEF DESCRIPTION OF THE DRAWINGS

FIG. 1A shows the change in the conductance ratio between a test sensor and a control sensor after addition of a fluid sample containing a constant concentration of ligand;

FIG. 1B is a calibration curve relating the initial rate of change of the conductance ratio to a known concentration of ligand in the fluid sample.

FIG. 16 is a schematic diagram showing further details of the transformer circuit of FIG. 14.

FIG. 17 is a schematic diagram showing further details of the shield and guard driver amplifiers of FIG. 14.

FIG. 18 is a schematic diagram showing further details of an AC bi-quad amplifier used in the circuit of FIG. 14.

FIG. 19 is a schematic diagram showing further details of the phase shifter circuit of FIG. 15.

DETAILED DESCRIPTION OF THE INVENTION

Figure 2A:
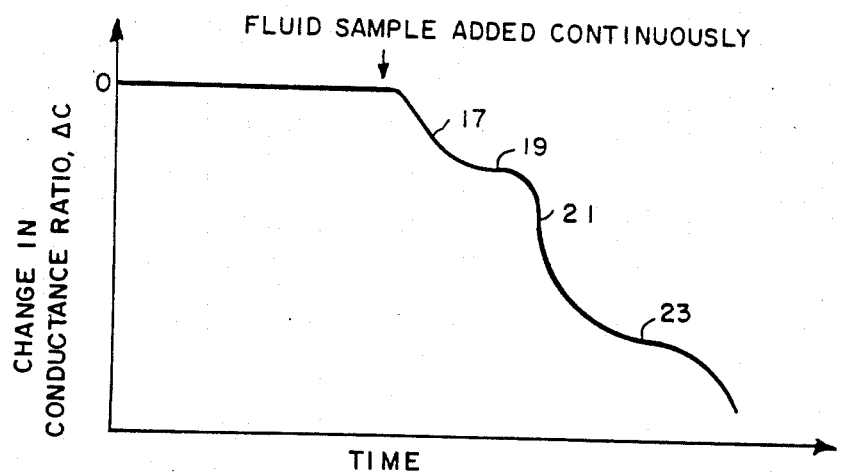
FIG. 2A shows the change in the conductance ratio in a fluid sample in which the ligand concentration varies with time.

The following definitions are provided in order to facilitate understanding of the present invention. To the extent that the definitions vary from meanings within the art, the definitions below are to control.

Ligand means substance to be detected that specifically binds with another substance, the antiligand.

Antiligand means substance used to probe for the presence of a ligand that specifically binds to the ligand.

Test Volume means the volume whose conductance is measured to determine the occurrence of ligand/antiligand interaction in a predetermined region.

Predetermined Region means region having ligand or antiligand localized in it.

Localizing Means is the means used to localize antiligand or ligand in the predetermined region.

Contacting means is the means used to insure contact between the localizing means and fluid sample containing the ligand of interest.

Measuring Means is the means used to measure the bulk conductance of the test volume.

Sensor means the localizing and measuring means taken together.

Efficiency E of a sensor means the resistance of the predetermined region divided by the resistance of the test volume.

Conductance ratio C means the conductance of the test volume divided by the conductance of the negative control volume.

IVEP Sensor means an Internal Voltage Equivalence Point sensor apparatus.

EVEP Sensor means an External Voltage Equivalence Point sensor apparatus.

Bioregion means localizing means that is mounted on a biolayer.

Biolayer means the combination of one or more bioregions and an appropriate supporting fixture, constructed for easy insertion or placement of bioregions into or onto a sensing apparatus.

This invention relates to methods, apparatus and sensors for determining the presence of a ligand in a fluid sample by measuring ligand-induced changes in bulk electrical conductance.

In a preferred embodiment, antiligand to the ligand of interest is localized within a predetermined region. The predetermined region is exposed to the fluid sample to be analyzed, and the bulk conductance of a volume (the test volume) that at least partially contains the predetermined region is measured. Changes in the bulk conductance of this test volume that arise as a result of ligand-antiligand interaction in the predetermined region may be used to determine the presence of ligand in the fluid sample.

More generally, a variety of spatial relationships may exist between the predetermined region and the test volume. For example, the test volume may entirely include the predetermined region or alternatively, the predetermined region may entirely include the test volume. The predetermined region and the test volume may overlap, may be near each other but not overlap, or may be at a distance from each other.

Although the present methods and apparatus are designed to detect the presence of a ligand in a fluid sample, they are readily modified to detect the presence of a ligand in a gas, e.g., by dissolving or bubbling the gas through an appropriate fluid, or in a solid, e.g. by dissolving the solid in an appropriate fluid.

While not wishing to be bound by theory, it is believed that a ligand-specific conductance change occurs in the test volume because the presence or absence of ligand influences the distribution and/or concentration of charged species which carry electric current through the test volume. For example, when ligand binds to antiligand immobilized in the predetermined region within the test volume, the bound ligand occupies space in the test volume which is then no longer available to conduct current.

Changes in bulk conductance that arise from ligand-/antiligand complex formation are in many cases small (on the order of a percent or less). Large nonspecific changes in conductance can arise from local environment variations, for example, in temperature, composition of the fluid sample, viscosity changes, or nonspecific binding of proteins or other substances to the predetermined region or test volume. These changes can tend to swamp out the ligand-specific changes one is looking for. For example, a change in temperature of 1 degree Celsius can produce a 2% to 3% change in conductivity—perhaps larger than the entire ligand-specific effect one is seeking.

In order to be able to detect and quantify accurately the ligand-specific conductance change of interest in the presence of nonspecific changes, in a preferred embodiment one compares the bulk conductance of a test volume with the bulk conductance of at least one control volume. Both positive and negative control volumes may be used.

In general, a negative control volume should be as free as possible of non-specific interactions that cause changes in bulk conductance. At a minimum, the negative control volume should not contain antiligand which reacts with the ligand of interest. It may be sufficient for the control volume simply not to contain any localized substance therein. However, for the strongest application of this differential, or comparative, principle, the test and negative control should be as similar as possible. For example, in a preferred embodiment the negative control volume at least partially contains at least one predetermined region that is exposed to the fluid sample, and this predetermined region has localized in it a molecule whose physical properties are similar to the physical properties of the antiligand localized in the predetermined region of the test volume, but that does not bind specifically to the ligand of interest. For instance, if a test predetermined region contains mouse IgG directed against a hepatitis virus antigen, a good negative control could be mouse IgG from a naive animal. The use of this differential technique relaxes the need for precise external temperature measurement and control. This greatly simplifies conductance measurements and helps make them more precise. Specific apparatus that makes use of differential techniques is disclosed later.

The conductance of a test volume can be compared with that of a negative control volume in various ways. For example, the value of each conductance may be measured, then that of the negative control subtracted from that of the test volume manually or electrically. Preferably, the conductances are expressed ratiometrically as a function of time, using the conductance ratio C, where $$C = \frac{\text{conductance of test volume}}{\text{conductance of negative control volume}}.$$

The test volume and/or the negative control volume can be further compared with a positive control volume. In this case a positive control ligand is present in known concentration in the fluid sample, and the positive control volume at least partially contains a predetermined region which itself has localized within it an antiligand which reacts with the positive control ligand. The test volume and the positive control volume may be compared to the negative control volume to correct for non-specific conductance changes, then to each other. The positive control signal can be used as a calibration method, as a way to monitor flow, or as a check on proper functioning of the method and apparatus.

Localization of antiligand can be accomplished in a variety of ways. Preferably, localization comprises immobilizing antiligand on a matrix. A variety of commercially prepared matrices are available. Such materials are easy to handle, and antiligands are easily bound to them in straight forward ways known to those skilled in the art. Matrices include gel beads, gel layers, glass beads, polymeric beads, microporous membranes, porous paper, filter material, or mixtures thereof. Preferably, the matrix is a porous membrane or paper that binds a variety of antiligands, such as nitrocellulose filters (Millipore Corporation, Bedford, MA). Different antiligands may be bound to different predetermined regions of matrix material, allowing multiple ligands to be detected in a single fluid sample.

Localization of antiligand may also be accomplished by confining the antiligand within a region defined by the boundaries of a semi-permeable membrane that is permeable at least to the ligand but not to the antiligand. For example, the predetermined region may consist of an antibody solution confined by a dialysis membrane.

The fluid sample and the predetermined region may be brought into contact in a variety of ways as described in more detail herein below. For example, a flowing stream of sample fluid may be contacted with the matrix of the predetermined region. The fluid may flow either through the matrix or past the matrix with diffusion carrying the ligand of interest into the matrix.

Where the predetermined region comprises antiligand confined within a semi-permeable membrane, fluid is caused to flow past the membrane. The ligand diffuses through the membrane into the predetermined region.

The present invention may be used in any situation where a ligand-antiligand pair associate. Examples of ligands which may be detected using this system are antigens bound to cell surfaces or other particles, free antigens, haptens, antibodies, nucleic acids, enzymes or mutant enzymes, cofactors, enzyme substrates, receptor proteins, permease proteins, transport proteins, specific binding proteins such as periplasmic proteins, molecules bound by a receptor protein or other binding proteins, carbohydrates, lectins, metal ions, metal binding proteins or other specific binding substances. In each of the above cases, there is a substance that specifically binds to the ligand mentioned. For example, if the ligand is an antigen, the antiligand may be an antibody. If the ligand is an antibody, the antiligand may be an antigen. If the ligand is a nucleic acid sequence, the antiligand may be a complementary nucleic acid sequence. If the ligand is a hormone, the antiligand may be a receptor protein for that hormone, etc. This list of ligands and antiligands is not meant to be exhaustive but simply to illustrate the general principal that this invention may be used to detect any ligand for which an antiligand is known to exist, can be found, or can be constructed.

In a particularly useful application of this invention ligands on cell surfaces may be used to detect the presence of whole cells or particles, for example, red blood cells, white blood cells, bacteria, or membrane fragments derived from them. The method of the present invention is particularly powerful in such cases because the ligand is already associated with a nonconducting volume that is much larger than its own (molecule-sized) volume.

It is increasingly becoming possible to synthesize and/or modify molecules so as to give them the properties desired for specific antiligands such as a particular affinity or specificity. For example, mutant enzymes can be isolated with altered affinity, specificity or enzymatic activity. Antiligands can be treated chemically to alter their properties. Nucleic acid sequences may be synthesized, specific peptide sequence may be synthesized, or nucleic acid sequences that direct the synthesis of particular proteins may be specifically altered, e.g. by using techniques of genetic engineering, thus allowing the synthesis of altered proteins. These and other techniques known to those skilled in the art allow use of an increasing variety of antiligands with the present invention. References to some of these techniques may be found in the following, the disclosures of which are incorporated by reference herein: Advances in Enzyme Technology: "Artificial, Semisynthetic, and Designed Enzymes", (Technical Insights, Inc., Ft. Lee, NJ); Morinaga et al., Biotechnology, July 1984, p. 636.

Antiligands may be used that have either high affinity or low affinity for the ligand. High affinity means that the antiligand tends to bind strongly to the ligand, low affinity that it tends to bind weakly. A useful quantitive measure of affinity is the affinity constant K, which is equal to the concentration of free ligand needed to saturate half the antiligand binding sites at equilibrium (as long as the total number of ligand molecules is much is larger than the number of binding sites). When the affinity is high, the affinity constant is low, and vice versa. More specifically, antibodies with affinity constants less than $10^{-10}$M are generally considered high affinity, and antibodies with affinity constants greater than $10^{-8}$M are considered low affinity. For the purposes of the present invention, high and low affinity are typically defined situationally: An antiligand is considered high affinity when the concentration of the ligand of interest in the fluid sample is much higher than the affinity constant, and low affinity otherwise. While not wishing to be bound by theory, models are described below that are helpful in understanding how ligand/antiligand interactions may be quantitated.

In the high affinity situation, the rate of association $r_1 = k_1 (L)(AL)$ of ligand and antiligand to form a complex greatly exceeds the rate of dissociation $r_2 = k_2 (L/AL)$ of ligand/antiligand complex as long as a significant fraction of the binding sites are unoccupied; furthermore, substantially all binding sites are occupied at equilibrium. [In these expressions $k_1$ is the forward rate constant, $k_2$ is the backward rate constant, and (L), (AL) and (L/AL) are respectively the concentrations of free ligand, unbound antiligand, and ligand/antiligand complex in the predetermined region.] This follows from the definition of the affinity constant K, where $K = k_2/k_1$.

Thus, to a first approximation, the rate of dissociation $r_2$ of ligand/antiligand complex may be ignored, and the association of ligand and antiligand is essentially irreversible. As fluid sample passes through the matrix in such a situation, binding is substantially quantitative as long as the fluid passes through the matrix slowly enough and a significant fraction of the binding sites are available; that is, virtually 100% of the ligand binds to immobilized antiligand and is removed from the fluid sample. In practice, the flow rate needed for quantitative binding depends on the reaction conditions such as salt concentration, temperature, and the thickness and pore size of the matrix as well as on the nominal forward reaction rate. Typically, linear flow rates on the order of millimeters or tenths of millimeters per second allow quantitative or near-quantitative binding to a matrix that is 0.1 mm thick, 0.45 um in pore size and $10^{-4}$M in immobilized antiligand.

Binding need not be quantitative. In some cases it may be appropriate to pass fluid through the predetermined region at a rate that does not give time for quantitative binding. In such a case it may be satisfactory to know the percent of binding which occurs, even if this is not 100%. In an extreme case, fluid will be passed through the predetermined region so quickly that only a small portion of the ligand entering the predetermined region binds to it during its transit time.

Quantitative binding conditions have the advantage that the amount bound is not strongly dependent on the exact concentration of immobilized antiligand or on the exact thickness of the predetermined region, as long as the matrix remains unsaturated. The extreme non-quantitive binding situation, which may approximate that of homogeneous kinetics, has the advantage that it is not strongly dependent on the flow rate.

For quantitative binding, the amount of ligand bound per unit time will be proportional both to the concentration of ligand in the fluid sample and to the flow rate. This yields a high affinity, or kinetic, measure of ligand. For example, if the conductance ration C is plotted as a function of time (as noted above), the slope of the resulting line is a function both of ligand concentration and flow rate. Thus, if the flow rate is known, ligand concentration can be determined. For instance, referring now to FIG. 1A, if the concentration of the ligand is constant, the slope 10 will be constant until the predetermined region becomes saturated 12, assuming a constant flow rate.

The observed value of the slope dC/dT will depend not only on the concentration of the particular ligand in the fluid sample and the flow rate, but also on other particulars of the experiment set-up, such as (1) the pore size of the predetermined region; (2) the total volume of fluid in the bioregion available for ion flow; (3) the efficiency E of the sensors, (4) the effective size of the ligand immobilized (e.g. the partial molar volume if the ligand is a molecule or ion, or the cell volume if the ligand is bound to a cell surface); and (5) changes in partial molar volume of ligand or antiligand or both resulting from changes in their structure due to binding. Hence, a standard curve such as in FIG. 1B must be determined for a particular set of experimental conditions used. Once this is done, however, the presence and concentration of ligand in an unknown sample fluid may be determined by reference to the standard curve.

Because dC/dt depends upon (4) and (5) above, the present invention may be used to study or determine such characteristics. This could be useful in research, e.g. studies of conformational changes in antibodies when they bind their antigens. (See *Protein Conformation as an Immunological Signal*, Celada et al., Plenum, NY (1983)).

Various means may be employed to assure a known flow rate, as will be apparent to one skilled in the art. For instance, the apparatus may be designed to maintain a constant, known flow rate throughout the course of a measurement, e.g., through use of appropriate fluid resistors and/or a peristaltic pump. Flow may be measured by various commercially available devices (e.g., a G-1000 microliter per minute flow meter with regulator valve, from Gilmont Instruments, Great Neck, NY). For particular sample fluids and ligands the change is conductance of a matrix due to both specific and nonspecific binding of material from the fluid sample may well be correlated in a known way with the change in flow rate through the filter at a given applied pressure, since both changes may arise from common causes such as the binding of material from the fluid sample. The conductance ratio itself may sometimes thus be used as a measure of flow rate.

Referring now to FIG. 2A, if the ligand concentration in the fluid passing through the predetermined region varies with time, the slope dC/dt will vary with time. For example, at point 17, the ligand concentration in the fluid passing through the apparatus is significant, and as a result, the conductance ratio decreases at a significant rate as ligand binds to and occupies space in the predetermined region. Later, at point 19, the ligand concentration has dropped to an undetectable level, and the conductance ratio is not changing detectably. Still later, at point 21, the ligand concentration has risen to a very high level, and finally, at point 23, it has fallen again to a very low level. The ligand concentration at a particular time may be determined by measuring the instantaneous rate of change of the conductance ratio, i.e., the slope of the graph at that time, again assuming the flow rate is held constant, or is at least known. This provides a continuous measure of ligand concentration.

Figure 2B:
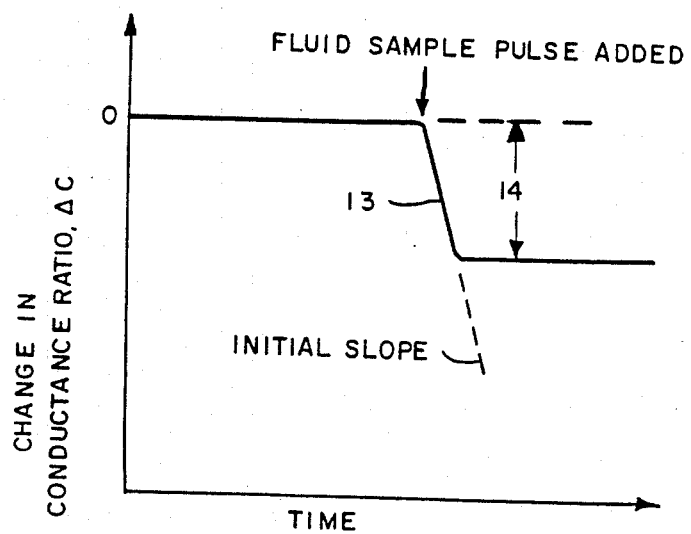
FIG. 2B shows the change in conductance ratio after a fluid sample pulse.

Sample fluid may also be contacted with the predetermined region in a pulsed fashion resulting in a curve such as that shown in FIG. 2B. For example, fluid sample may be injected into a flowing buffer stream of the same conductivity using standard commercial valve equipment (e.g. Rheodyne valves with sample injection loop, Rheodyne Instruments, Cotati, CA). After a known time, depending on the sample volume and the flow rate, the sample pulse will pass entirely through the sensor. Where ligand binding is quantitative, either the rate of change 13 of the conductance ratio or the total change 14 of the conductance ratio may be used to quantitate the concentration of ligand as long as the predetermined region has not become saturated. The latter method has the advantage that it is not dependent upon knowing the exact flow rate. The former has the advantage that it is faster. Either method may be most appropriate under particular experimental circumstances.

Figure 3A:
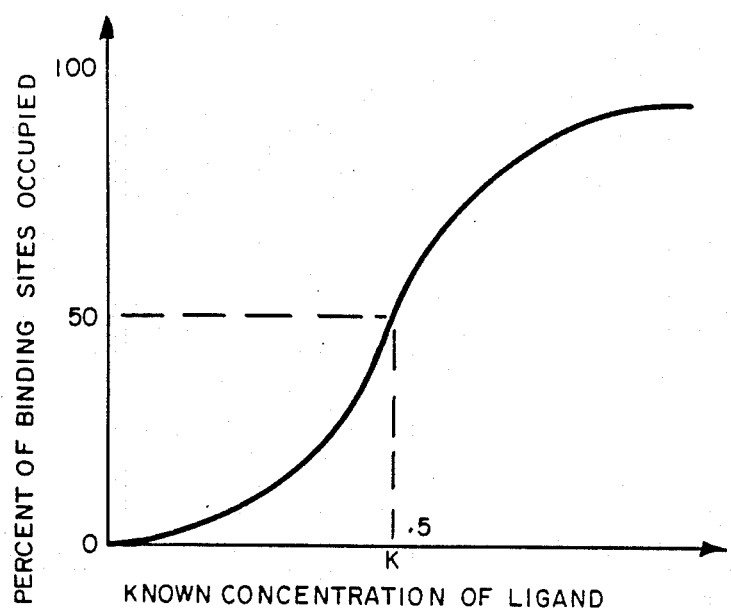
FIG. 3A is a calibration curve relating the percent of binding sites occupied in a predetermined region at equilibrium to a known concentration of ligand.

As mentioned above, in some situations it may be desirable to use an antiligand with low affinity for its ligand. Such a situation can arise, for example where the ligand of interest is present in high concentration in the fluid sample, e.g. $10^{-3}$M, and it is desirable to monitor the concentration of ligand continuously over an extended period of time. Since the predetermined region has a limited capacity to bind ligand, the time over which concentration could be monitored, given quantitative binding, would be limited. This potential problem is addressed by using an antiligand whose affinity constant K typically is within an order of magnitude of the concentration of ligand expected in the fluid sample, i.e., a low affinity situation. In this situation, the rate of dissociation $r_2$ of ligand/antiligand complex is significant compared to the rate of association $r_1$ (i.e., binding is reversible), and a significant fraction of the binding sites are unoccupied at equilibrium. The fraction of unoccupied or occupied binding sites will be a known function of the concentration of ligand under given experimental conditions, as shown in FIG. 3A. (In this figure, K, the affinity constant 15, represents the concentration of ligand needed to saturate half of the binding sites in the predetermined region at equilibrium as noted above.) A curve such as that of FIG. 3A can thus be used as a standard curve to determine the presence or concentration of a ligand in a fluid sample. The dynamic range of such low affinity, or equilibrium, methods can be increased if desired by using several predetermined regions containing antiligands for the same ligand but with different affinities, or by immobilizing several such antiligands in a single predetermined region.

Figure 3B:
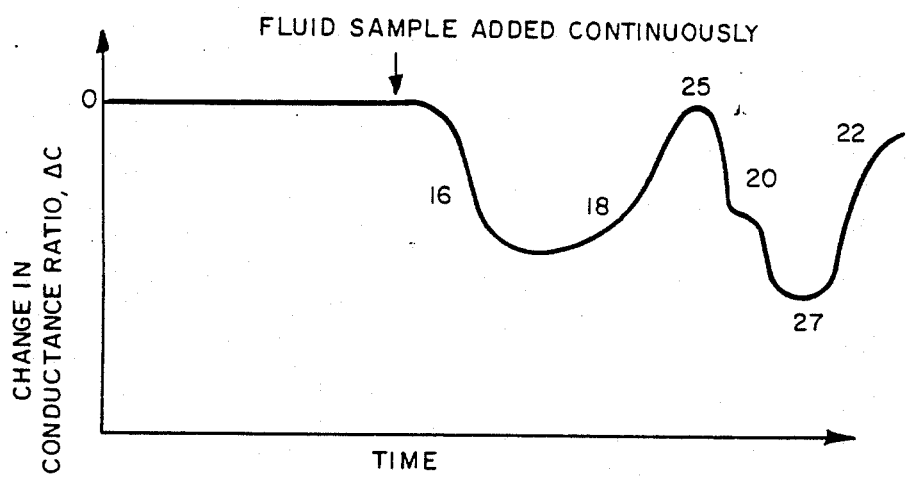
FIG. 3B shows the change in conductance ratio monitored via measurements made at equilibrium.

Referring to FIG. 3B, there is shown an example of the use of low affinity antiligand in the detection of varying concentrations of ligand in a fluid sample. When the concentration of ligand in the fluid sample passing through the sensor rises (16), the conductance ratio falls as ligand binds to and occupies space in the predetermined region, making that space unavailable to current flow. When the ligand concentration falls (18), the conductance ratio rises. At 25, the ligand concentration has fallen to a very low level, far below the affinity constant, so that little or no ligand remains bound to the predetermined region, and the conductance ratio hence approaches or equals its original value. Later still, the ligand concentration rises again (20), reaches a new high (27), then falls again (22).

The response time of this method depends on the dissociation rate $r_2 = k_2 (L/AL)$ of the ligand/antiligand complex. For antibodies, many of which have forward rate constants $k_1$ on the order of $2 \times 10^7$ per molar per second, this means that antibodies with affinity constants of $10^{-9}M$ or greater have response times on the order of a minute or less.

It should be noted that antibodies or other antiligands with fast dissociation times can serve as the sensing elements in convenient, fast reusable sensors. Such sensors require little or no treatment to remove bound ligand.

Appropriate choice of low or high-affinity antiligands can be made by those skilled in the art. As noted above, antiligands themselves may be altered to vary their affinity. Also, affinity constants can be altered in a variety of other ways, such as variation in salt concentration, temperature, or amounts of detergent included in an experiment, and chemical alteration of the matrix to which antiligand is immobilized.

The sensitivity of the high affinity method is inversely proportional to the volume of the predetermined region. The larger the predetermined region, the larger the total number of binding sites (assuming a defined fraction of predetermined region by weight is antiligand); thus, the larger the number of ligand molecules required to result in a given fraction of occupied binding sites. Therefore, where sample size is limited or the concentration of ligand in the sample is low, it is desirable that the predetermined region be small. Further, the sensitivity of the measurement is also proportional to the efficiency, E, of the particular sensing apparatus. Thus, both the test volume and the predetermined region should be small for maximum sensitivity. Preferably, the test volume is on the order of about 0.1 microliter to one microliter or even less, the volume of the predetermined region is also on this order or less, and the efficiency E is 10% to nearly 100%. Such apparatus is described herein below.

As an example, suppose that one ml of a fluid sample containing 1 ug/ml ligand flows through a sensor, the volume of whose predetermined region is about one microliter, with quantitative binding of ligand; then, assuming the specific gravity of the ligand is on the order or one, the microgram of bound ligand will occupy a volume of about one nanoliter within the predetermined region, i.e., 0.1% of the volume of the predetermined region, yielding a conductance change of about 0.1% (or less if the efficiency E of the sensor is low). If the volume of the predetermined region is ten times smaller (0.1 microliter), on the other hand, the same one microgram of ligand will occupy 1% rather than 0.1% of the predetermined region and thus will yield a larger conductance change.

In some cases it may be desirable to amplify the change in conductance that occurs when a ligand and antiligand bind to each other. As mentioned above, it is believed that the change in conductance often is proportional to the volume occupied by bound ligand. This signal can therefore be amplified if the presence (or absence) of additional non-conducting volume can be associated with the binding of ligand. Resulting conductance changes will then reflect the presence (or absence) of this additional volume. This may be accomplished in a variety of ways.

More specifically, a complex can be formed between a ligand which interacts with the antiligand and a particle. The particle may be composed of a variety of materials such as antiligand which interacts with the ligand of interest, antiligand which interacts with the ligand of interest bound to an amplifying substance, macromolecules, molecular complexes, latex beads, lipid vesicles, non-conducting polymer beads, other non-conducting particles, partially conducting particles, magnetic particles or mixtures thereof. A variety of methods of attaching ligands to appropriate particles are known to those skilled in the art.

The simplest use of a particle for enhancing the change in bulk conductance is where ligand in the fluid sample is directly bound to particles by incubation. The ligand/particle complex in the fluid sample is then exposed to the predetermined region, yielding a larger signal as ligand/particle complexes bind than if ligand alone had bound. In a variation of the above, a known amount of ligand that interacts with antiligand may be added to the fluid sample. This ligand can compete with ligand/particle complexes for antiligand, thus forming the basis for a competitive particle-enhanced conductance assay.

In another variation, a known amount of a known ligand that interacts with antiligand is first bound to particles and this comlex is added to the fluid sample; ligand from the fluid sample can then compete with this ligand/particle complex, forming another type of particle-enhanced competitive conductance assay.

In yet another variation, a predetermined region containing immobilized antiligand is exposed to a preformed complex comprising ligand and a particle, and the complex is allowed to bind to the region. This region is then exposed to sample fluid containing ligand, which can compete off the ligand/particle complex. In a variation of this technique, the ligand/particle complexes released from a predetermined region may themselves be detected, for example by monitoring the conductance of a test volume associated with a filter matrix that tended to trap such released complexes, where the test volume is located at a distance from the predetermined region (i.e., downstream). The detection may also be done by monitoring a color change or a pressure change across the filter, or by other means.

Figure 4A:
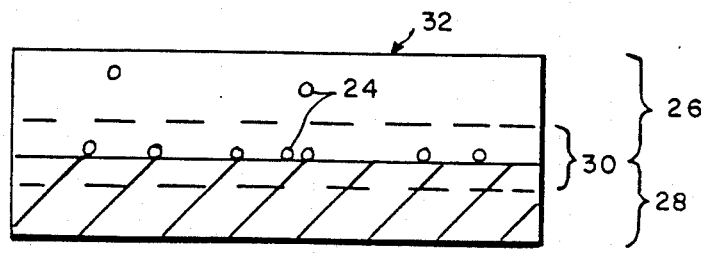
FIG. 4A illustrates the binding of ligand/particle complexes to a predetermined region where the test volume includes at least the surface of the predetermined region.

In yet another variation, referring now to FIG. 4A, a known amount of ligand is complexed with a particle. This preformed complex 24 is compartmentalized in at least one region 26 that is adjacent to predetermined region 28. Compartment 26 must itself be at least partially within test volume 30. This forms the basis of another type of particle-enhanced competitive conductance assay. It may be used to continuously monitor ligand in a fluid sample. Compartment 26 may be formed, for example, by confining complex 24 within a semipermeable membrane 32 that is permeable to the ligand of interest. When the sample fluid contains no free ligand, complex 24 will tend to lie within the test volume, since it will bind to the antiligand in the predetermined region. When the sample fluid contains a high level of the ligand, many complexes 24 will lie outside test volume 30, changing the conductance of the test volume, since they will be competed off predetermined region 28 by the ligand in the fluid sample and will be free to move through compartment 26. The ligand/particle complex 24 may bind only to the surface of the predetermined region, or it may bind internally as well.

Figure 4B:
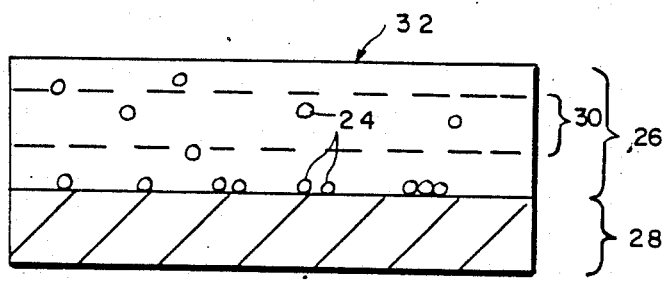
FIG. 4B illustrates the binding of ligand/particle complexes to the surface of a predetermined region where the test volume does not include part of the predetermined region.

It should be noted that the test volume and the predetermined region do not have to overlap to produce a workable method. In FIG. 4B, for example, test volume 30 and predetermined region 28 do not overlap but nevertheless are proximate enough to each other so that ligand-antiligand interaction occurring in the predetermined region influences the conductance of the test volume.

More specifically, ligand diffuses into compartment 26 and predetermined region 28 and competes with particle complex 24 for antiligand binding sites. When the ligand concentration in the fluid sample is low, most of complex 24 is bound to the predetermined region 28. When it is high, most of complex 24 is free to move through compartment 26. If test volume 30 is at a distance from the surface of predetermined region 28, as shown in FIG. 4B, the test volume conductance will increase when the ligand concentration is low, as complexes 24 leave test volume 30 and bind to predetermined region 28. If the test volume 30 includes at least part of the region above the surface of the predetermined region occupied by bound complexes, the text volume conductance may decrease when the ligand concentration is low, as complexes bind to the surface and occupy part of the volume of the test region. In either case, measuring the conductance of the test volume can be used to determine the presence and concentration of ligand in the fluid sample.

Magnetic particles complexed with ligand may be used in conjunction with a magnetic field to modify the ability of particles to stick to a predetermined region or to modify their distribution near the predetermined region. For example, a magnet placed under predetermined region 28 in FIG. 4A or FIG. 4B tends to attract ligand/particle complexes 24 if they contain magnetic material. By varying the strength or distance of the magnet, one can vary the ability of particles to stick to predetermined region 28 and also the average concentration of particles at different distances above this region.

Similarly, a tangential flow field may be used to influence the ability of particles to stick to a surface. For example, one could remove particles from a fluid sample while measuring the amount of ligand present by passing the sample rapidly past a filter containing immobilized antiligand; if the filter's pore size is smaller than the particles, they will be excluded from the filter and also will be prevented from piling up on the filter by the "sweeping" action of the fluid flowing tangentially over the surface. Particle-free fluid carrying ligand can meanwhile pass through the filter, allowing binding of ligand to the immobilized antiligand. On the other hand, if one wishes to measure the presence of particles which themselves have ligand bound to their surface, one might use a slower flow, strong enough to minimize non-specific particle sticking but weak enough to allow sticking of the desired particles via ligand/antiligand binding.

Conductance changes can also be amplified by forming a complex between a particle and antiligand specific for the ligand of interest. In one such embodiment, a known amount of antiligand and particles are incubated to form a preformed complex. This complex is added to the fluid sample. Ligand in the sample binds to antiligand in the complex and also to antiligand localized in the predetermined region. The number of particles bound to the predetermined region depends on the amount of free ligand in the sample. This gives a sandwich type of immunometric particle-enhanced conductance assay. In a variation of this method, antiligand itself is the particle, or a polymerized complex of antiligand is the particle.

Particles that may be complexed with antiligand are similar to those that can be complexed with ligand, and their methods of use with the present invention will be apparent to those skilled in the art. For example, a conductance version of the sandwich Tandem assay of Hybritech (San Diego, CA, U.S. Pat. No. 4,376,110) is easily derived: A monoclonal antibody specific for an extended antigen is immobilized, e.g. on a nitrocellulose filter. Fluid sample containing the antigen is exposed to the filter, allowing antigen to bind. Then a second, non-interfering monoclonal antibody specific for the antigen, complexed with a particle if desired, is allowed to bind to the antigen, and a conductance change resulting from this binding is monitored.

In accordance with yet another variation, ligand that interacts with antiligand to the ligand of interest if localized within a predetermined region. The predetermined region is exposed to the fluid sample and also to an antiligand which interacts both with the ligand in the fluid sample and with ligand localized in the predetermined region. The bulk conductance of a test volume that at least partially contains the predetermined region is measured.

As with the previously described embodiment wherein antiligand is localized in the predetermined region, the bulk conductance of the test volume may be compared with the bulk conductance of one or more control volumes. The localized ligand may be immobilized on a matrix, and the matrix may be contacted with a flowing stream of fluid sample. Alternatively, ligand may be localized by being confined within the boundaries of a membrane, e.g. as part of a particle complex, or in a polymerized form. This membrane is permeable to the ligand to be detected and to the antiligand that interacts with the ligand to be detected. These embodiments are similar to the embodiments taught above that use localized antiligand. Variations will be apparent to one skilled in the art and are intended as part of this invention.

It should be understood that conventional labelling techniques may also be used in conjunction with the present invention. For example, in a sandwich assay where ligand from the fluid sample has been bound to immobilized antiligand and then been exposed to a preformed particle complex containing a second antiligand, the complex may in addition contain an enzyme label, in a manner similar to ELISA assays. Enzyme substrate is then passed over the sandwich formed and thereby generates a desired conductance change in situ in the predetermined region.

For example, the enzyme may convert part of the substrate into gas bubbles. Since these bubbles are non-conductive, they lower the conductance of the test volume. Alternatively, a substrate may be used that is enzymatically converted to an insoluble precipitate which binds to the predetermined region and which again decreases the conductance of the test volume. These protocols are particularly advantageous embodiments because the label produced can be detected in situ, in a highly localized region. Of course, other enzymes, substrates, and labels may be used. For example, an enzyme could be used that generates a charged species, thus changing the conductivity.

Other techniques that can improve performance of ligand/antiligand assays are known to those skilled in the art, and many of these can be employed with the present invention. For example, U.S. Pat. No. 4,092,408 teaches a method for achieving more reproducible, efficient binding of antibody to a matrix by using a precoat of second antibody. There are also techniques which teach the use of second antibodies labelled with biotin or enzymes, and many of these may be employed also, as long as the label changes the conductive in a desired way.

The sensitivity of the above ligand/antiligand assays may be enhanced by decreasing interfering effects such as nonspecific binding. The skilled practitioner may use as a guide in enhancing the sensitivity of such conductance-based assays techniques used in similar non conductance-based assays. For example, in trying to detect a particular antigen binding to immobilized antibody, it is possible to first immobilize to an appropriate matrix a protein that binds the antibody such as protein A or second antibody. The primary antibody is then immobilized by binding to the protein A or second antibody. This can result in less non-specific binding when antigen binds than if the primary antibody had been directly bound to the matrix.

Because the present invention depends upon measuring changes in the conductance of a test volume, appropriate care should be taken by the practitioner to avoid the introduction of material into the test volume which can interfere with the measurement, such as dirt particles, cells, and random bubbles. For example, pre-filtration and deaeration of sample or buffer may be appropriate in some circumstances. In other cases, unwanted particles may be excluded from part or all of the test volume through use of a membrane, gel, or porous material which is impermeable to the particles. For example, to measure the concentration of a molecule in blood without interference from conductance changes due to variations in the number or orientation or red blood cells in the test volume, the test volume could be occupied by a porous matrix that allows plasma, but not cells, to enter, e.g., by diffusion.

The bulk conductance of the test volume can be measured in a variety of ways. In a preferred embodiment, conductance is measured with electrodes that are in contact with an electrolyte using a zero-current, four-electrode measuring technique. In this method two electrodes, called current electrodes or power electrodes, are used to provide a current that passes through the test volume whose conductance is being measured, and two other electrodes, called voltage electrodes or working electrodes, are used to measure the resulting voltage drop across the test volume. The voltage electrodes are part of a circuit with essentially infinite impedance, so that virtually zero net current flows through the voltage electrode surfaces, hence the name zero-current, four electrode technique. This tends to reduce problems associated with phenomena at electrode surfaces, such as polarization impedance; voltages associated with the presence of a polarization impedance must be small, since no net current flows across the impedance. A further discussion of this method is given in *Introduction to Bioinstrumentation*, by C. D. Ferris, Humana Press, Clifton, NJ, pages 109–116 (1978), herein incorporated by reference.

Preferably, the voltage electrodes are recessed from the current flow and the current electrodes are recessed from the test volume to reduce problems associated with polarization impedance. Specific apparatus incorporating these principles is disclosed herein below. Other recessed four-electrode conductivity cells are taught in U.S. Pat. Nos. 3,963,979 and 3,939,408, herein incorporated by reference.

Two-electrode methods may also be used to measure conductance. (See Pederson and Gregg, IEEE Journal on Ocean Engineering, Vol. OE-4, No. 3 (1979)). These generally require higher frequency in order to obtain high accuracy.

Another method of measuring conductance involves the use of electrodes coated with an insulating material to avoid electrolyte-electrode interface effects. The coated electrodes are capacitatively coupled to the electrolyte through a thin insulating coating. This method generally requires even higher frequencies. (See Huebner, G. L., "Notes on radio frequency salinity measuring equipment at Texas A and M College", Publ, 600, Nat. Acad. of Sci. National Research Council, 1958, herein incorporated by reference.)

At even higher frequencies, e.g., gigahertz frequencies, it is possible to measure the dielectric properties of a fluid sample rather than the conductive properties.

Another technique which avoids the direct contact of electrodes with electrolyte is inductive coupling. An inductive salinometer is described in an article by Brown and Hanson in Deep Sea Research, 8, 65–75, (1971). Also, commercial inductive salinometers are made by Beckman Instruments (Fullerton, CA) and Aanderaa Instruments (Bergen, Norway) among others. One (insulated) coil can be used to produce a current inductively in the test volume; the magnitude of this current, which is a measure of the conductance of the test volume, is detected inductively by another, pickup, coil. This method generally requires larger test volumes. Further, coils are difficult to miniaturize.

It should be understood that a variety of instruments can be used in conjunction with the various methods noted above to process signals from a particular conductivity sensor or set of sensors. Instruments of particular usefulness with the zero-current, recessed four-electrode methods, apparatus and sensors described herein are illustrated in Examples 8 and 9 below. A simpler, analog circuit for making zero-current, four-electrode measurements that can be modified for use with the present invention is illustrated on page 115 of Ferris, supra.

In accordance with the present invention, there is also provided an apparatus for determining the presence of a ligand in a fluid sample. In its simplest configuration the apparatus has three basic components, each of which performs a specific function in determining the presence of a ligand in a fluid sample. They are: means for localizing ligand or antiligand which interacts with ligand in a predetermined region of the apparatus (the "localizing means"); means for contacting the fluid sample with the localizing means (the "contacting means"); and means for measuring the bulk conductance of a test volume which at least partically contains the predetermined region (the "measuring means"). The localizing means and the measuring means together comprise the sensor.

Figure 5B:
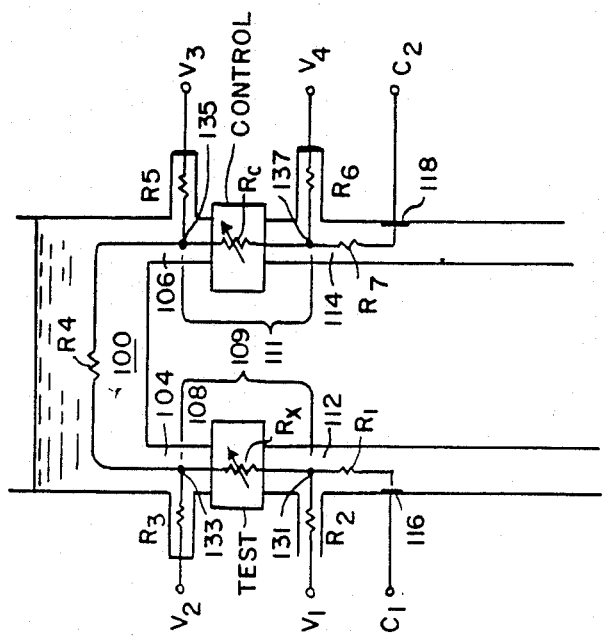
FIG. 5B shows the electrical equivalent.
Figure 5A:
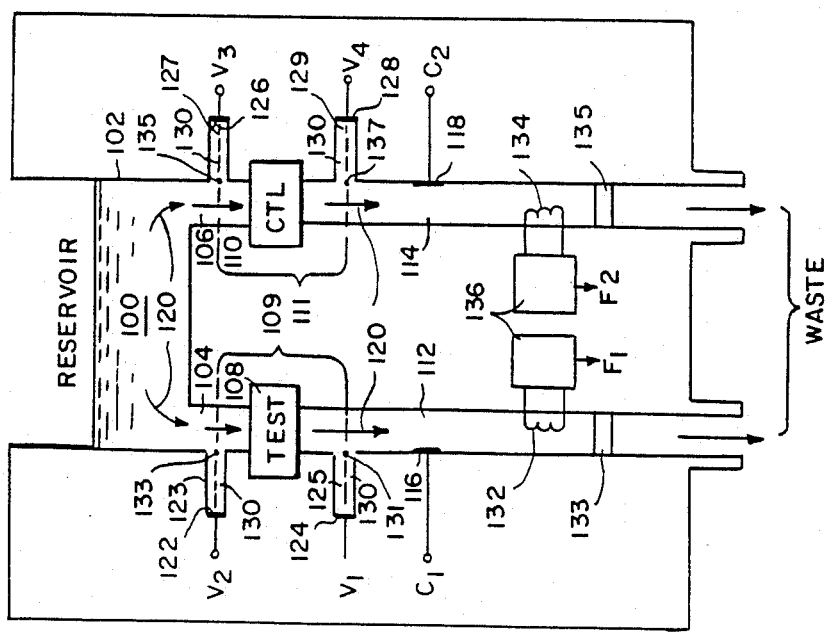
FIG. 5A shows typical apparatus used in determining the presence of a ligand in a fluid sample.
Figure 5C:
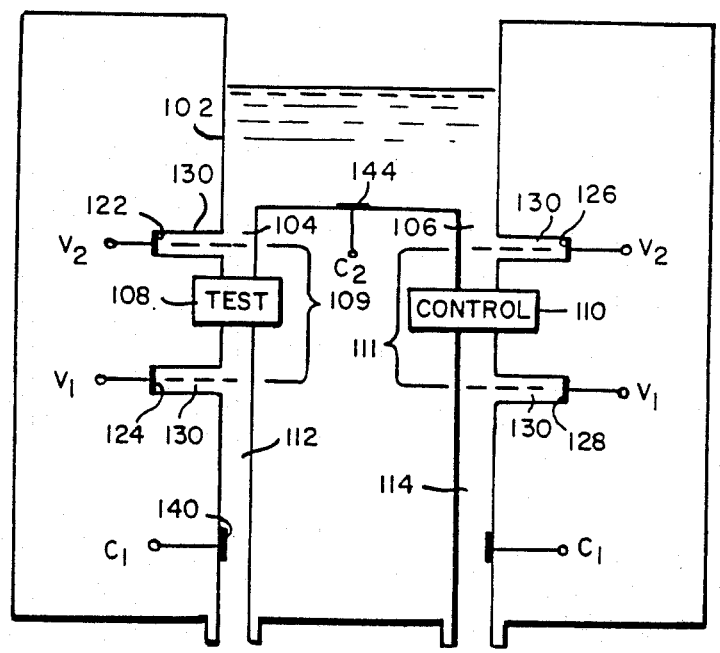
FIGS. 5C and 5D show other possible configurations of the apparatus.
Figure 5D:
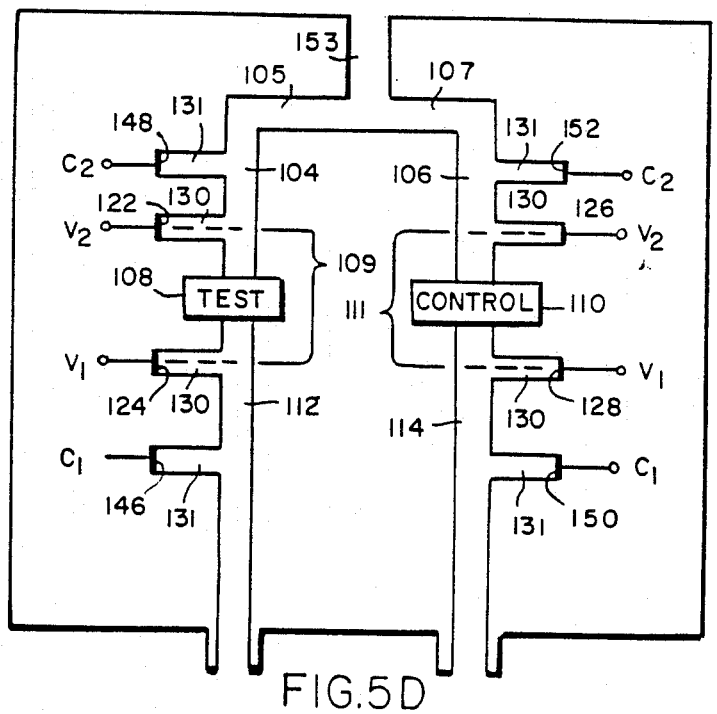

Referring now to FIG. 5A, there is shown a diagrammatic representation of a typical apparatus used in determining the presence of a ligand in a fluid sample by measuring the bulk conductance of a test volume. The test volume 109 at least partially contains a predetermined region 108 that itself contains means for localizing antiligand which interacts with the ligand of interest. The conductance of this test volume is compared to the conductance of a control volume 111 containing a control predetermined region 110 to increase the sensitivity of the measurement. FIG. 5A illustrates the physical arrangement of the apparatus, and FIG. 5B shows the electrical equivalent. FIGS. 5C and 5D show variations of the measuring means and contacting means.

Preferably, the localizing means comprises a matrix material that allows fluid to flow through it and that contains antiligand immobilized on it. The location of this matrix defines predetermined region 108 of test volume 109 (FIG. 5A). Likewise, the location of a matrix that contains immobilized on it a molecule similar to antiligand but that is substantially free of specific interactions which affect conductance typically defines predetermined region 110 of control volume 111. Antiligand in predetermined region 108 binds the ligand of interest as fluid sample flows through the matrix, changing the conductance of predetermined region 108 and test volume 109.

Typical matrix materials used as localizing means in several embodiments discussed below are microporous filters made of nitrocellulose or mixed esters of nitrocellulose and cellulose acetate (Millipore Corp., Bedford, MA or Schleicher & Schuell, Keene, NH). These filters have pore sizes ranging from 0.2 um or less up to 12 um. Lower pore sizes generally bind more antiligand per unit volume but have slower flow rates. Particular requirements, e.g., regarding flow rate, binding capacity, and amount of non-specific binding that can be tolerated for an experiment must be taken into account in choosing an appropriate matrix.

Nitrocellulose filter has long been known to be an excellent material for adsorbing proteins (Kuno and Kihara, Nature 215: 974–975; see also "Milliter Methods", published by Millipore Corp.) Both proteins and nucleic acids bind to it virtually instantaneously, so immobilization is easy. This and other immobilization procedures are well known to those skilled in the art (see, for example, Science 223 474–476 (1984), herein incorporated by reference).

While not wishing to be bound by theory the approximate change in conductance expected from maximal binding of ligand to a matrix made of nitrocellulose filter and loaded with antiligand as described in Example 1 will now be calculated.

Nitrocellulose filters such as HA Millipore (Millipore Corp.) bind about 1 ug of protein per $mm^2$ of area, given typical commercially available filters that are about 0.15 mm thick (this corresponds to a filter volume of about 0.15 $mm^3$, or 0.15 microliters, per $mm^2$ of area). Also HA Millipore is 79% void volume, with the remaining 21% consisting of solid matrix material. Thus, the volume of the matrix available for fluid flow, electric current flow, or antiligand binding, is approximately 0.12 microliters per $mm^2$ of matrix area. The partial molar volume of most hydrated proteins, including antibodies, is approximately 0.7 cc/g. (Most organic molecules have partial molar volumes and densities around 1.) Thus, 1 ug of protein occupies about $0.7 \times 10^{-6}$ cc, or about 0.7 nanoliters. The expected decrease in conductance caused by immobilization of 1 ug of a protein antiligand per $mm^2$ of matrix area is thus on the order of 1%, since $$\frac{0.7 \text{ nanoliters}}{0.12 \text{ microliters}} = \frac{0.0007 \text{ microliters}}{0.12 \text{ microliters}} \sim 0.6\%.$$

This concentration corresponds to a local concentration of antilgand in the predetermined region on the order of $10^{-4}M$ for a typically-sized protein antiligand of about 100,000 daltons, e.g. an antibody of 150,000 daltons.

If each immobilized antiligand molecule itself binds about one ligand molecule of about the same size, such as another protein, the ligand-specific conductance change associated with maximal ligand binding should then also be about 1%.

In some cases, the antiligand will have multiple binding sites (for example, see Example 1, in which the antiligand is an extended antigen with several antigenic determinants, and the ligand is a polyclonal antibody population from an immunized animal). The expected maximal signal strength will then be higher, since several volumes of ligand will bind per volume of immobilized antiligand, and the maximal concentration of bound ligand will also be higher. Conversely, if the ligand is a small molecule, the expected signal strength will be lower because although the maximal concentration of bound ligand molecules may be, say, $10^{-4}M$, the volume occupied by each bound ligand molecule is small.

While not wishing to be bound by theory, in general it is expected that the observed change in conductance ratio $\Delta C$ will be proportional both to the molar concentration b of bound ligand and to the partial molar volume v of the ligand: $\Delta C = s\, b\, v$, where s is a proportionality constant related to the signal strength. s itself will depend on a variety of factors, such as the efficiency E of the sensor used; it may be determined from a calibration curve such as that of FIG. 1B.

Other matrix materials may be used as well as nitrocellulose. For example, the columnar sensor of Example 4 uses cyanogen-bromide-activated Sepharose beads as a matrix material (Pharmacia Corp., Piscataway, N.J.). This matrix material also binds about 1% by weight or volume of many antiligands, and binding is easy as described in detail by the Pharmacia Corp. publication Affinity Chromatography Principles and Methods, 1979. The fact that for many matrix materials, the maximal conductance change is on the order of 1% if amplifying methods are not used points out the usefulness of methods and apparatus that allow accurate measurement and that use negative controls as described elsewhere, to help avoid obscuring of the signal by non-specific effects.

The particular matrix material chosen will depend on many characteristics such as binding capacity, ease of binding, ease of handling, size and shape of desired predetermined regions and associated apparatus, flow rate desired, speed and sensitivity desired, etc.

While the 1% localized concentration of many antiligands that is easily attainable using convenient localizing means such as described above may be low in terms of the conductance change it generates, it is actually quite high for many biological molecule preparations encountered, being on the order of $10^{-4}M$ for an antiligand of 100,000 dalton size, as noted above. Many ligands of interest are present at much lower concentrations, e.g. $10^{-8}M$ or lower, in fluid samples of interest, such as serum, urine, etc. Thus all of the ligand in such a one ml sample can be concentrated and bound in a localizing means of 0.1 ul volume that is $10^{-4}M$ in binding site concentration. Using the apparatuses described herein allows the fluid sample to be intimately contacted with a predetermined region containing such localizing means by allowing fluid to flow through the region. This type of apparatus thus provides a potential ligand concentration factor of $$10^{-4}M / 10^{-8}M = 10^4 = 10,000X.$$

Such a concentrating of ligand in the predetermined region is one reason that allows the methods and apparatus of the present invention to achieve considerable sensitivity without requiring a label, and even greater sensitivity with a label.

Referring again to FIG. 5A, there is shown a reservoir 102 filled with an electrolyte solution 100. Two channels 104 and 106 respectively provide paths by which the electrolyte solution can flow from the reservoir, through the test and control predetermined regions 108 and 110, through two exit channels 112 and 114, and eventually to a waste container (not shown). The fluid flow is illustrated by arrows 120. The flow through channels 104 and 106 may be driven by gravity, pneumatic or hydraulic pressure, or other means. If desired, the reservoir may contain a magnetic stirring bar or other means to help achieve homogeneous composition and temperature of the electrolyte. The material from which the reservoir and channels are fashioned is non-conductive.

Measuring means are provided by recessed current and voltage electrodes using the zero-current, four-electrode method noted earlier. A first current electrode 116 in channel 112 and a second current electrode 118 in channel 114 are respectively connected to terminals C1 and C2. A signal generator is connected to terminals C1 and C2 which causes a current to flow from current electrode 116 through channel 112, test predetermined region 108, channel 104, reservoir 102, channel 106, control predetermined region 110, and channel 114, to electrode 118. This current flow causes a voltage drop across test and control predetermined regions 108 and 110 which can be measured to determine the presence of a particular ligand in the electrolyte.

Two voltage electrodes 122 and 124 are connected to terminals V1 and V2 and contact the electrolyte solution on either side of test predetermined region 108. By measuring the voltage between terminals V1 and V2, the conductance of predetermined region 108 may be measured. Similarly, voltage electrodes 126 and 128 are connected to terminals V3 and V4 to provide a means for measuring the voltage drop across control predetermined region 110.

Voltage electrodes 122, 124, 126 and 128 are typically recessed from channels 104, 106, 112 and 114 through which the electrolyte and the electric current flow. Channels 130 in FIG. 5A represent this recession.

Recession reduces errors which are caused by the effects of changing properties of the electrode-electrolyte interface, such as polarization impedance. Polarization impedance may be represented as a variable capacitance and resistance associated with the interface. Voltages developed across this complicated, and often changing, impedance can result in significant errors in the measured value of the potential at the electrode. If the electrode is removed (i.e., recessed) from the electrolyte volume in which all or most of the current flows, little or no current flows near or through this interface. There is thus little or no voltage drop across the interface, and hence little or no effect of changing properties of the interface on the voltage measured by the electrode.

While not wishing to be bound by theory, the following model will be helpful in understanding how voltage electrodes 122 and 124 measure the conductance of test predetermined region 108 and voltage electrodes 126 and 128 measure the conductance of control predetermined region 110.

The voltage electrodes 122, 124, 126, 128 sense a potential approximately equal to that at the mouths of their corresponding recession channels 130. The potential sensed is an average of the potential across the mouth of the recession channel. Typically, this potential may be throught of as that experienced by a point half way across the mouth called the voltage equivalence point; that is the electrode and the voltage equivalence point lie on the same equipotential. Points 131, 133, 135 and 137 represent the voltage equivalence points. Point 131 experiences the same potential as electrode 124, point 133 the same potential as electrode 122, point 135 the same potential as electrode 126, and point 137 the same potential as electrode 128. The corresponding typical equipotentials are indicated by the dotted lines 125, 123, 127 and 129, respectively. Within the volume between equipotentials 123 and 125, a local conductance change typically affects the voltage drop measured by voltage electrodes 122 and 124 strongly, while far outside this volume, such changes tend to have little or no effect. Thus, equipotentials 123 and 125 help to locate test volume 109, the volume whose conductance is measured to determine the occurance of ligand/antiligand interaction in predetermined region 108. Similarly the volume between equipotentials 127 and 129 helps to locate control volume III. As ligand binds to antiligand immobilized in predetermined region 108 and changes the conductance of this region, the conductance of test volume 109 also changes since test volume 109 at least partly includes predetermined region 108.

Current electrodes 116 and 118 are typically recessed down channels 112 and 114 from recession channels 130 that determine the positions of test and control volumes 109 and 111. Such recession reduces errors which are caused by changing current distribution resulting from changes at the surfaces of current electrodes 116 and 118, since it allows the current density to become uniform or nearly uniform by the time it reaches the test and control volumes, irrespective of local variations in current density at the current electrode surface.

For effective recession of both current electrodes and voltage electrodes, the electrode is preferably recessed three or more times the width of the mouth of the recession channel.

The above or equivalent steps potentially give the measuring apparatus high accuracy. Without these steps, an accuracy of 1 part in 10,000 is difficult or impossible to achieve.

That part of the apparatus corresponding to a specific test or control volume is called a "cell". For example, the test cell in FIG. 5A comprises predetermined region 108, contacting channels 104 and 112, voltage electrodes 122 and 124 with their respective recession channels 130, and the corresponding test volume 109. The control cell comprises predetermined region 110, contacting channels 106 and 114, voltage electrodes 126 and 128 with their respective recession channels 130, and the corresponding control volume 111. Current electrodes 116 and 118 and reservoir 102 are common components needed for operation of both the test and control cells in this embodiment.

Optional flow measurement apparatus may be provided to measure the flow of the electrolyte. In FIG. 5A, two hot wire flow sensors 132 and 134 are shown in the exit channels 112 and 114. Circuitry 136 passes a current flow through the sensors and measures the heat conducted away from the sensors by the fluid flow to provide a measurement of the flow rates through test volume 109 and control volume 111. Other means may also be used to determine flow rate. For example, flow meters or fluid resistors 133 and 135 may be placed in exit channels 112 and 114 to regulate fluid flow.

FIG. 5B is a simplified electrical model representative of some of the the electrical characteristics of the arrangement of FIG. 5A. In FIG. 5B, $R_x$ is a resistance representing the resistance of test volume 109. (Either resistance or conductance may be measured as convenient, since each is the reciprocal of the other.) Similarly, $R_c$ represents the resistance of control volume 111. Test resistance $R_x$ includes not only the resistance of test predetermined region 108 but also the resistance associated with those parts of inlet channel 104 and outlet channel 112 that lie between the test region 108 and recession channels 130. Similarly control resistance $R_c$ includes the resistance associated with the entire control volume 111. Clearly, the most efficient sensor of this type will be one in which the resistance of predetermined region 108 is as large a fraction as possible of the resistance of the entire test volume 109, i.e., where the efficiency E, defined as $$E = \frac{\text{Resistance of predetermined region 108}}{\text{Resistance of test volume 109}},$$

approaches 100%.

Resistors R2, R3, R5, and R6 represent the resistance of the electrolyte solution in recession channels 130. Resistors R1 and R7 represent the resistance of the electrolyte solution between current electrodes 116 and 118 and test and control volumes 109 and 111. Resistor R4 represents the resistance between test and control volumes 109 and 111, which includes the resistance of the electrolyte in the reservoir.

It should be appreciated that the model shown in FIG. 5B is only a simplified model. (For example, the polarization impedance associated with each electrode has been omitted. If desired, the polarization impedances may be indicated explicitly by putting an impedance in series with each of resistances R1–R7.) However, this model can be helpful in understanding the electronic circuitry which measures the conductance (or resistance) changes in test and control volumes 109 and 111, a preferred embodiment of which is described in Example 8.

As noted above, the presence of a particular ligand in the electrolyte causes the conductance of the test volume to change. To briefly describe the process by which this is done, test predetermined region 108 contains a matrix which includes immobilized receptors or antiligands for detecting the presence of selected ligands. These antiligands bind the ligand molecules within predetermined region 108 as electrolyte flows through the region. While not wishing to be bound by theory it is believed that as the amount of ligand bound within test predetermined region 108 increases, there is a corresponding decrease in the available volume through which electrical current may flow, resulting in a decrease in the conductance of test predetermined region 108 and hence of the entire test volume 109. Equivalently, there is an increase in the resistance $R_x$ between terminals V1 and V2.

Changes in the conductance of test volume 109 can be used in determining the presence of a ligand in a fluid sample as described in the methods in more detail. Typically, a flow of pure electrolyte solution is established through the test cell until a steady state condition is reached, and the conductance is measured. Preferably, the conductivity of the electrolyte is matched to that of the fluid sample to be examined for presence of ligand. Next, the fluid sample is added to the electrolyte in the reservoir, and the change in conductance with time of test volume 109 is monitored, as is the flow rate. The observed change in conductance is compared with a standard curve such as that of FIG. 1B to determine the concentration of ligand in the fluid sample.

The contacting means may include a sample loop for sample fluid injection instead of a reservoir. In this case a blank solution, or running buffer, of conductivity similar to that of the fluid sample is initially run through the sample loop, inlet channels and predetermined regions via a fluid inlet port. Then using commercially available switching valves in common use (in liquid chromatography, for example, available from Rainin Instruments, Woburn, MA), the fluid sample instead of the blank solution is injected into the fluid inlet port. Ligand-specific changes in conductance can then be monitored either by noting the rate 13 at which conductance changes occur or the magnitude 14 of the total change in conductance after the fluid sample has passed entirely through the sensor. (See FIG. 2B.) Use of valves to regulate entry of fluid sample has an additional potential advantage: such valve technology is highly developed and capable of being automated under computer control. Thus the schedule of sensor exposure to a fluid sample or set of fluid samples can be controlled automatically.

Many factors may affect the resistance between terminals V1 and V2, in addition to the change in conductance of the material in test predetermined region 108. The fluid sample itself may have a conductivity different from that of the running buffer, through preferably its conductivity is adjusted to be similar to that of the running buffer. Small changes in temperature, composition changes due to evaporation, non-specific binding of fluid components to the matrix, etc., can also affect the conductance of the matrix or the conductance of the test volume as a whole.

A second cell, the control cell shown in FIG. 5A is, provided to help correct for these errors. Preferably, its control predetermined region 110, voltage electrodes 126 and 128 and associated channels 130, and inlet and outlet channels 106 and 114 are constructed identically to those of the test cell. Control predetermined region 110 includes matrix material similar to that in test region 108 except that the control cell matrix does not contain antiligand material and is thus substantially free of ligand-specific interactions which effect changes in bulk conductance. By measuring the conductance of test volume 109 relative to the conductance of control volume 111, it is possible to reduce or eliminate variation in conductance from effects other than specific binding of ligand to antiligand sites in test predetermined region 108.

In FIGS. 5A and 5B, the test and control cells are electrically in series via a single current path, through they are hydraulically in a kind of partial parallel, each cell having its own fluid path. However, other electrical configurations can be used to create and then measure a voltage drop across the test and control cells. For example, in FIG. 5C, each cell has its own current path, with the two cells sharing a common current electrode 144. In FIG. 5D, each cell has its own current path, and additionally, each cell has its own pair of current electrodes.

Referring to FIG. 5C, a signal generator is connected to terminals C1 of electrode 140 and C2 of electrode 144 that causes a current to flow through the test cell, from current electrode 140 through channel 112, test predetermined region 108 and test volume 109, channel 104 and reservoir 102 to current electrode 144 in the reservoir. Similarly a signal generator is connected to terminals C1 of electrode 142 and C2 of electrode 144 that causes a current to flow through the control cell, from electrode 142 through channel 114, control predetermined region 110 and control volume 111, channel 106, and reservoir 102, then also to electrode 144. Electrode 144 is thus a common electrode to the two cells. Voltage electrodes 122, 124, 126 and 128 and voltage electrode recession channels 130 function as in FIG. 5A to measure the voltage drop, and hence the resistance, across test volume 109 and control volume 111 generated by the current flow. Circuitry which measures the resistance changes in the test and control volumes of the apparatus in FIG. 5C is described in Example 9.

Referring to FIG. 5D, instead of there being a current electrode in a reservoir common to the test and control cells, each cell has a current electrode in its inlet channel (or in a recession channel that is in electrical contact with its inlet channel) and a current electrode in its outlet channel (or in a recession channel that is in electrical contact with its outlet channel). Specifically, in FIG. 5D the test cell has a current electrode 148 in electrical contact with inlet channel 104 via current electrode recession channel 131 and a current electrode 146 in electrical contact with outlet channel 112 via its corresponding current electrode recession channel 131. Similarly, the control cell has a current electrode 152 in electrical contact with inlet channel 106 and a current electrode 150 in electrical contact with outlet channel 114, also via recession channels 131. A signal generator connected to terminals C1 of electrode 146 and C2 of electrode 148 causes a current to flow from electrode 146 through channel 112, test predetermined region 108 and test volume 109, channel 104, to current electrode 148. Similarly, a signal generator connected to terminals C1 of electrode 150 and C2 of electrode 152 causes a current to flow from electrode 150 through channel 114, control predetermined region 110 and control volume 111, channel 106, to current electrode 152. Voltage electrodes 122, 124, 126 and 128 and voltage electrode recession channels 130 function as in FIG. 5A to measure the voltage drop across test volume 109 and control volume 111 generated by the current flow.

A common fluid source inlet 153 connects to inlet channels 104 and 106 via connecting channels 105 and 107 instead of via a common reservoir. Inlet 153 itself typically connects to a sample loop containing a known amount of fluid sample.

Circuitry which measures the resistance changes in the test and control volumes of the apparatus in FIG. 5D is described in Example 9.

Figure 6A:
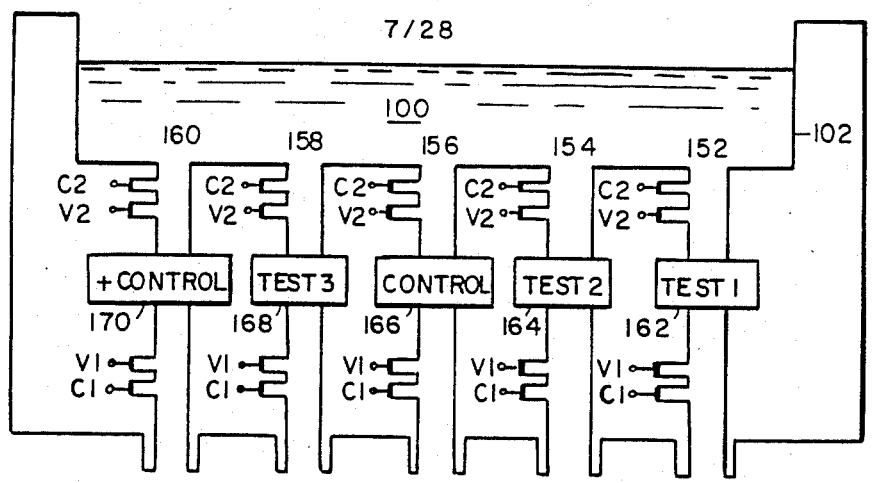
FIG. 6A shows a multiple sensor apparatus with several test cells and a negative and positive control, each cell having its own electric path and fluid path.
Figure 6B:
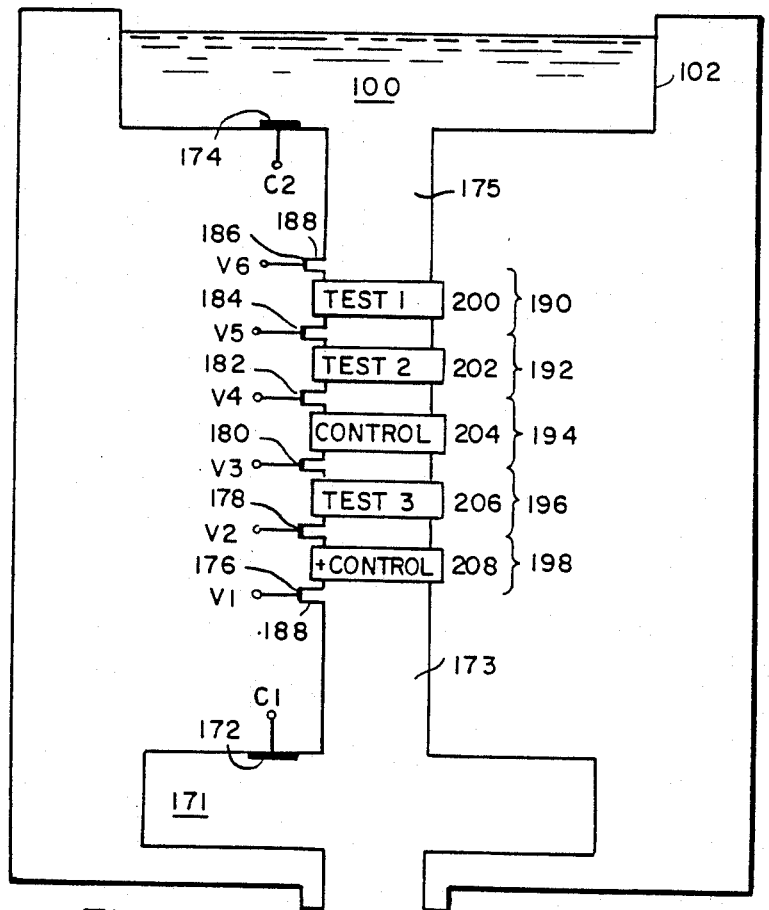
FIG. 6B shows a multiple sensor apparatus with cells in series, all cells sharing a common current path and fluid path.

Referring now to FIG. 6, there is shown a diagrammatic representation of another apparatus used in determining the presence of a ligand in a fluid sample, in which the presence of several different ligands can be determined at once. FIG. 6A illustrates an arrangement with multiple cells in which each cell has its own electric current and fluid path in the manner illustrated in FIG. 5D. FIG. 6B illustrates an arrangement with multiple cells in which cells are connected electrically and hydraulically in series, all cells sharing a common electrical and fluid path.

Referring to FIG. 6A, each of cells 152, 154, 158 and 160 preferably includes a localizing means comprising a matrix with antiligand immobilized on it in the predetermined region 162, 154, 158 or 160 respectively. One cell, e.g. cell 156, typically includes at least part of a predetermined region 166 that does not contain antiligand known to react specifically with any component of the fluid sample to serve as a negative control. Measuring means for each cell comprise two recessed current electrodes connected to terminals C1 and C2 and two recessed voltage electrodes connected to terminals V1 and V2, in the manner illustrated in FIG. 5D. The voltage drop across the test volume of any cell is compared with the voltage drop across that of control cell 156 or any other cell by connecting a signal generator to the current electrodes of the two desired cells to generate an electric current that passes through the cells. Switching means are typically provided to allow rapid comparison of different pairs of cells. Predetermined region 162 of test cell 152, for example, might typically contain antiligand that binds to a first ligand of interest in the fluid sample, while predetermined regions 164 and 168 of test cells 154 and 158 might contain second and third immobilized antiligands that bind to second and third ligands of interest respectively in the fluid sample. Another predetermined region, e.g. region 170 of cell 160, may contain immobilized antiligand that binds to a ligand of known concentration in the fluid sample and may serve as a positive control. An arrangement such as that of FIG. 6A allows simultaneous detection of multiple ligands in a fluid sample and simultaneous comparison of test cells with negative controls, positive controls, or each other.

In a related type of apparatus, each cell has its own fluid path in the manner of FIG. 6A, but it shares a common electrical path with the cell with which it is being compared, in the manner of FIGS. 5A and B. That is, the two cells that are being compared are placed in series with each other, as in FIG. 5B. This is accomplished by connecting a signal generator to the C1 current electrode terminals of the two cells to generate a current that passes through the cells.

Referring to FIG. 6B, there is shown an apparatus in which a series of cells specific for different ligands of interest are connected both electrically and hydraulically in series. Typically, each cell includes a matrix with antiligand immobilized on it in a predetermined region 200, 202, 206, or 208, except again for a negative control cell whose predetermined region 204 does not contain antiligand known to react specifically with any component of the fluid. A common inlet channel 175 and outlet channel 173 to all cells provide paths by which electrolyte solution 100 can flow from common reservoir 102, through the cells and their predetermined regions 200, 202, 206, 204, and 208 and their respective test volumes 190, 192, 196 or control volumes 194, 198 to a waste container (not shown). Measuring means for each cell are provided by two recessed voltage electrodes on either side of each predetermined region, while all cells share two current electrodes 172 and 174. Common first current electrode 172 in or outside channel 173 and common second current electrode 174 in or outside channel 175 are respectively connected to terminals C1 and C2. A signal generator is connected to terminals C1 and C2 which causes current to flow from current electrode 172 into outlet channel 173, through predetermined regions 200, 202, 204, 206 and 208 into inlet channel 175, to current electrode 174. This current flow causes voltage drops across test volumes 190, 192, 196 and control volumes 194, 198 which can be measured to determine the presence of ligands of interest in the electrolyte. Current electrode chamber 171 may be provided to lower the polarization impedance of current electrode 172.

The above arrangement provides for the same electrical current and the same fluid current to flow through all cells. This can help simplify the design of the electrical instrumentation and of the fluid flow measuring apparatus. (In fact, since signal development will start in different sensors at different times, observation of such timing differences can itself be used to measure flow rate.) However, the series approach typically increases the total pressure needed to cause fluid to flow at a given rate. Which considerations predominate depends on the conditions required for a particular experiment.

Voltage electrodes 176, 178, 180, 182, 184 and 186 are connected to terminals V1–V6 respectively and contact the electrolyte on either side of predetermined regions 200, 202, 204, 206 and 208. By measuring the voltage between any two adjacent voltage electrode terminals $V_n$ and $V_{n+1}$ the conductance of the predetermined region and the test or control volume included between the corresponding voltage electrodes may be measured. As in previous arrangements, voltage electrodes 176, 178, 180, 182, 184 and 186 are typically recessed from channels 173 and 175 where electrolyte and electric current flow via voltage electrode recession channels 188. The midpoints of the mouths of adjacent recession channels 188 typically define the positions of test volumes 190, 192, 196 and control volumes 194, 198 included between adjacent recession channels. Also, current electrodes 172 and 174 are typically recessed down channels 173 and 175 from the test volumes.

As with the apparatus of FIG. 6A, the predetermined regions 200, 202, 204, 206, 208 of the apparatus in FIB. 6B typically contain antiligands to several different ligands of interest in a fluid sample, as well as positive and negative controls.

Groups of cells in series, of the type shown in FIG. 6B, can themselves be placed so that each group of cells has its own electric current and fluid path in the manner illustrated in FIG. 6A to increase the overall number of test volumes that can be monitored simultaneously.

An arrangement of cells connected in series can be made thinner than that shown in FIG. 6B by connecting in series (hydraulically as well as electrically) several cells modified from the type shown in FIG. 5A, where the reservoir is replaced by a channel, and the fluid outlet of one cell connects to a fluid inlet of the next. This allows each voltage electrode to be on one of two levels, no matter how many cells there are in the series, with fluid and electric current weaving back and forth between the two levels.

Figure 7A:
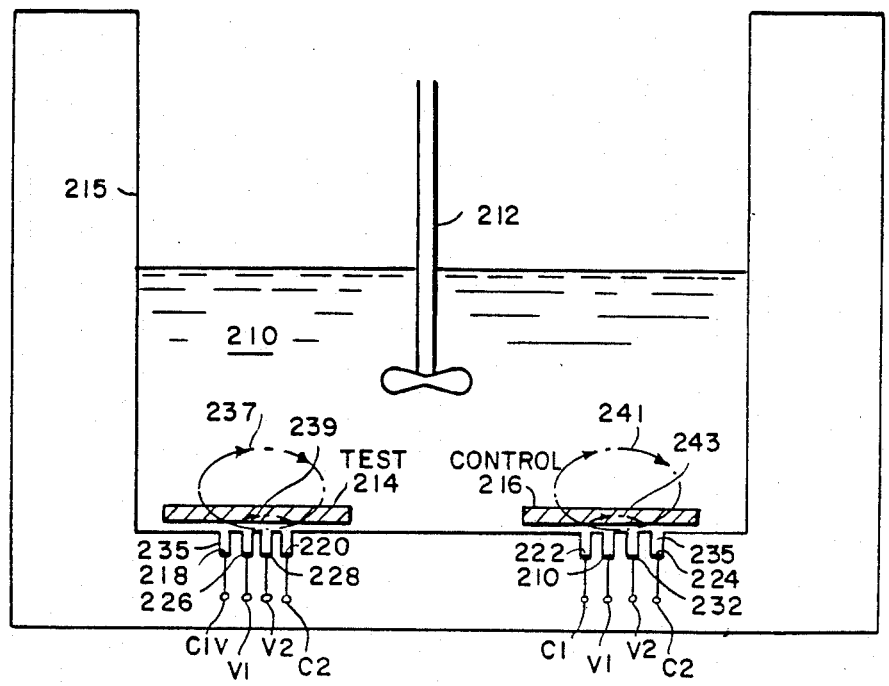
FIG. 7 shows two versions of a recessed planar sensor and apparatus.
Figure 7B:
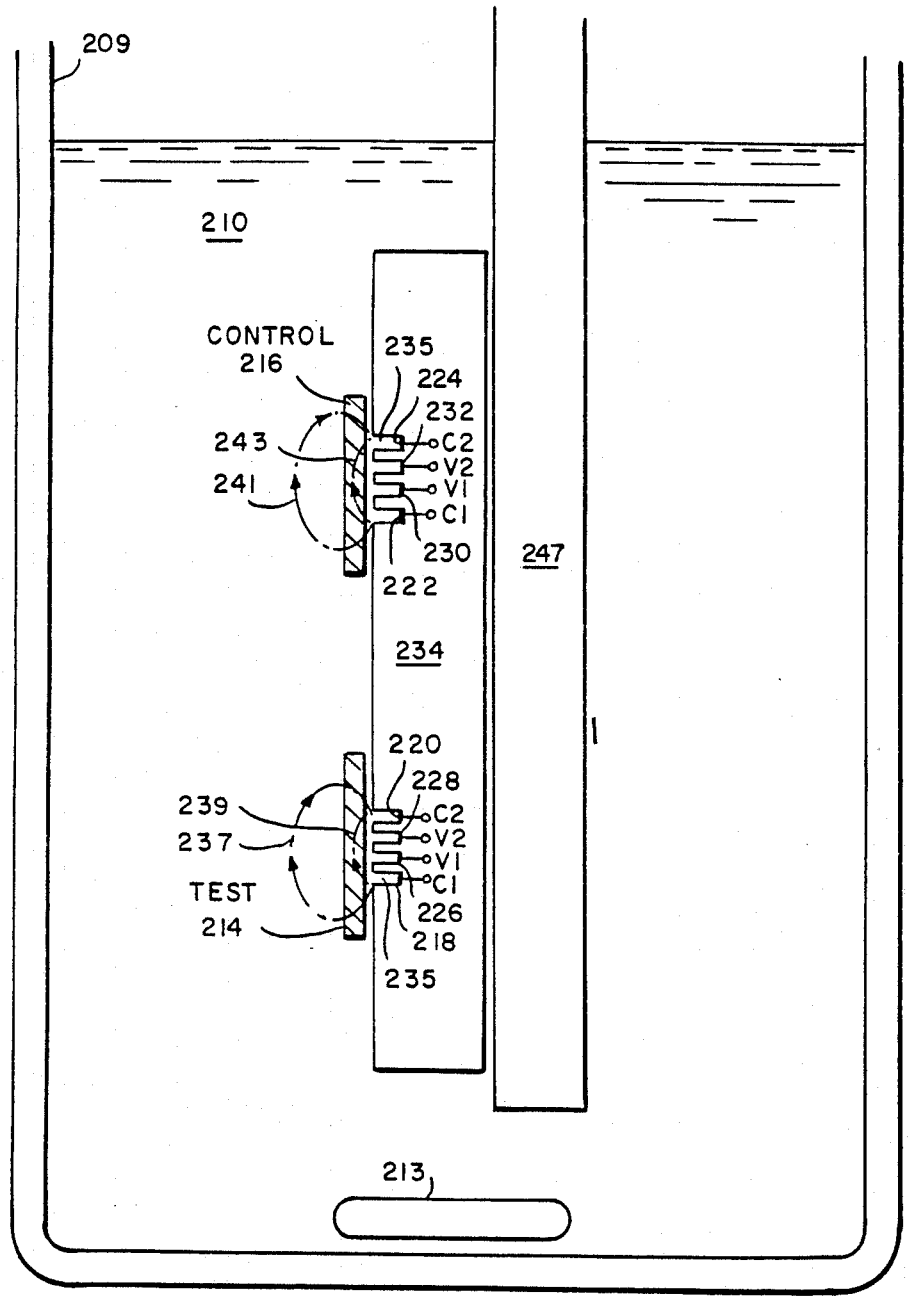

Referring now to FIG. 7, there is shown yet another apparatus used in determining the presence of a ligand in a fluid sample by measuring the change in bulk conductance of a test volume as ligand interacts with antiligand localized in a predetermined region that is at least partly within the test volume. In this embodiment, the measuring means lie in a plane, on the same side of the localizing means. In FIG. 7A, there is shown an arrangement where the localizing and measuring means lie in the bottom of a well that contains electrolyte. In FIG. 7B there is shown a similar arrangement, except that the localizing and measuring means are mounted on a support fixture that dips into a well, test tube, or other space that contains electrolyte. The arrangement of FIG. 7A allows easy injection of a fluid sample onto sensors. The arrangement of FIG. 7B allows easy insertion of sensors into a fluid sample.

Referring to FIG. 7A, there is shown (not to scale) a well 215 constructed from non-conducting material filled with electrolyte 210. Test predetermined region 214 and control predetermined region 216 lie on the bottom of the well. Preferably, test predetermined region 214 contains localizing means comprising a matrix that has immobilized on it antiligand which interacts with the ligand of interest or localizing means comprising a semipermeable membrane which encloses such antiligand. Control predetermined region 216 is constructed similarly to test predetermined region 214 but does not contain such antiligand and is substantially free of specific interactions which cause changes in bulk conductance. Ligand enters predetermined regions 214 and 216 by diffusion. Stirring propeller 212 or other means of causing bulk fluid flow is used if desired to aid contact between the fluid and the predetermined regions.

Measuring means for the test cell are provided by current electrodes 218 and 220 connected to terminals C1 and C2 and voltage electrodes 226 and 228 connected to terminals V1 and V2. Measuring means for the control cell are provided by current electrodes 222 and 224 connected to terminals C1 and C2 and voltage electrodes 230 and 232 connected to terminals V1 and V2. The measuring means lie in the bottom 211 of well 215 in non-conducting material 234, beneath predetermined regions 214 and 216.

To measure the conductance of the test cell, a signal generator is connected to terminals C1 and C2 of electrodes 218 and 220, causing a current to flow from electrode 218, through test predetermined region 214, into electrolyte 210, back through predetermined region 214, to electrode 220. Such a current path is illustrated by the dotted line and arrows 237. Also, some current remains entirely within predetermined region 214. Such a current path is illustrated by the dotted line and arrow 239. The current flow is correlated with a voltage drop along the current paths. Since at least part of each current path passes through test predetermined region 214, at least part of the voltage drop will be influenced by the conductance of this region. By measuring the voltage between terminals V1 and V2 connected to electrodes 226 and 228, the conductance of test predetermined region 214 may be measured.

Similarly to measure the conductance of the control cell, a signal generator is connected to terminals C1 and C2 of electrodes 222 and 224, causing a current to flow from electrode 222, through control predetermined region 216, into electrolyte 210, back through region 216, to electrode 224, as illustrated by the dotted line and arrows 241. Also, some current remains entirely within control localizing means 216, as illustrated by the dotted line and arrow 243. The current flow is correlated with a voltage drop along the current paths. By measuring the voltage drop between terminals V1 and V2 connected to electrodes 230 and 232, the conductance of control predetermined region 216 may be measured.

Preferably, as in other embodiments, the voltage electrodes and current electrodes are recessed. For example, as illustrated in FIG. 7A, the electrodes are recessed down channels 235 a distance three or more times the width of the channels.

Current flow is densest in a volume whose radius is of the order of the distance between the current electrodes. For a cell with a configuration such as that in FIG. 7A, the test volume may be thought of as extending out above the bottom of the well about this distance or a little more, i.e., the effective cell size may be thought of as being on the order of the distance between the current electrodes. As a useful illustration, the test volume may be thought of as being the volume within the dotted field line 237, and the control volume may be thought of as being the volume within the dotted field line 241; that is, voltage electrodes 226, 228, 230 and 232 will typically sense weakly or not at all conductance changes that occur outside this region.

The efficiency of a planar recessed cell, as for cells previously discussed, can be defined as $$E = \frac{\text{Resistance of predetermined region}}{\text{Resistance of test volume}}.$$

Typically, if the thickness of the predetermined region is of the order of the cell size, the cell will be efficient. On the other hand, if the predetermined region is thicker than about 0.1 mm, diffusion becomes very slow. Thus, in order to construct sensors that are efficient and that also respond quickly to the presence of ligand, both the test volume and predetermined region volume should be small, e.g., $\leq 0.5$ mm thick for the test volume and $\leq 0.1$ mm thick for the predetermined region. Typically this requires the construction of closely spaced current and voltage electrodes, which can be done in a variety of ways, including thick film processes, thin film processes and silicon chip technologies.

Changes in the conductance of test volume 214 are compared, e.g. ratiometrically, to changes in the conductance of control volume 216 and the changing conductance ratio C is used to determine the presence and concentration of a ligand in a fluid sample. Typically, pure electrolyte is injected into well 215 and stirred until the conductance ratio C becomes steady. Preferably the conductivity of electrolyte 210 is matched to that of the fluid sample to be examined for the presence of ligand. Next, the fluid sample is added to electrolye 210 in well 215, and the change in the conductance ratio C with time is monitored.

The change in the conductance ratio observed during a particular experiment typically depends on a variety of factors, such as thickness of the predetermined regions, affinity of antiligand for ligand, diffusion constant of the ligand, concentration of ligand, etc. Therefore, a standard curve for the ligand of interest is constructed under known experimental conditions. The observed change in conductance ratio, developed under the same conditions, is compared with the standard curve to determine the concentration of ligand in the fluid sample.

The matrix of predetermined regions 214 and 216 will exclude particles larger than the pore size of the matrix. This may aid in measurement of fluid samples with a large burden of unwanted particles even if such particles can enter test volume 237 and control volume 241, e.g. if stirring keeps the particles homogenously distributed. Predetermined regions 214 and 216 can themselves be made to exclude particles from volume 237 and 241 if they are much thicker than these volumes. Alternatively, a layer or layers can be laid over predetermined regions 214 and 216. If this layer is impermeable to particles present in the electrolyte, and if the combined thickness of the predetermined region and this layer is greater than that of the test and control volumes, then this layer will exclude particles from the test volume, as noted earlier. The above devices and variations on them can be useful to allow measurement of ligand presence in fluids containing particles that would otherwise cause noise in the measurement. Planar recessed cells such as those in the apparatus of FIG. 7A can be used to measure the specific binding of particle/ligand complexes to the surface (or interior) of a predetermined region 214. In this situation, the test volume is deliberately kept larger than the thickness of predetermined region 214 so as to include the surface of the region. The test volume then extends into the space above the surface of the region. As particle/ligand complexes bind to antiligand on the surface of predetermined region 214, they occupy part of test volume 237 above the surface, thus decreasing the conductance of the test volume. A similar arrangement is used to measure the specific binding of cells, vesicles, membrane fragments or other structures that carry particular ligands on their surfaces and hence to determine their presence and concentration in a fluid sample.

In order to increase the efficiency of a recessed planar sensor whose test volume is much larger than its predetermined region, an opposing wall of non-conducting material is brought near the surface of the predetermined region to confine the electric field, thus reducing the test volume. Alternatively, a modulating layer, permeable to ligand but whose conductivity is lower than that of the predetermined region, such as porous polycarbonate filter from Nuclepore (Pleasanton, CA), may be laid over the predetermined region. This will tend to confine the electric field so that the current density in that part of the predetermined region next to the modulating layer will be increased. The voltage drop occurring in this part of the predetermined region will also increase, thus increasing the efficiency of the sensor.

Referring to FIG. 7B, there is shown (not to scale) a test tube or other fluid-containing space 209 that holds electrolyte 210. The sensors in this arrangement are formally identical to those of FIG. 7A, as shown by identical numbering of corresponding elements; only the contacting means differ.

Localizing means comprising a matrix define the location of test predetermined region 214 and control predetermined region 216 as in FIG. 7A. Regions 214 and 216 are mounted on a non-conducting layer 234 that itself may be mounted on a support fixture 247. This apparatus is designed to allow easy insertion of sensors into the fluid 210.

Measuring means underlie the localizing means in predetermined regions 214 and 216. Stirring bar 213 or other means of causing bulk fluid flow is used if desired to aid contact between the fluid 210 and the surfaces of predetermined regions 214 and 216.

A variety of structures, or biolayers, can be used to fix a set of localizing means firmly and conveniently in position over the measuring means. This allows one to take a measurement, then remove the used localizing means and fix a new set in place while using the same measuring means. For example, the localizing means may be mounted on a holder that fits over block 234. Other biolayer variations are discussed herein below.

Multiple test cells and positive as well as negative control cells may be placed in wells such as those of FIG. 7A or on dip-in sensors such as those of FIG. 7B. To avoid interference between cells, neighboring cells should be far apart from each other; that is, the distance between them should be considerably greater than the distance between the current electrodes of a single cell. Thus, recessed planar sensors of this type can be fashioned into microtiter plates or dip-in probes wherein several assays are performed in each well or on each probe. Probes can also be fashioned into sensors for indwelling catheters, or the sensors can lie on the surface or inside of a channel through which fluid sample flows.

A practical test apparatus and instrument should be capable of performing successive tests on various solutions quickly and inexpensively. Preferably the predetermined regions in the test and control cells should be easy to replace. Also, as discussed earlier, each sensor preferably has a small predetermined region, e.g., less than 1 ul or even less than 0.1 ul, to allow increased sensitivity. Further, the efficiency E of the sensor preferably is high, even when the predetermined region is small.

Figure 8A:
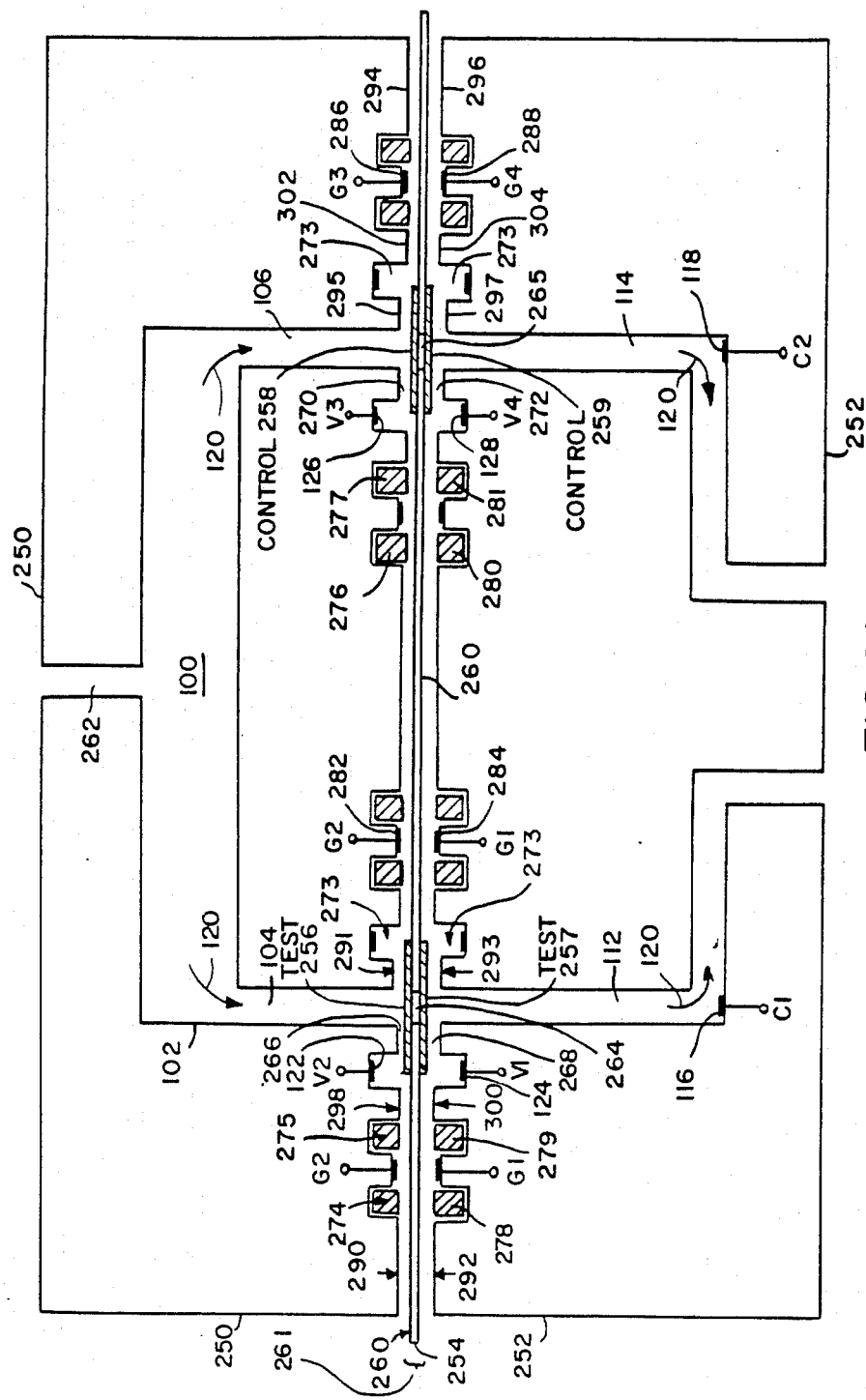
FIG. 8A shows a section of the measuring means in an IVEP sensor (see definitions) with the biolayer inserted in the sensor.
Figure 8B:
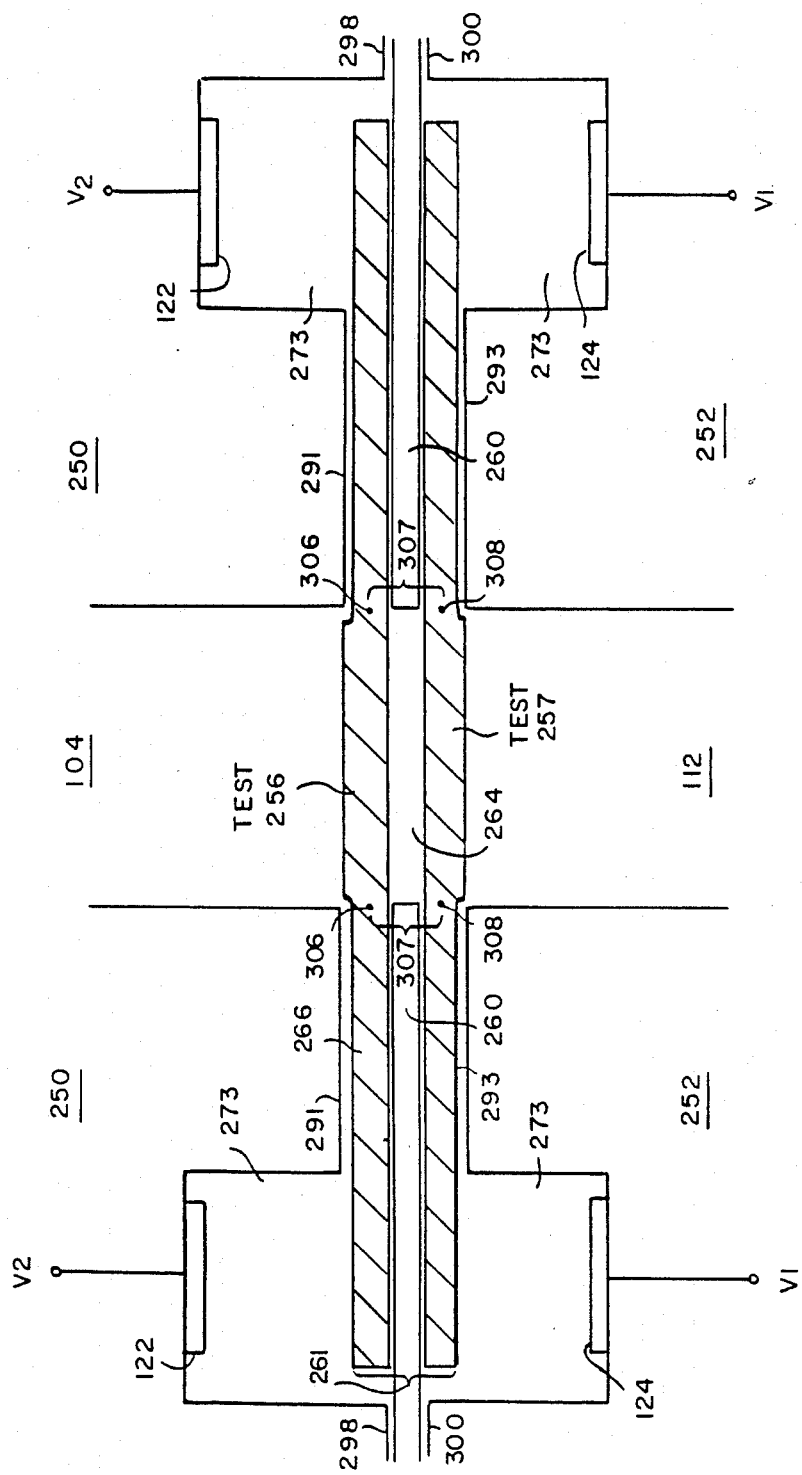
FIG. 8B shows a close-up of the sensing region in the IVEP sensor.
Figure 9A:
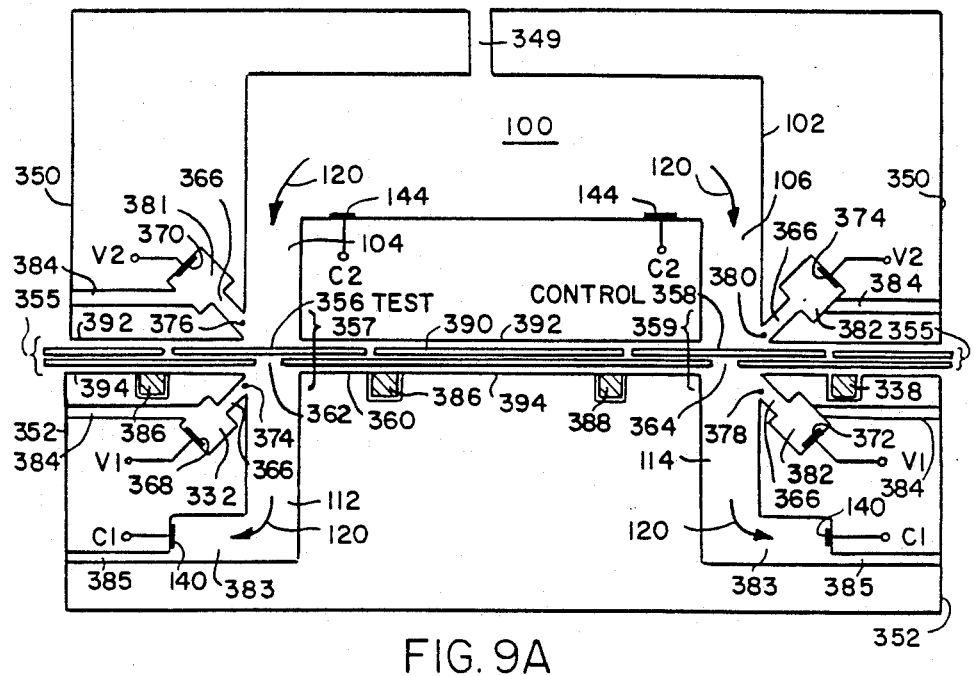
FIG. 9A shows a section through the measuring means of an EVEP sensor (see definitions)

Two preferred configurations that allow the above features are illustrated (not to scale) in FIGS. 8 and 9. The apparatus shown in FIG. 8, called in "IVEP" (Internal Voltage Equivalence Point) sensor apparatus, allows accurate measurement of the conductance of very thin, layer-like predetermined regions (FIG. 8A, 256–259) and test volumes (FIG. 8B, 307), on the order of 0.1 mm thick and 0.1 ul in volume, or even less. The apparatus shown in FIG. 9A, called an "EVEP" (External Voltage Equivalence Point) sensor apparatus, allows convenient measurement of events occurring near as well as in the predetermined regions, and has a potentially very simple biolayer.

Referring to FIG. 8A, there is shown an IVEP sensor apparatus comprising a front section 250 and a rear section 252 made of non-conducting material such as acrylic plastic. Sections 250 and 252 may be separated along a plane designated by mid-line 254. A middle layer 261, called the biolayer, consists of test predetermined regions 256 and 257 and control cell predetermined regions 258 and 259 mounted on insulating layer 260. Biolayer 261 is inserted between front and rear sections 250 and 252 during operation of the apparatus. Localizing means preferably comprise matrix material consisting of a thin porous layer of nitrocellulose or other porous filter material, which defines predetermined regions 256–259. The predetermined regions of the biolayer are called bioregions. Preferably, the insulating layer itself is mounted on a rigid support (not shown) to aid in handling and positioning of the biolayer.

FIG. 8A shows the IVEP sensor in its "open position", with front and rear sensor blocks 250 and 252 separated enough (typically about 1/16 inch) to allow easy insertion of biolayer 261. FIG. 8B shows detail of the sensing region of the test cell, with sensor blocks 250 and 252 closed over biolayer 261, squeezing upper and lower bioregions 256 and 257 in channels 266 and 268 formed between surface 291 of front sensor block 250, insulating layer 260, and surface 293 of rear sensor block 252.

The apparatus of FIG. 8A operates in a manner similar to that of FIG. 5A. (However, it should be noted that an IVEP sensor apparatus could be made equally well with the arrangements of FIG. 5C or 5D.) Test and control cells are connected in series and the test and control cell paths are symmetrical. Referring to FIG. 8A, reservoir 102 is filled with electrolyte solution 100. Two channels 104 and 106 provide paths by which electrolyte solution 100 can flow from reservoir 102, through test predetermined regions 256 and 257 and control predetermined regions 258 and 259, through two exit channels 112 and 114, and eventually to a waste container (not shown). The fluid flow is indicated by arrows 120. The flow may be driven by gravity, pneumatic or hydraulic pressure, or other means.

For the test cell, fluid travels from fluid inlet port 262 and reservoir 102 through channel 104, upper test bioregion 256, opening 264 provided in insulating layer 260, lower test bioregion 257, and then exists through channel 112. For the control cell, fluid travels from fluid inlet port 262 and reservoir 102 through channel 106, upper control bioregion 258, opening 265 provided in insulating layer 260, lower control bioregion 259, and then exits through channel 114.

The measuring means comprise recessed voltage and current electrodes. A first current electrode 116 in channel 112 and a second current electrode 118 in channel 114 are respectively connected to terminals C1 and C2. A signal generator is connected to terminals C1 and C2 and causes a current to flow from current electrode 116 through channel 112, lower test bioregion 257, opening 264, upper test bioregion 256, channel 104, reservoir 100, channel 106, upper control bioregion 258, opening 265, lower bioregion 259, and channel 114 to electrode 118. This current flow causes a voltage drop between the top and bottom bioregions of each cell which can be measured to determined the presence of a particular ligand in the electrolyte.

Two fluid channels 266 and 268 above and below the insulating layer 260 are filled with electrolyte. This may conveniently be done by keeping both sensor blocks 250 and 252 submerged in an electrolyte bath (see FIG. 9B). Channels 266 and 268 are equivalent to recession channels 130 shown in FIG. 5A. As shown clearly in FIG. 8B, recession channel 266 provides an electrical connection between the flowing electrolyte and voltage electrode 122 connected to terminal V2. Recession channel 268 provides an electrical connection between the electrolyte and voltage electrode 124 connected to terminal V1. The control cell operates similarly, with recession channels 270 and 272 respectively providing electrical paths between the electrolyte and voltage electrodes 126 and 128 connected to terminals V3 and V4. O-rings 274 through 281 provide sealing to isolate the fluids in the test and control cells and prevent electrical leakage. Surfaces 290, 292, 294 and 296 determine the dimensions of the cells by butting against insulating layer 260. Surfaces 298, 300, 302 and 304 may also serve this function. All recession channels, voltage electrodes, and O-rings are circular and symmetrical about the inlet and outlet channels 104 and 112 (for the test cell) and 106 and 114 (for the control cell). Voltage electrodes 122, 124, 126 and 128 are further recessed by being placed in recession chambers 273 connected to recession channels 266, 268, 270 and 272, which allows the electrodes to be large and have low polarization impedance.

In operation, the structure of FIG. 8A is opened along mid-line 254, and a new biolayer 261 is inserted with fresh test and control cell bioregions. Front and rear sections 250 and 252 are then reassembled, with O-rings 274–281 providing sealing of each cell. This three-part structure allows easy and inexpensive replacement of biolayers.

The sealing provided by the O-rings may not be perfect, however, and seepage of electrolyte past the O-rings may occur. Referring to FIG. 8A, if there is seepage past O-rings 274, 275, 276 and 277, for example, a conductive path between the test and control cells may result in errors in the measurements of the cell conductances. To reduce or eliminate errors caused by such seepage, guard electrodes 282, 284, 286 and 288 connected to terminals G1 through G4 are provided if desired between each of the voltage measurement terminals V1–V4 and its adjoining O-ring seals. The operation of these guard rings is discussed in more detail in Examples 8 and 9.

Referring again to FIG. 8B, there is shown the sensing region of the test cell in closeup, with the IVEP sensor apparatus in the closed position. The bioregion matrix material of test predetermined regions 256 and 257 fills recession channels 266 and 268 respectively. Similarly, though not shown here, the bioregion matrix material of control predetermined regions 258 and 259 fills recession channels 270 and 272. This is achieved by making sure that the surfaces 291, 293, 295 and 297 that form recession channels 266, 268, 270 and 272 lie a distance below coplanar surfaces 290, 292, 294, 296, 298, 300, 302 and 304 (FIG. 8A) that is less than the thickness of the particular biolayers used. With bioregions 0.125–0.150 mm thick, this distance is typically 0.1 mm. Filling recession channels 266, 268, 270, 272 with matrix material minimizes noise and drift due to bubble formation and convection of fluid from the recession channels into the test volume. This also helps ensure that the channels remain conducting and are not blocked, e.g., by bubbles, even if they are very shallow.

Referring again to FIG. 8B, the structure of the IVEP apparatus allows the voltages sensed by voltage electrodes 122 and 124 at the mouths of recession channels 266 and 268 to lie not only near, but actually inside test predetermined regions 256 and 257, as shown by voltage equivalence points 306 and 308; hence the term "Internal Voltage Equivalence Point", or "IVEP" sensor. Voltage equivalence points 306 and 308 help locate test volume 307 whose conductance is measured to determine the occurrence of ligand/antigand interaction in predetermined regions 256 and 257. In this simple model, test volume 307 may be thought of as typically comprising half the thickness of top recession channel 266 plus the thickness of insulating layer 260 plus half the thickness of bottom recession channel 268. Similarly, for the control cell, the voltage sensed by the voltage electrodes 126 and 128 at the mouths of recession channels 270 and 272 (FIG. 8A), allows the voltage equivalence points for the control sensor to lie inside control predetermined regions 258 and 259, defining a corresponding test volume (not shown) that comprises half the thickness of top recession channel 270, plus the thickness of insulating layer 260, plus half the thickness of bottom recession channel 272.

The IVEP sensor apparatus shows that the location and size of the voltage electrodes can be effectively decoupled from those of the volume whose conductance they are measuring through the use of recession chambers and channels. The flexibility in sensor design thus gained is an important advantage of the present invention.

Again referring to FIG. 8A, the ability to construct a thin test volume can be seen to be limited only by the availability of thin matrix materials for the predetermined regions 256–259, a thin insulating layer material 260, and the accuracy of techniques available to place the surfaces 291, 293, 295 and 297 that form recession channels 266, 268, 270 and 272 a small distance below surfaces 290, 292, 294, 296, 298, 300, 302 and 304.

As noted earlier, a thin test volume allows test and control volumes to be very small, which is an important advantage of this IVEP embodiment. Typically test volumes are constructed using nitrocellulose matrix material from Millipore Corp. (Bedford, MA) that is 135–150 micrometers thick, recession channels 100 micrometers thick, and insulating layer of lexan from General Electric (Schenectady N.Y.) 75 micrometers thick, and an opening in the insulating layer 0.8 mm in diameter. This yields a distance between the voltage equivalence points of one half the thickness of the top recession channel plus the thickness of the insulating layer, plus one half the thickness of the bottom recession channel, or 175 micrometers total. Since the area of the opening is about 0.5 mm$^2$, an estimated size for the test volumes is 0.09 microliters.

Even smaller test volumes can be constructed. As an example, a matrix that is approximately 25 or 30 micrometers thick and recession channels that are 25 micrometers thick can be used along with an insulating layer that is approximately 25 micrometers thick. Also if a half millimeter diameter hole in the insulating layer of the biolayer is used, its area will be 3/16 sq. millimeter. The distance between voltage equivalence points is a total of 0.05 millimeters. Thus the total test volume would be about 9 nanoliters or 0.009 microliters.

Sensors with even smaller dimensions can be built up using thin layers of insulating material of appropriate thickness and instrument grade machining techniques, injection molded parts, thick film or thin film techniques, silicon chip technology, or other techniques known to those skilled in the art. Using such techniques it is possible to construct IVEP sensors where the width of the opening of the recession channels ranges from 10 micrometers to about 5 micrometers or even smaller and where these openings are 10 micrometers apart with respect to each other or less, yielding an even smaller test volume.

Biolayer 261 can be varied in many ways. For example either the top or bottom predetermined region 256 or 257 may be eliminated, with substitution of a matrix that does not localize antiligands or of no matrix at all. Opening 264 in the insulating layer may be substantially completely filled with localizing means matrix by compression or by casting nitrocellulose or other matrix material directly in the opening. Filling opening 264 with localizing means matrix allows construction of a sensor with nearly 100% efficiency, in which substantially all the test volume contains localizing means. Also, in such a sensor, substantially all of the test volume is included within the localizing means.

Referring to FIG. 9A, there is shown a typical EVEP sensor apparatus consisting in part of front section 350 and rear section 352 which are made of non-conducting material such as acrylic plastic and which may be separated along a plane designated by mid-line 354. A middle layer, biolayer 355, comprises test predetermined region 356 and control predetermined region 358 mounted if desired on an insulating backing 360 for convenience in handling. Biolayer 355 is inserted between front and rear sections 350 and 352.

In this embodiment, the localizing means typically comprise a matrix material consisting of a thin porous layer of nitrocellulose or other porous filter material, which define predetermined regions 356 and 358.

The apparatus of FIG. 9A operates in a manner similar to the apparatus of FIG. 5C. (However, it should be noted that the EVEP sensor apparatus can be made equally well with arrangements such as those of FIG. 5A or 5D or in a series flow configuration such as that of FIG. 6B). A test cell and a control cell each has its own current path with the two cells sharing a common current electrode, and the test and control cell paths are symmetrical. Referring to FIG. 9A, reservoir 102 is filled with an electrolyte solution 100 via fluid inlet port 349. Two channels 104 and 106 respectively provide paths by which the electrolyte solution flows from reservoir 102, through test predetermined region 356 and control predetermined region 358, through two exit channels 112 and 114, and eventually to a waste container (not shown). The fluid flow is indicated by arrows 120. The flow may be driven by gravity, pneumatic or hydraulic pressure, or other means.

For the test cell, fluid travels from reservoir 102 through channel 104, through predetermined region 356, through opening 362 in insulating layer 360 of biolayer 355, and then exits through channel 112. Similarly, for the control cell, fluid travels from reservoir 102 through channel 106, through control predetermined region 358, through opening 364 in insulating layer 360 of biolayer 355, and then exits through channel 114.

The measuring means comprise recessed voltage and current electrodes. A signal generator is connected to terminals C1 of electrode 140 and C2 of ring-shaped or arc-shaped electrode 144 that causes a current to flow from electrode 140 through channel 112, opening 362, test predetermined region 356, channel 104 and reservoir 100, to electrode 144. Similarly, a signal generator is connected to terminals C1 of electrode 142 and C2 of electrode 144 that causes a current to flow from electrode 142, through channel 114, opening 364, control predetermined region 358, channel 106 and reservoir 102, then also to electrode 144. Electrode 144 thus is a common electrode to the two cells. The current flows cause voltage drops across the predetermined regions and test volumes (see below) of each cell which can be measured to determine the presence of a particular ligand in the electrolyte.

Fluid channels 366 are filled with electrolyte and provide electrical paths to recessed voltage electrodes 368, 370, 372 and 374. These channels are equivalent to voltage electrode recession channels 130 shown in FIG. 5A and the similar channels shown in FIG. 5C. Points 374 and 376 in channels 366 are the voltage equivalence points of the test cell, and points 378 and 380 are the voltage equivalence points of the control cell. These help define the position of test volume 357 and control volume 359 whose conductance will be measured. Voltage electrodes 368 and 370 connected to terminals V1 and V2 measure the voltage drop between voltage equivalence points 374 and 376. It should be noted that in the EVEP configuration, the test volume between voltage equivalence points 374 and 376, and hence typically the test volume 357, entirely includes predetermined region 356. Similarly, voltage electrodes 372 and 374 connected to terminals V1 and V2 measure the voltage drop between voltage equivalence points 378 and 380 which help define control volume 359.

Voltage electrode recession chambers 382 recess the voltage electrodes even more, and allow them to be large, reducing their polarization impedance. Current electrode recession chambers 383 act similarly for the current electrodes. Fluid outlets 384 from voltage electrode recession chambers 382 allow flushing of the chambers with electrolyte if desired, while fluid outlets 385 from the current electrode chambers allow removal of electrolyte to waste containers.

Additionally or as an alternative to the voltage electrode recession chamber outlets 384, recession channels 366 are filled with a conducting matrix such as porous paper or a gel to reduce noise due to bubbles or to entry of contents of chambers 382 into test and control volumes 357 and 359, e.g., by convection. Likewise, fluid inlet and outlet channels 104, 106, 112 and 114 may contain a porous matrix for similar reasons as long as this does not interfere unacceptably with fluid flow.

The voltage equivalence points in the apparatus configuration of FIG. 9A are outside predetermined regions 356 and 358; thus the name External Voltage Equivalence Point (EVEP) sensor.

O-rings 386 and 388 provide sealing to isolate the fluids in the test and control cells and prevent electrical leakage.

The biolayer configuration allows easy handling and positioning of the matrices defining predetermined regions 356 and 358. Biolayer 355 comprises predetermined regions 356 and 358 and spacing layer 390 mounted on insulating backing layer 360. Spacing layer 390 is slightly thinner (typically on the order of 0.1 mm) than predetermined regions 356 and 358 (typically on the order of 0.135 to 0.150 mm) so that biolayer 355 will be held firmly when the sensor is closed. Spacing layer 390 and insulating layer 360 are squeezed between surfaces 392 and 394 to seal the O-rings and determine the dimensions of the test and control cells.

Figure 9B:
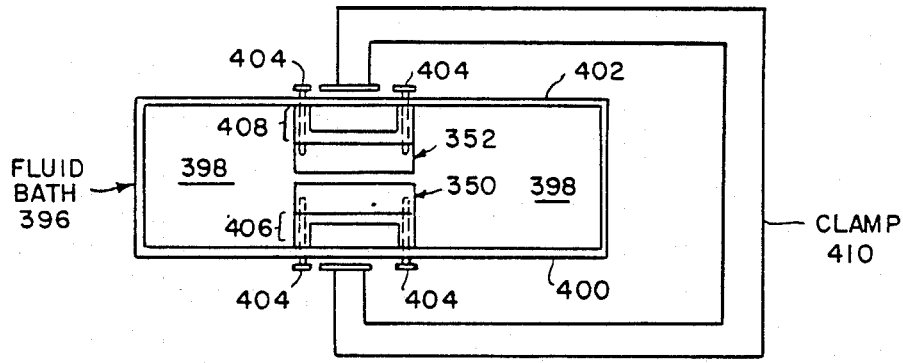
FIG. 9B shows a water bath for use with an IVEP or EVEP sensor.

FIG. 9B depicts a fluid bath which can be used for either the IVEP or the EVEP sensor to maintain temperature equilibrium of the test and control cells, to wet the biolayer as it is inserted, and to keep the channels of the sensor filled with fluid. More specifically, there is shown a top view of fluid bath 396 containing electrolyte 398. Typically, the front 350 and rear 352 blocks of an EVEP sensor are mounted in flexible walls 400 and 402 of fluid bath 396 using screws 404 and mounting pieces 406 and 408 or other means. The blocks are at a height that leaves the measuring means (not shown) in the blocks submerged at all times so that when biolayers are inserted or removed, the channels of the sensor remain filled with fluid. As noted above, the fluid bath helps maintain temperature equilibrium of the test and control cells and wets the biolayer as it is inserted. Mounting pieces 406 and 408 also help maintain temperature equilibrium by keeping sensor blocks 350 and 352 away from walls 402 and 404 of the bath. In general, no additional temperature regulation is needed, even for conductance measurements sensitive to 100 parts per million or better.

The arrangement of FIG. 9B holds sensor blocks 350 and 352 firmly and allows convenient insertion of biolayers. After a biolayer has been inserted, clamp 410 or other means squeezes together the walls of the bath, and hence squeezes the biolayer between sensor blocks 350 and 352, isolating the test and control cells from each other electrically and hydraulically via the action of the O-rings noted supra.

The EVEP type of sensor can be modified in a variety of ways. A sample loop system may be used for fluid sample injection, with or without a reservoir. If desired, opening 362 in insulating layer 390 may, as shown in FIG. 9A, be made smaller than the diameters of channels 104, 106, 112 and 114. This has the effect of increasing the relative contribution to the total resistance (between the voltage equivalence points) of the region in the immediate vicinity of opening 362—a partial Jones cell-type effect. Most of the resistance associated with the constricted opening occurs within a volume associated with the opening itself and the region on either side of the opening within one diameter's distance. This approach can improve the efficiency of even an inefficient EVEP sensor to 30% to 50% if the thickness of predetermined region 356 is comparable to or greater than both the thickness of insulating layer 360 and the diameter of opening 362, i.e., even if the voltage equivalence points 374, 376, 378 and 380 are far away.

Another way to increase the efficiency of an EVEP sensor configuration is to bring voltage equivalence points 374, 376, 378, 380 closer to their predetermined regions by inserting hollow tubular sheaths down the inlet and outlet ports of the contacting means, partially blocking recession channels 366 to the voltage electrodes and pushing the voltage equivalence points nearer to the biolayer. An experiment using this "sheathed column" configuration of the EVEP sensor is shown in Example 3.

The efficiency of the EVEP, IVEP and other embodiments can be increased by placing a current modulating material near a localizing means, wherein this material has a cross-sectional conducting area less than the cross-sectional conducting area associated with the localizing means. An example of such a material is Nuclepore filter, a radiation-exposed, alkali digested porous polycarbonate available commercially from Nuclepore Corporation (Pleasanton, CA). This material consists of 90% non-conducting solid and 10% conducting pores. It may be thought of as creating a microporous, partial Jones cell effect similar to effect of constricting opening 362 in insulating layer 390. Since electric current must be concentrated in the modulating material to pass through a conducting area less than that associated with the localizing means, a larger voltage drop will occur here due to the greater current density and local resistance. To the extent that the localizing means is close enough to the current modulating material to be at least partially in the region of higher current density, any voltage change associated with changing conductance of the localizing means that occurs in this region as a result of ligand-antiligand action will be greater.

The localizing means itself may have characteristics that make it a current modulating material. Nuclepore, for example, can itself bind protein; it then serves both as localizing means and as a current-modulating means. If Nuclepore is used in an IVEP type of sensor, an additional conducting layer is laid on top of the Nuclepore layer since the Nuclepore structure does not conduct electricity in a direction parallel to its surface.

It should be noted that apparatus of the above types can clearly be constructed in which the predetermined regions contain localizing means with immobilized (or otherwise localized) ligand instead of antiligand.

This invention specifically includes the concept of constructing a biolayer comprising a combination of one or more localizing means and appropriate supporting fixture that is designed for easy insertion or placement of the localizing means into or onto the rest of the sensing apparatus. The biolayer may be disposable. It may be separable from the measuring means. The ability to prepare such a modified localizing means separately from the measuring means is an important advantage of this invention. In some situations, the biolayer may include measuring means such as electrodes. The localizing means may comprise bound antiligand molecules. The biolayer may comprise at least one insulating layer to which the localizing means may be attached. The insulating layer may modulate the electric current flow. Appropriate biolayers may be used with any of the apparatuses disclosed above. In particular, where the apparatus is designed for differential or multiple measurements, the biolayer may comprise two or more localizing means.

EXAMPLE 1

In this experiment, the presence of a specific antibody, goat anti-(rabbit gamma globulin) antibody, or GAR, was detected in a fluid sample by measuring the conductance change of a bioregion containing an immobilized antigen, rabbit gamma globulin, or RAX (short for "rabbit anti-X"). An IVEP apparatus of the type shown in FIG. 8 was used, except that the test and control cells each had its own current path and current electrodes as in FIG. 5D, and fluid sample was added via a sample loop to a fluid inlet port, with no reservoir, also as in FIG. 5D. The apparatus was connected to a conductance bridge of the type described in Example 9.

Test and control bioregions were constructed using 3.5 mm diameter disks punched out of 150 um thick nitrocellulose filter (supplied by Schleicher and Schuell, Keene, N. H., 5.0 um pore size) mounted directly over 0.8 mm holes located in a 0.003" sheet of lexan (polycarbonate, from General Electric). 50 ul of a 2.5 mg per ml solution of Goat IgG ("GAX", short for "Goat-Anti-X", Sigma Chemical Co., St. Louis, MO) was applied to the control bioregion as a negative control. This was allowed to incubate at room temperature for approximately 10 minutes to allow protein to bind to the nitrocellulose. Similarly, 50 ul of a 2.5 mg per ml solution of rabbit IgG ("RAX", Sigma) was applied to the test bioregion. (Although RAX is itself an antibody fraction, it here functions as an antigen to allow testing for the presence of GAR.) The biolayer containing the two protein-coated bioregions was then washed with running buffer (0.2M NaCl, 0.02M NaP04, pH 7.0) and placed into the sensor chamber.

Figure 10:
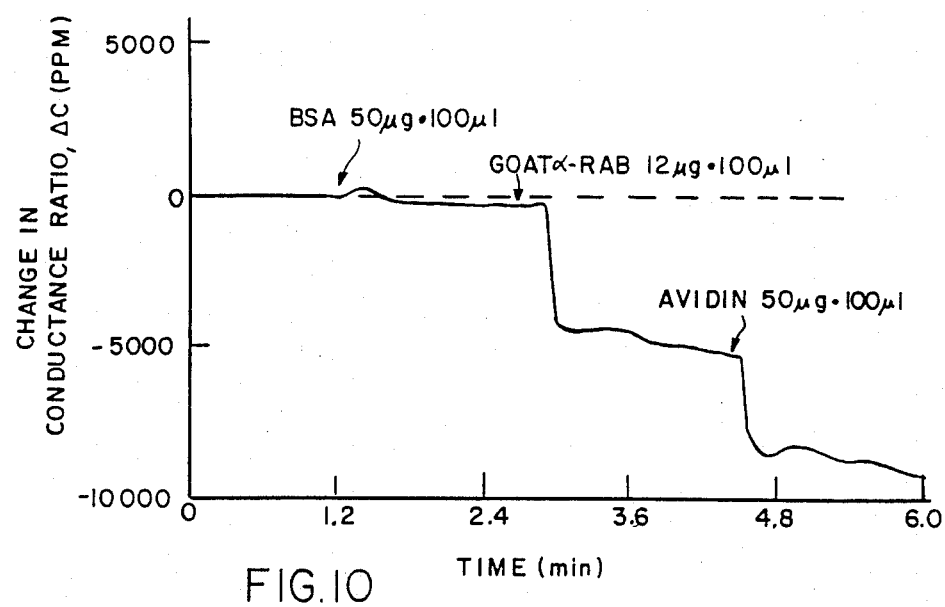
FIG. 10 shows specific detection of an antibody directed against rabbit IgG using an IVEP sensor, with subsequent amplification of the signal using a particle.

Detection of specific GAR antibody was initiated by flowing deaerated running buffer through each biolayer at the rate of approximately 60 ul per minute while monitoring the conductance ratio. This procedure established a stable base line. A collapsible bag containing running buffer located approximately 30" above the sensor maintained a pressure head that gave adequate flow during the course of the experiment. 50 ug of bovine serum albumen (BSA, Fraction V from Sigma) then 12 ug of biotinylated GAR (Sigma), then 50 ug of avidin (Sigma) were added sequentially as indicated in FIG. 10 while the conductance continued to be monitored. Each sample was added in a 100 ul volume via a 100 ul sample loop. The results (FIG. 10) show the following: (1) A non-specific protein, BSA, caused only slight deflection of the baseline signal. However, when biotinylated GAR was added, it caused a negative deflection of approximately 5,000 parts per million (ppm)

in the conductance ratio, C, or 0.5%, and did so in less than a minute.

A particle consisting of the tetrameric protein avidin was used to amplify the above signal. Avidin has a high affinity for biotin; thus, avidin should bind to the immobilized, biotinylated GAR. As is seen in FIG. 10, addition of avidin resulted in an amplification of 3,000 to 4,000 ppm, or almost a factor of two. Addition of larger particles, e.g., polyavidin polymers made by cross-linking avidin molecules with glutaraldehyde, would produce an even larger signal. It should be noted that this amplification example is a variation on the sandwich assay. The first, immobilized, antiligand was RAX, the ligand was biotinylated GAR, and the second, non-interfering antiligand was avidin.

EXAMPLE 2

In this hypothetical example, the presence of two test ligands, GAR and beta-galactosidase, and a positive control ligand, DNP-ovalbumin, are detected simultaneously in the same fluid sample. The conductances of test and positive control bioregions are compared to that of a negative control. Thus the apparatus contains four cells in all. A multiple IVEP sensor apparatus is used in which each cell has a separate fluid path in the manner of FIG. 6A but shares a common electrical path with the cell with which it is being compared in the manner of FIGS. 5A and 5B. That is, each test or positive control cell is placed electrically in series with the negative control during a measurement as described supra. The apparatus is connected to a conductance bridge of the type described in Example 8 to monitor conductance changes.

As in the previous example GAX and RAX are applied to control and test bioregions. 50 ul of a 2.5 mg/ml solution of anti-DNP antibody is applied to a third bioregion, which serves as a positive control. 50 ul of a 2.5 mg/ml solution of antibody to the enzyme beta-galactosidase is applied to another bioregion, which serves as a second test bioregion.

Figure 11:
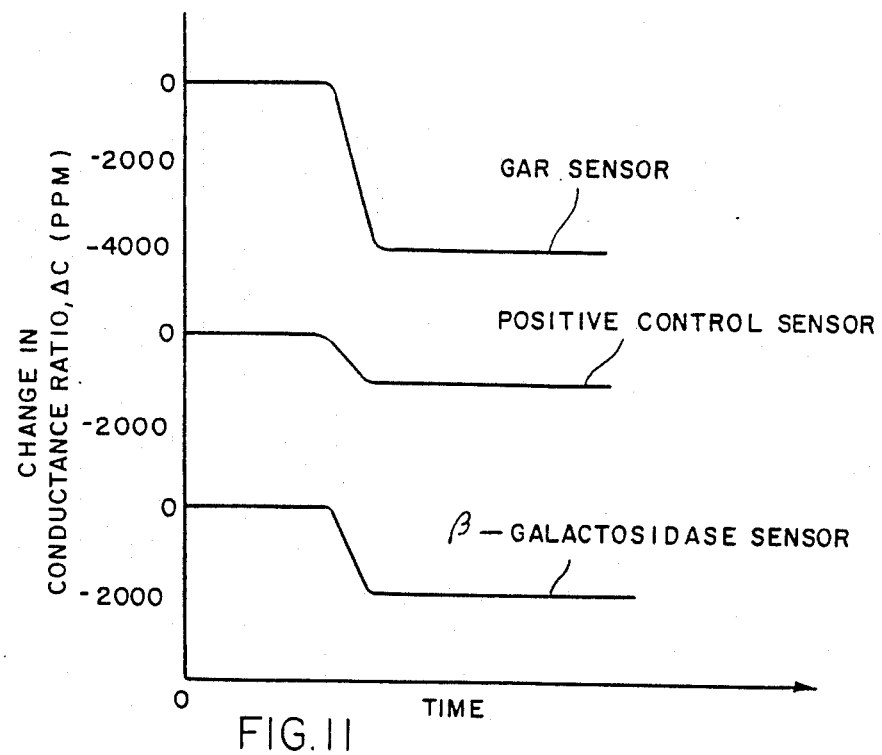
FIG. 11 shows simultaneous detection of two different ligands and use of a positive control.

The biolayer containing the four protein-coated bioregions is washed as in Example 1 and placed into the sensor. Running buffer is flowed through each biolayer as in Example 1 at a rate of approximately 50 ul per minute, and the conductance of each test or positive control cell is monitored in turn, about once every second. When conductance ratios have stabilized, 100 ul of a fluid sample is injected into the sensor apparatus via a 100 ul sample loop. The sample contains running buffer and, in addition, 12 ug of GAR, 6 ug of beta galactosidase, and 3 ug of ovalbumin highly substituted with DNP. FIG. 11 shows the response expected for each sensor. The sensor containing anti-beta-galactosidase responds specifically to beta-galactosidase at the same time as the sensor containing immobilized RAX responds specifically to GAR. The positive control can serve both to estimate the flow rate through the sensors and to calibrate the sensors. This hypothetical experiment shows the way in which the present invention can simultaneously measure multiple ligands in the same fluid, and also test for the proper working and detailed function of the apparatus through use of a positive control.

EXAMPLE 3

In this experiment, the presence of GAR antibody was again detected in a fluid sample. The EVEP apparatus of FIG. 9 was used, except that there was no insulating layer 360 or biolayer 355 as such, the test and control bioregions being placed individually in the sensor apparatus. The apparatus was connected to a conductance bridge of the type described in Example 9.

Localizing means comprising discs 5 mm in diameter and 150 um thick were punched out of HA type filters (0.45 um pore size) consisting of mixed esters of nitrocellulose, purchased from the Millipore Corporation, Bedford, Mass. Such discs were thus 19.6 mm$^2$ in area, and 2.9 mm$^3$, or approximately 3 ul, in volume. The active matrix area through which fluid sample flows was determined by the cross sectional area of the inlet and outlet ports (1 mm dia.) and was about 0.75 mm$^2$. Thus the predetermined region volume was about 0.11 microliter, or 110 nanoliters.

Each 5 mm dia. disc can bind approximately 20 ug of protein; to each disk, 100 ug of protein was applied so that the filter would be completely saturated. Disks were allowed to sit for 5 minutes at room temperature, (under cover to avoid gross evaporation), then washed in 1 ml phosphate-buffered saline solution (PBS, 0.60M NaCl, 0.01M NaPO$_4$, pH 8.3, 0.1% sodium azide) and stored in this saline solution until ready for use. Specifically, to the test disk was applied 10 ul of a solution of RAX (purchased from Sigma Chemical Company, St. Louis, Mo.), adjusted to be 10 mg/ml in RAX, 0.60M in NaCl, 0.01M in NaPO4, pH 7.3, and 0.1% in sodium azide. To the negative control disc was applied 10 ul of a solution of goat IgG (GAX), also purchased from Sigma and adjusted to be 10 mg/ml in GAX, 0.60M in NaCl, 0.01M in NaPO4, pH 7.3, and 0.1% in sodium azide.

Figure 12:
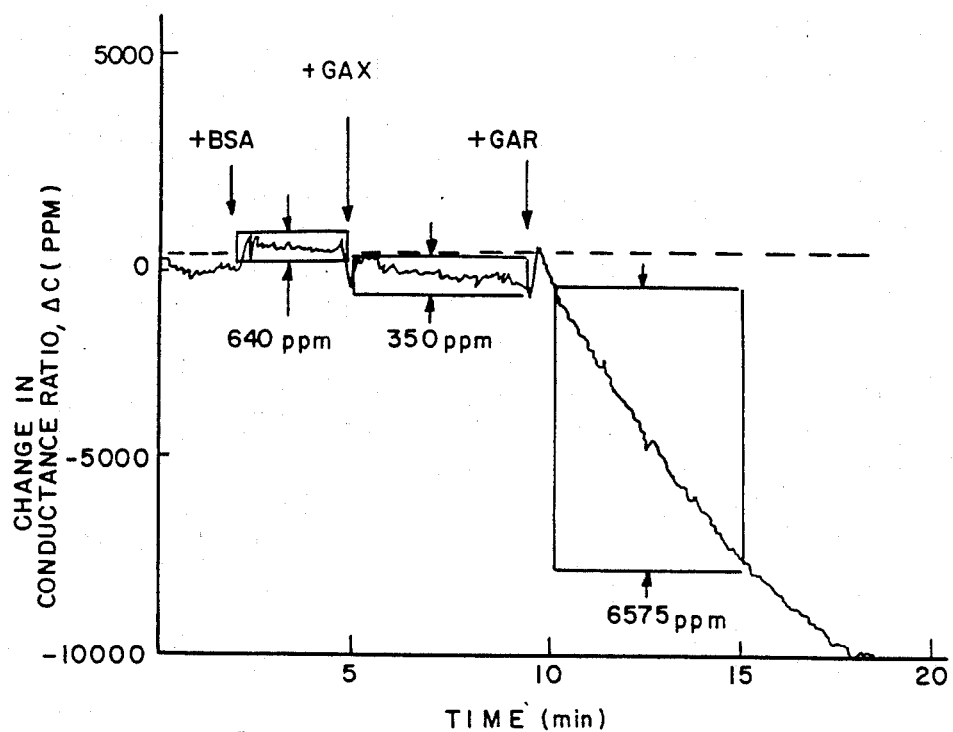
FIG. 12 is similar to FIG. 10 except that an EVEP sensor was used.

The discs were inserted in the apparatus of FIG. 9. The apparatus was assembled, and 50 ul each of BSA, GAX and GAR in PBS were added sequentially to a reservoir chamber containing 5 ml of PBS, to yield final concentrations in the reservoir of 100, 100, and 36 ug/ml respectively. The results in FIG. 12 show that these sensors detected a specific decrease on conductance of the RAX bioregion as a result of RAX/GAR complex formation. Although not shown here, the conductance decrease continued for several more minutes before reaching a plateau at about −20,000 ppm, or 2% total decrease in conductance of the bioregion.

EXAMPLE 4

In this experiment, the presence of an antigen, human gamma globulin ("HAX", short for "human anti-X"), was detected by measuring the change in conductance of a bioregion containing immobilized antibody, goat anti-(human gamma globulin) antibody, or "GAH." Apparatus of the type shown in FIG. 5C was used. The apparatus was connected to a differential conductivity bridge constructed by Neil Brown using two conductivity circuits of the type taught in U.S. patent application Ser. No. 423,281, filed 9/24/82 entitled, Automatic Temperature Measuring Circuitry, herein incorporated by reference. These two circuits were compared using a manually-switched precision ratio transformer (Dekatran decade transformer from Electroscientific Instruments, Portland, OR) in conjunction with a detection circuit consisting of the following: A high-gain preamplifier, a band pass filter with zero phase shift at the operating frequency, and a phase-sensitive detector whose output was connected to a strip chart recorder.

Test and control volumes comprised columns 1 mm in diameter and 10 mm long made by drilling holes in non-conducting acrylic plastic and filled with CNBr-activated bead preparations (Pharmacia Fine Chemicals, Piscataway, N.J.), which served as the localizing means. These beads covalently bind proteins or other molecules containing free $NH_2$ groups. HAX purchased from Sigma Chemical Company, (St. Louis, MO) was covalently bound to gel beads of CNBr-activated Sepharose 4B according to standard techniques published by Pharmacia (see Affinity Chromatography, Principles and Methods, 1979)) to yield a bead suspension containing 9 mg HAX per ml of packed beads. These beads, 0.9% in HAX (w/v), were loaded into the control bioregion. (In this example, the HAX itself serves as a negative control.) Similarly, fluorescent goat anti-(human gamma globulin) IgG (GAH) purchased from Antibodies, Inc., Davis, CA as a 56% pure preparation, was covalently bound to CNBr-activated Sepharose 4B beads to yield a suspension containing 9 mg protein and 5 mg GAH per ml of packed beads=0.5% GAH (w/v). The GAH beads were loaded into the test bioregion.

The following protein solutions were added in order to one ml of phosphate-buffered saline solution (PBS, 0.60M NaCl, 0.01M $NaPO_4$, pH 8.3, 0.1% or 0.05% $NaN_3$) in the reservoir:

(1) Bovine serum albumen (BSA), 100 ul, at a concentration of 15 mg/ul in PBS;
(2) GAX, 100 ul, at the same concentration in PBS;
(3) HAX, 100 ul, at the same concentration in PBS.

Figure 13:
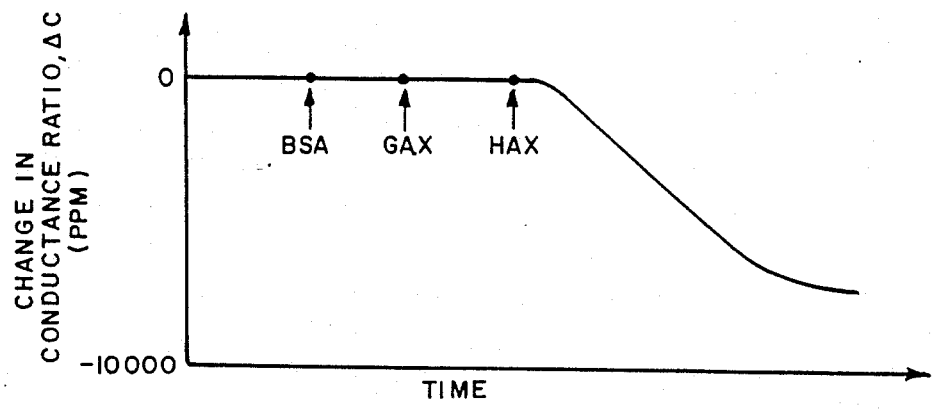
FIG. 13 shows specific detection of an antigen using a columnar sensor.

The results illustrated diagrammatically in FIG. 13 show that there was a change in the conductance ratio after addition to the sample fluid of the ligand HAX, which is bound specifically by the immobilized GAH antibody, but not after addition of GAX, which is a related IgG, nor after addition of BSA, a typical protein. In this experiment it should be noted that:

(a) An antibody was immobilized this time, rather than an antigen as in Examples 1 and 3. This supports the aspect of the present invention which says that it is general with respect to binding of either component of a ligand/antiligand complex.

(b) Immobilized antigen was itself used to prepare the null sensor. As long as the negative control sensor is prepared in such a way that it is physically and chemically similar to the test sensor [except for the specific binding characteristics of the test sensor, of course], and as long the negative control immobilized substance is substantially free of specific interactions which effect changes in bulk conductance, it can serve as a control for nonspecific binding.

(c) The positive response to HAX was not obscured by the presence of other proteins (GAX and BSA) in the fluid sample during the measurement.

EXAMPLE 5

Since the measurement of ligand/antiligand binding according to the present invention is based on alterations in the electrical conductance (or resistance) of a sensor's test volume, any particulate non-conducting substance that accumulates in the test volume due to specific ligand/antiligand binding will alter the conductance measurement. Particles such as erythrocytes, latex beads, plastic beads, or glass beads may be detected or may be used as amplification agents to allow detection of other species. However, use of particles as amplification agents may cause non-specific filter plugging under some circumstances. A strategy wherein insoluble particles or other non-conducting volumes are formed from completely soluble reagents as a result of ligand/antiligand binding could solve this problem.

As an example, the enzyme catalase is covalently linked to goat anti-(rabbit gamma globulin) antibody (GAR) by standard methods such as crosslinking with glutaraldehyde. This complex is used, for example, as a second antibody to test for the binding of primary rabbit antibody to a ligand in a fluid sample which has become bound to a bioregion, e.g. during a sandwich assay. To detect the presence of bound GAR/catalase complex, and hence the presence of bound ligand, hydrogen peroxide (0.01%) is passed through the sensor and is converted to $O_2$ and $H_2O$ via the enzymatic activity of the enzyme. The evolved $O_2$ forms bubbles in or near the bioregion matrix, and these bubbles, being non-conducting, cause decreased electrical conductance that is monitored by the apparatus. Electrodes with gold black or carbon surfaces are used to minimize non-specific catalysis of $H_2O_2$ breakdown that occurs when platinum electrodes are used.

This method potentially allows for an increased sensitivity of detection of ligand/anti-ligand binding of several orders of magnitude as compared to unamplified measurement. The total time required to obtain this measurement should be short (approximately 2 minutes). Also the method can be designed so that it uses inexpensive, non-hazardous chemicals. A variety of other enzymes that produce gases can be similarly used, as can enzymes that produce insoluble precipitates.

EXAMPLE 6

Hybridization of probe nucleic acids (either RNA or DNA) to complementary nucleic acids immobilized on an insoluble matrix is a common laboratory procedure. Although this procedure is highly specific and sensitive, it is relatively difficult to perform, expensive, and lengthy, and it may require large amounts of radioactive reagents. Detection of nucleic acid hybridization by measuring conductance changes thus could be useful if it could be accomplished rapidly and without the use of radiactive tracers. In the hypothetical example below, synthetic homopolymers of adenylic acid and uridylic acid are used in a model system to demonstrate this general principle.

Control and test bioregions comprising nitrocellulose filters (5 um pore size) are treated with polyuridylic acid and polyadenylic acid, respectively. Unreacted binding sites are blocked by addition of 50 ug of BSA or calf thymus DNA to each bioregion. A biolayer containing the bioregions is placed into the IVEP sensor, and a flow of running buffer of 60 ul/minute thru each sensor is initiated to establish a baseline, using appropriate hybridization conditions of salt concentration and temperature for the particular sequences and processes being studied. A sample of 1 ug of polyuridylic acid in 100 ul running buffer is then added to the apparatus. A specific decrease in conductance of the test bioregion as polyuridylic acid binds to the immobilized polyadenylic acid indicates the occurrence of hybridization.

EXAMPLE 7

In this hypothetical experiment, the presence and concentration of a specific amino acid, phenylalanine, is detected in a fluid sample using an equilibrium, rather than a kinetic, method. A "dip-in" type of sensor apparatus is used, such as that shown in FIG. 7B. The apparatus is connected to a conductance bridge such as that described in Example 9.

Test and control bioregions are constructed as follows. For the test bioregion, Whatman filter paper No.

54 (Whatman Limited, England) is activated to bind protein by treatment with cyanogen bromide. The CNBr-activated paper is mounted on an appropriate holder or support, then exposed to a solution of a protein that (1) binds phenylalanine with an affinity constant K which is similar in magnitude to the concentration of phenylalanine to be detected, and that (2) does not metabolize phenylalanine (for example, one could use a phenylalanine hydroxylase that has been mutated to inactivate the enzyme and, if desired, to change its affinity constant). For the control bioregion CNBr-activated paper mounted in the holder is exposed to a solution of a protein that does not bind or metabolize phenylalanine (for example phenylalanine hydroxylase that has been mutated to neither bind nor metabolize phenylalanine may be used). Both bioregions are washed, then the holder is positioned so that the bioregions lie over the sensing means of the apparatus, forming the sensor. The sensor is dipped into one ml of a buffered saline solution whose conductivity is matched to that of the fluid sample to be tested for the presence of phenylalanine, and the conductance ratio of the test and control bioregions is measured. After the value of the ratio has stabilized, 0.1 ml of the fluid sample is added with stirring, and the change in the conductance ratio is noted. Once the ratio has stabilized again, the change is compared to a standard curve to allow determination of the concentration of phenylalanine in the fluid sample.

EXAMPLE 8

A preferred embodiment of an instrument for measuring the relative conductance of a test volume and a control volume is described below. This embodiment is used when the test and control cells are electrically in series.

Specifically, the instrument includes circuitry for measuring the relative change in conductivity between two cells which include a test bioregion and a control bioregion as the test cell bioregion conductivity changes as a result of ligand molecules binding to antiligand sites in its bioregion. The instrument includes circuitry for driving a current through each of the cells and for measuring the voltage drops across the test and control cells as a function of time. The instrument is capable of measuring a change of $10^{-4}$ in the relative conductivity between the two cells with an accuracy of approximately one percent.

The instrument includes a two-stage A.C. analog-to-digital conversion circuit in which the initial conductivities are measured via a successive approximation process, while the relative conductivities are monitored during a test interval via a tracking technique. The circuitry is controlled by a digital controller which can vary the parameters of the measurement processes so as to make the circuit adaptable to measurement of a wide variety of substances using different cell configurations and/or electrolytes. Extensive calibration and diagnostic capabilities are provided to ensure the accuracy of the measurements.

Figure 14:
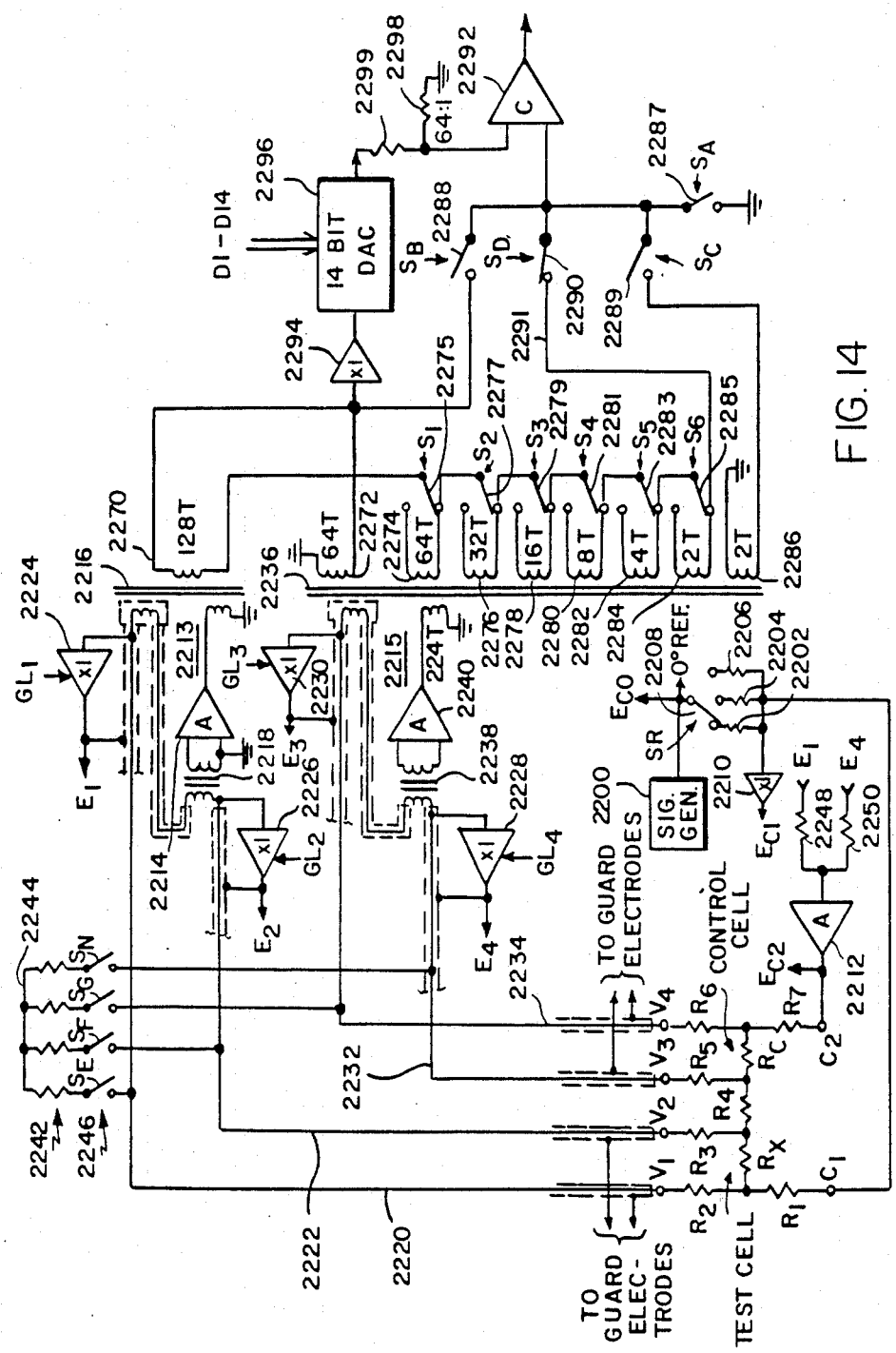
FIG. 14 is a block diagram of a circuit for measuring conductivity for use with test and control cells using four-terminal measurements.

FIG. 14 is a schematic diagram of circuitry which can measure the relative change in conductivity between the test and control cells. As in FIG. 5B, the resistances of the test and control cells are represented by resistors $R_x$ and $R_c$; terminals $V_1-V_4$ are the voltage measurement terminals, terminals $C_1$ and $C_2$ are the current input terminals, and resistors R1-R7 represent the impedances of the fluid channels, which includes contributions of the fluid impedances, polarization impedances, and other effects.

In FIG. 14, a signal generator 2200 provides a very pure sine wave output signal at a frequency of 384 Hz. While a higher frequency would make the design of the measurement circuitry more simple, problems with maintaining the accuracy of four-terminal measurements which result from capacitive effects and other error sources are lessened with the use of lower frequencies.

The signal generator output signal is applied to terminal $C_1$ through one of resistors 2202, 2204, or 2206, as selected by a switch 2208. In the described embodiment, resistors 2202, 2204, and 2206 have values of 5K, 10K, and 15K ohms. Switch 2208 and resistors 2202-2206 are used to match the output signal to the impedance of the test and control cells, depending on the electrolyte used and the cell configuration. Although switch 2208 is shown as a manually-operated switch in FIG. 14, it could be controlled by the digital processor in alternate embodiments. The signal at terminal $C_1$ is also applied to a unity-gain buffer amplifier 2210 which provides a buffered output signal $EC_1$ which is equal to the voltage at terminal $C_1$.

Terminal $C_2$ is driven by the output of an amplifier 2212. As discussed in more detail below, amplifier 2212 drives terminal $C_2$ so that the voltage at $C_2$ is equal in magnitude but opposite in phase to the voltage at terminal $C_1$ which causes a current to flow from terminal $C_1$ through the test and control cells to $C_2$, as described above in the description of FIGS. 5A and 5B. Noise pickup is minimized by providing a "balanced" drive to the current terminals $C_1$ and $C_2$.

The voltage between terminals $V_1$ and $V_2$ is applied to a high-input impedance, differential amplifier 2213 comprised of amplifier 2214 and transformers 2216 and 2118. This circuit is discussed in more detail below in connection with FIG. 16. The voltage across terminals $V_3$ and $V_4$ is applied to a similar amplifier circuit 2215 including transformers 2236 and 2238 and amplifier 2240. The operation of amplifier circuit 2215 is similar to that of amplifier circuit 2213. In practice, the apparatus containing the test and control cells may be some distance away from the electronic measurement circuitry. The signals from terminals $V_1-V_4$ are applied to the differential amplifiers 2213 and 2215 through shielded cables 2220, 2222, 2232, and 2234.

Terminal $V_1$ is connected to the signal or center conductor of cable 2220, and the signal at terminal $V_1$ is applied to one side of the primary winding of transformer 2216. The signal on the center conductor of cable 2220 is applied to the input of a unity-gain, high-impedance, buffer amplifier 2224, which is physically located close to the electronic measurement circuitry. The output of amplifier 2224 is connected to the shield of cable 2220 and maintains the voltage on the shield at the same level as the signal on the signal conductor of cable 2220. As shown in FIG. 14, the output of amplifier 2224 also drives a shield around the primary winding of transformer 2216 and a shield around the wire connecting the windings of transformers 2216 and 2218. The input to a second unity-gain buffer amplifier 2226 is connected to the signal conductor of cable 2222 near its connection to transformer 2218. The output of amplifier 2226 drives the shield of cable 2222. Providing an active drive for the shield conductor reduces noise pickup and minimizes losses caused by capacitive leakage in cables 2220 and 2222.

The shield conductors of cables 2220 and 2222 may be connected to guard rings in the test cell to provide further reduction of errors. This may be better understood by referring to the diagram of the test and control cell configuration shown in FIG. 8A. As discussed above, fluid seepage around the o-ring seals may result in resistive leakage paths which will cause errors in the conductivity measurements. The guard electrodes G1-G4 reduce or eliminate such errors. The guard electrodes are driven by the signals on the shields of the cables to each of the terminals. The resistance of electrical paths produced by leakage around the o-rings will be relatively high. Since the guard electrodes are maintained at a voltage equal to the voltage on the associated terminal $V_1$-$V_4$ by the low output impedance of amplifiers 2224-2230, any current flowing between the two cells will be principally provided by the guard electrodes. This reduces or eliminates errors which otherwise would be caused by electrical leakage along paths resulting from fluid seepage around the o-ring seals.

Signals $E_1$ and $E_2$ from the outputs of amplifiers 2224 and 2226 are buffered signals equal or approximately equal to the voltages at terminals $V_1$ and $V_2$. Signals $GL_1$ and $GL_2$ are applied to amplifiers 2224 and 2226 during diagnostic routines to enable the leakage current from the shield and guard electrode circuit for each amplifier to be measured, as discussed below.

The voltage across terminals $V_3$ and $V_4$ is processed by circuitry similar to the circuitry described above connected to terminals $V_1$ and $V_2$. The signals on terminals $V_3$ and $V_4$ are connected to the primary windings of transformers 2236 and 2238 by shielded cables 2232 and 2234. The signals on the center conductors of cables 2232 and 2234 are applied to amplifiers 2228 and 2230 which maintain the shields of the cables at a potential equal to the signal on the associated terminal and which provide buffered signals $E_3$ and $E_4$ equal to the voltages at terminals $V_3$ and $V_4$. Amplifiers 2228, 2230, and 2240, transformer 2238 and the primary winding of transformer 2236 are essentially identical to the corresponding circuitry connected to terminals $V_1$ and $V_2$ except that terminals $V_3$ and $V_4$ are connected to this circuitry with the opposite polarity. In other words, the output signals from transformers 2216 and 2236 produced by a current flowing through the test and control cells will be opposite in phase from each other.

As described above, it is desirable to apply a voltage to terminal $C_2$ which causes the signals at $V_1$ and $V_4$ to be equal in magnitude but opposite in polarity. This is done by means of a negative feedback loop provided by amplifier 2212. The $E_1$ signal is applied via a resistor 2248 to the input of amplifier 2212. The $E_4$ signal is similarly applied to the input of amplifier 2212 via a resistor 2250. Amplifier 2212 is a relatively high-gain, inverting, AC amplifier. In the described embodiment, amplifier 2212 has a gain of approximately 10,000 at the operating frequency of 384 Hz. The $E_1$ and $E_4$ input signals applied to amplifier 2212 are a function of the current driven through the test and control cells by amplifier 2212, and the circuit forms a closed loop feedback circuit which forces the signal level at the input of amplifier 2212 to zero or ground potential. In order for this to occur, the $E_4$ signal must be equal and opposite to the $E_1$ signal, which is the desired condition.

Each of the signal conductors of the cables may be selectively connected by switches 2246 and resistors 2242 to a common node 2244. Although not shown in FIG. 14, the connection of switches 2246 to the cables should be physically close to the inputs of the buffer amplifiers 2224-2230. In the described embodiment, resistors 2242 each have a value of 1 kilohm. Switches 2246 are electronically controlled switches. The four switches 2246 are respectively controlled by signals $S_E$, $S_F$, $S_G$, and $S_H$ from the digital controller. Switches 2246 may be selectively closed during diagnostic routines to provide a known resistance between the signal conductors of the cables. By comparing the voltages at terminals $V_1$-$V_4$ with switches 2246 open and closed, leakage paths between the terminals may be determined, as discussed in more detail below.

The output winding 2270 of transformer 2216 has 128 turns and provides a signal proportional to the voltage drop across the test cell. Transformer 2236 has multiple output windings, each of which provides a signal proportional to the voltage drop across the control cell. By selectively connecting the windings of transformer 2236 in series the output of transformer 2236 may be scaled with respect to the output of transformer 2216.

Transformer 2236 has a 64-turn output winding 2272 one end of which is grounded. The second end of 64-turn winding 2272 is connected to one end of output winding 2270 of transformer 2216. Transformer 2236 additionally has six binary-weighted windings 2274-2284 having respectively 64, 32, 16, 8, 4, and 2 turns. Switches 2275 through 2285 are single-pole double-throw switches and typically low-noise FET switches which are electronically controlled. In the present embodiment, six signals $S_1$-$S_6$ are applied to switches 2275-2285 by the digital processor to control the states of the switches. These switches are connected to windings 2274-2284 as shown in FIG. 14 so that any combination of the windings may be connected in series, depending on the settings of signals $S_1$-$S_6$. Thus, by appropriately setting the switches $S_1$-$S_6$, any even number of turns from 2 through 126 may be connected in series to provide an output signal which is proportional to the voltage drop across the control cell biolayer and which may be scaled over a range of 1:126.

The signals from the various output windings of the two transformers 2216 and 2236 are summed in the following manner. One end of 64-turn winding 2272 on transformer 2236 is grounded. The second end of winding 2272 is connected to one end of the single output winding 2270 on transformer 2216. The windings are connected so that the two windings are connected in series and with the same phase. The second end of winding 2270 is connected to the common terminal of switch $S_1$ so that the selected windings of binary-weighted windings 2274-2284 are connected in series with windings 2270 and 2272. The output from windings 2274-2284 is also in phase with the output from winding 2270. Since, as described above, the input signals to transformers 2216 and 2236 are opposite in phase, the output signals from the two transformers are also opposite in phase.

The net effect of the above-described connection is that the signal from output winding 2270 is connected in series, and thus subtracted (due to the oppositely-phased outputs), from the output signal from 64 to 190 turns of transformer 2236, depending on the settings of switches $S_1$-$S_6$. In other words, by properly setting switches $S_1$-$S_6$, the output signal from transformer 2236 may be scaled so that it is approximately equal to the output signal from transformer 2216 for voltage drops across the test cell ranging from about 50% to 150% of the voltage drop across the control cell. The signal on line 2290 represents the exact difference of the output signals from transformers 2216 and 2236.

The output from the 64-turn winding 2274 is applied via a unity-gain buffer amplifier 2294 to the analog input of a 14-bit, multiplying digital-to-analog converter (DAC) 2296. DAC 2296 may be implemented, for example, by an ICL 7134 integrated circuit. Fourteen digital input signals $D_1$–$D_{14}$ are applied to the DAC by the digital processor. In response to signals from the digital processor, the output from winding 2272, which is proportional to the voltage drop across the control cell, may be scaled over a range of $2^{14}$. The output from DAC 2296 is applied to a resistive 64-to-1 divider made of resistors 2298 and 2299. This divider scales the output of the DAC so that one MSB of the DAC is equivilent to the output from one turn of the windings on transformer 2236. In this manner, the selectable output windings of transformer 2236 and the DAC 2296 allow the output from the control cell to be scaled over a 220-bit range.

The output from resistive divider 2298–2299 is applied to one input of a comparator 2292. The second input to the comparator is selected by switches 2287–2290. These switches are respectively controlled by signals $S_A$–$S_D$ from the digital processor. Closing switch $S_A$ connects the second input to comparator 2292 to ground; switch $S_B$ connects the input to the output of 64-turn winding 2272; $S_C$ to the output of 2-turn winding 2286; and switch $S_D$ to the output of series-connected windings 2270, 2272, and 2274–2284, as determined by the setting of switches $S_1$–$S_6$. Switches $S_A$–$S_C$ are used during calibration, and the operation of these switches is discussed in detail in connection with FIGS. 20–22.

During conductivity measurements, switch $S_D$ is closed to connect the second input to the comparator to the series-connected windings 2270, 2272, and 2274–2284. In this mode, the test cell output signal from 128-turn winding 2270 is effectively subtracted from the control cell signal as scaled over a range of approximately 0.5 to 1.5, depending on the signals $S_1$–$S_6$ applied to the selectable windings 2274–2284. The $S_1$–$S_6$ signals are set by the digital processor so that the control cell output from the windings of transformer 2236 approximates as closely as possible the test cell output signal from transformer 2216. The first input to the comparator is provided by the DAC 2296 scaled by 64:1 divider 2298–2299. The maximum output from the divider is equal to one-half of the smallest increment provided by the settings of switches $S_1$–$S_6$.

Thus, the combination of the six MSB's provided by the transformer winding switches $S_1$–$S_6$ and the 14 LSB's provided by the DAC provides a 220-bit conversion of the test cell signal effectively using the control cell signal as a reference voltage for the conversion. The described circuit takes advantage of the high accuracy of a precision-ratio transformer in determining the most significant bits, which do not change often, while allowing fast tracking of the changing test cell signal by using the multiplying DAC 2296 to provide the least significant bits.

Figure 15:
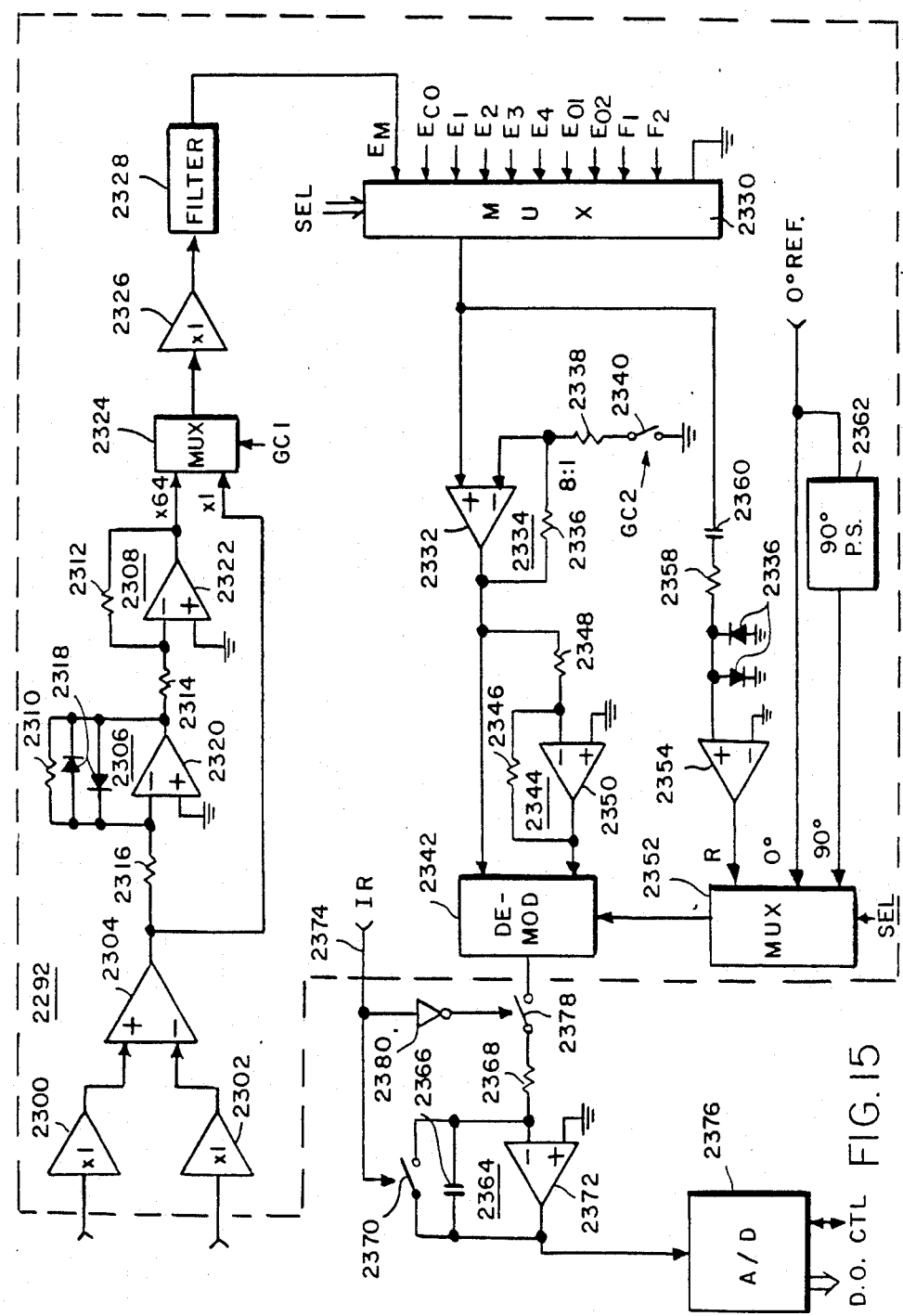
FIG. 15 is a schematic diagram showing further details of the comparator circuit of FIG. 14.

FIG. 15 shows the comparator circuitry in more detail. The two inputs to comparator 2292 are applied to two, unity-gain, buffer amplifiers 2300 and 2302 whose outputs are applied to a precision differential amplifier 2304. The output of amplifier 2304 is directly applied to one input of a multiplexer 2324. The output of amplifier 2304 is also applied to multiplexer 2324 via two amplifier stages 2306 and 2308, each of which have a gain of 8 for a total gain of 64. A gain control signal GC1 is applied to multiplexer 2324 by the digital processor to select a gain of 1 or 64 for the output signal from amplifier 2304.

Amplifier stages 2306 and 2308 are made up of op-amps 2320 and 2322 connected as inverting amplifiers as shown in FIG. 15. Resistors 2310–2316 are chosen to give a gain of 8 for each amplifier stage. Opposed diodes 2318 are connected in parallel across the feedback resistor to the first amplifier stage 2306 to limit the output signal amplitude. Although a gain value should be selected to keep the operation of amplifier stages 2306–2308 and the following circuitry in the linear region, noise spike may be present. If such spikes were to drive any of the circuitry of comparator 2292 into saturation, large errors might result. Diodes 2318 serve to suppress any such noise spikes.

The output of multiplexer 2324 is applied via buffer amplifier 2326 to an AC bandpass filter circuit. It is important that filter circuit 2328 has a high attenuation of frequencies removed from the signal frequency of 384 Hz while maintaining a very flat phase characteristic. One circuit suitable for implementing filter 2328 is the bi-quad amplifier circuit described in an application for "Bandpass Amplifier Filters" filed Sept. 24, 1982, Ser. No. 422,732 of N. Brown. Other circuits known to those in the art may also be used to implement filter 2328.

The output of filter 2328 is applied to one input of a multiplexer 2330. Other signals applied to multiplexer 2330 include the $E_1$–$E_4$ signals, representative of the voltages at terminals $V_1$–$V_4$, the $EC_1$ and $EC_2$ signals, representative of the voltages at the current terminals $C_1$ and $C_2$, the F1 and F2 signals, representative of the flow in each of the test and control cells, and ground. Multiplexer 2330 normally connects the output of filter 2328 to the input of amplifier stage 2334 when the circuit is measuring the conductance of the test or control cells. The digital processor provides the appropriate SEL input to multiplexer 2330 to measure the other signals applied to the multiplexer for calibration and diagnostic purposes, as discussed below. It should be noted that the signals applied to multiplexer 2330 are AC signals which must be demodulated prior to being measured.

The output of multiplexer 2330 is applied to the non-inverting input of an op-amp 2332 of amplifier stage 2334. A feedback resistor 2336 is connected between the output and inverting input of the op-amp. A second resistor 2338 is connected to the inverting input of the op-amp and is also selectively connected to ground through a switch 2340. The ration of resistors 2336 and 2338 is 8 to 1. By closing switch 2340, a gain of 1 or of 8 may be selected for amplifier stage 2334. Switch 2340 is typically a low-noise FET switch which is controlled by a signal $GC_2$ provided by the digital processor.

The output from amplifier 2334 is applied to one input of a demodulator circuit 2342 directly, and to a second input of the demodulator via a unity-gain inverting amplifier stage 2344, made up of op-amp 2350 and resistors 2346 and 2348. Demodulator 2342 may be implemented, for example, by AD 534L balanced multiplier circuit. Inverting amplifier 2344 provides a signal equal to the signal from amplifier 2332 but 180 degrees out of phase. This signal is applied to the second input to the balanced demodulator. It is desirable to use a balanced type of demodulator to provide as stable a signal as possible at the demodulator output. The output signal from the demodulator represents the value of the difference between the test and control cell voltages.

The reference input signal to demodulator 2342 is selected by a multiplexer 2352. The signal from multiplexer 2352 is a reference clock signal derived from signal generator 2200 which is used to demodulate the AC signal applied to the balanced inputs to the demodulator. A 0-degree reference signal taken directly from the signal generator is applied to one input of the multiplexer. This signal is normally used to demodulate the input to the demodulator, as discussed below, when the conductivity of the control and test cells is measured.

Although, in theory, the signals applied to the comparator circuitry 2292 should be exactly in phase with the output signal from signal generator 2200, small phase shift errors may be introduced by parasitic impedances in the circuitry and other error sources. These phase errors can cause errors in the amplitude of the demodulated signal, since the reference signal will no longer be exactly in phase with the signal to be demodulated. Two other reference signals may be selected by multiplexer 2352 which allows such errors to be measured so that proper compensation can be made.

A second signal is applied to the multiplexer by limiting amplifier 2354. This signal is designated as the random reference signal, since its phase relationship to the clock signal is not exactly known. The output from multiplexer 2330, which is the signal to be demodulated, is applied via capacitor 2360 and resistor 2358 to one input of an op-amp 2354. Two opposed diodes 2356 are connected between the input of the op-amp and ground to limit the input voltage to the op-amp. The op-amp is operated in open loop mode and provides at its output a square wave signal in phase with the output from multiplexer 2330. By demodulating the output from multiplexer 2330 with this signal, the magnitude can be determined independent of any unknown phase shifts which the prior circuitry may have introduced.

A third signal is applied to multiplexer 2352 from a 90-degree phase shifter circuit 2362. The 0-degree reference is applied to the input of 90-degree phase shifting circuit 2362. Phase shifter 2362 provides a precise 90 degree phase shift to the 384 Hz input signal and provides a reference clock signal in phase quadrature to the 0-degree signal. During diagnostics, the input to the demodulator may be demodulated using the random and 90-degree reference signals as well as the 0-degree reference to determine exactly the quadrature component introduced into the signal to be measured from the best and control cells. The digital processor may use this information to ensure that the quadrature error is not so large as to result in erroneous measurements and optionally to correct the measured conductivity value, if such corrections are needed.

The output from the demodulator is applied to a precision reset-integrator circuit 2364. Integrator 2364 is implemented using a high gain precision amplifier 2372, input resistor 2368, and integrating capacitor 2366. Capacitor 2366 should be a polypropylene or other similar type capacitor having high stability. Typical values for resistor 2368 and capacitor 2366 are 100 kilohms and 1.0 microfarads. An electronic switch 2370 is connected across the capacitor and is controlled by an integrator reset signal IR.

A second switch 2378 is connected in series with the input to the integrator and is controlled by an inverted IR signal from an inverter 2380. Thus, when the IR Signal is inactive, switch 2370 is closed to reset the integrator while switch 2378 disconnects the input signal to the integrator. When the IR signal goes active, the input signal is applied to the integrator and the reset switch 2370 is opened, allowing the integrator 2364 to integrate and filter the output signal from the demodulator.

The output signal from the demodulator is applied to the input of an A/D converter 2376. Converter 2376 may be implemented, for example, by means of an AD5-74AJD 12-bit bipolar A/D converter circuit manufactured by Burr Brown. This converter performs a conversion in approximately 25 microseconds, which is essentially instantaneously with respect to the rate of change of the output from integrator 2364. A/D converter 2376 is controlled by signals to and from the digital processor, represented by the CTL signals to and from converter 2376 in FIG. 15. The digital output values are read by the digital processor after each conversion is performed.

As will become more clear after reading the discussion of the measurement procedures explained below in conjunction with FIGS. 20–23, the present invention allows a very low noise measurement to be made of the test and control cell conductivities using a method which requires essentially no settling time during the period that the circuitry is tracking the change in conductivity of the test cell. Further, the finite time integration provided by integrator circuit 2364 provides near optimal filtering of noise which may be present in the signals from the cells.

FIG. 16 shows further details of input amplifier circuitry 2213 connected to terminals $V_1$ and $V_2$. The operation of the amplifier circuitry 2215 connected to terminals $V_3$ and $V_4$ is similar, except that transformer 2236 has multiple secondary windings while transformer 2216 has a single secondary winding, as discussed above. In order to maintain accuracy, it is important the the output signals from transformer 2216 have a precise relationship to the signals from transformer 2236. By using precision-ratio transformers for transformers 2216 and 2236, the output voltages from the various windings can be made accurate to better than one part in $10^6$.

In FIG. 16, transformer 2218 has an input winding with two taps to provide three winding segments 2402, 2404, and 2406 having 165, 125, and 235 turns respectively, and a single 1650-turn output winding 2408. Transformer 2216 is a precision ratio transformer and has a 224-turn input winding 2424, a 128-turn output winding 2410, discussed above in connection with FIG. 14, and three single-turn output windings 2412, 2414, and 2416. One end of winding 2416 is connected to the lower tap of transformer 2218 via a switch 2422. Similarly the two taps to the connections between windings 2412 and 2414 are selectively connected to the two taps on winding 2218 via switches 2418 and 2420. One of switches 2418–2422 is closed during operation to select the gain of the amplifier stage. The impedance across the windings of transformer 2218 is much larger than the impedance across the single turn windings 2412–2416, and transformer 2218 ensures that a high enough impedance is provided to the sensors. Transformer 2218 also serves to isolate the four electrodes from the analog ground.

The secondary winding of transformer 2218 is connected to the input of an AC amplifier 2214. Amplifier 2214 has a very high gain at the operation frequency of 384 Hz, typically on the order of 100,000, while maintaining a very stable phase shift. The output of amplifier 2214 is connected to input winding 2424 having 224 turns on transformer 2216. The input of amplifier 2224 is connected to the line going to terminal $V_1$. Its output is connected to the shields of the cables providing the input to transformer 2218. These shields include the shield of line 2220 and the shields of each of the single-turn windings 2412–2416. The shield of line 2222 to terminal $V_2$ is similarly driven by amplifier 2226, not shown in FIG. 16. The input windings 402–406 of transformer 2218 are shielded, and this shield is also connected to and driven by amplifier 2226.

Amplifier 2213 serves to provide a high impedance across terminals $V_1$ and $V_2$ and also provides a relatively high impedance to the input of amplifier 2214. The gain of amplifier 2213 is determined by the ratio of single-turn windings 2412–2416 to output windings 2410 and is thus very accurate and stable. This is done in the following manner.

The connection from the output of amplifier 2214 through transformers 2216 and 2218 back to the input of amplifier 2214 provides negative feedback. Due to the high gain of amplifier 2216, the negative feedback makes the input to amplifier 2214 a virtual ground. The voltage across the output winding of transformer 2218 must therefore be essentially zero, and hence the voltage across the selected input winding of transformer 2218 must also be zero. Since the voltage drop across the input winding 2402–2406 to transformer 2218 and the single-turn windings 2412–2414 must equal the voltage across terminals $V_1$ and $V_2$, essentially the entire voltage across $V_1$ and $V_2$ appears across the single turn windings 2412–2416. The gain from lines 2200 and 2222 (connected to the inputs to amplifier 2213) to the output winding 2410 is essentially determined solely by the ratio between the number of windings selected by switches 2418–2422 and the 128-turn output winding 2410. By selectively closing switches 2418–2422, gains of 128, 128/2, and 128/3 may be selected. Switches 2418–2422 and the different taps on transformers 2216 and 2218 enable a relatively constant input impedance to amplifier 2214 to be maintained when the amplifier gain is changed.

FIG. 17 shows one circuit suitable for amplifiers 2224, 2226, 2228, and 2230 which drive the shields of the cables to terminals $V_1$–$V_4$ and the guard electrodes. The input signal is applied to the non-inverting input of an op-amp 504 through a capacitor 502. Op-amp 504 may be implemented by LF356 amplifiers. The output of op-amp 504 is connected to its inverting input to provide a unity-gain amplifier. Two large value resistors 506 and 508 are connected in series between the non-inverting input to the op-amp and ground to provide a DC reference level at the input. A capacitor 508 connects the junction of resistors 506 and 508 and the op-amp output.

The output from the op-amp is connected through a capacitor 512 and a resistor 510 in parallel with switch 514 to provide the amplifier stage output signal. Resistor 510 is typically 1 kilohm. Switch 514 is an electronically controlled switch such as a FET switch and is normally closed during conductivity measurements. During diagnostic routines, the processor provides a guard leakage measurement signal GL which opens switch 514, putting resistor 510 in series with the output signal to the shields and guard electrodes. If there is no leakage current flowing from the guard and shield circuit, the $E_1$ through $E_4$ voltages will remain the same when switch 514 is closed. If there is any significant leakage current, the leakage current will cause a voltage drop across resistor 510. By measuring the $E_1$ through $E_4$ voltages with switches 514 closed and open, the leakage current in each shield and guard electrode circuit can be determined.

FIG. 18 is a schematic of an AC amplifier circuit which may be used for the AC amplifier 2212. The circuit consists of four 5532 op-amps 641–644 connected as a bi-quad amplifier/filter, as shown in FIG. 18. This amplifier configuration is discussed more fully in an application for "Bandpass Amplifier Filters" filed Sept. 24, 1982, Ser. No. 422,732, of N. Brown. The circuit provides an open-loop gain of approximately 30,000 while maintaining a very stable zero-phase shift characteristic around the operating frequency of 384 Hz. Typical values for the components shown in FIG. 18 are as follows:

| 602 | 100 ohms | 618 | 4.99 K |
|-----|----------|-----|--------|
| 604 | 10 K     | 630 | 0.0082 mfd. |
| 606 | 150 K    | 632 | 0.002 mfd. |
| 608 | 10 K     | 634 | 2.2 mfd. |
| 610 | 1 K      | 641 | 5532 |
| 612 | 10 K     | 642 | 5532 |
| 614 | 51 K     | 643 | 5532 |
| 616 | 49.9 K   | 644 | 5532 |

The circuitry of AC amplifiers 2214 and 2240 may be implemented by means of a two stage bi-quad amplifier circuit. One such circuit suitable for use with the described embodiment and which includes compensation for DC offset errors is shown in the above-referenced patent application for "Bandpass Amplifier Filter" in FIGS. 8 and 9 thereof.

FIG. 19 is a schematic diagram of one circuit for implementing the 90-degree phase shifter 2362. The input signal to the phase shifter circuit is applied through series-connected capacitor 708 and resistor 702 to the inverting input of an op amp 714. The inverting input of the op-amp is grounded. A resistor 704 and capacitor 712 are connected in parallel between the output and the inverting input to op-amp 714. An op-amp 716 is connected as a unity-gain buffer amplifier. The output of op-amp 714 is applied to the input of the second op-amp 716 via a resistor 706. A capacitor 710 is connected between the input to op-amp 716 and ground. Typical values for the components in FIG. 19 are as follows:

| 702 | 40 K       | 710 | 0.001 mfd. |
|-----|------------|-----|-----------|
| 704 | 4 megohms  | 712 | 0.01 mfd. |
| 706 | 8.2 K      | 714 | LF356 |
| 708 | 1.0 mfd.   | 716 | LF356 |

Figure 20A:
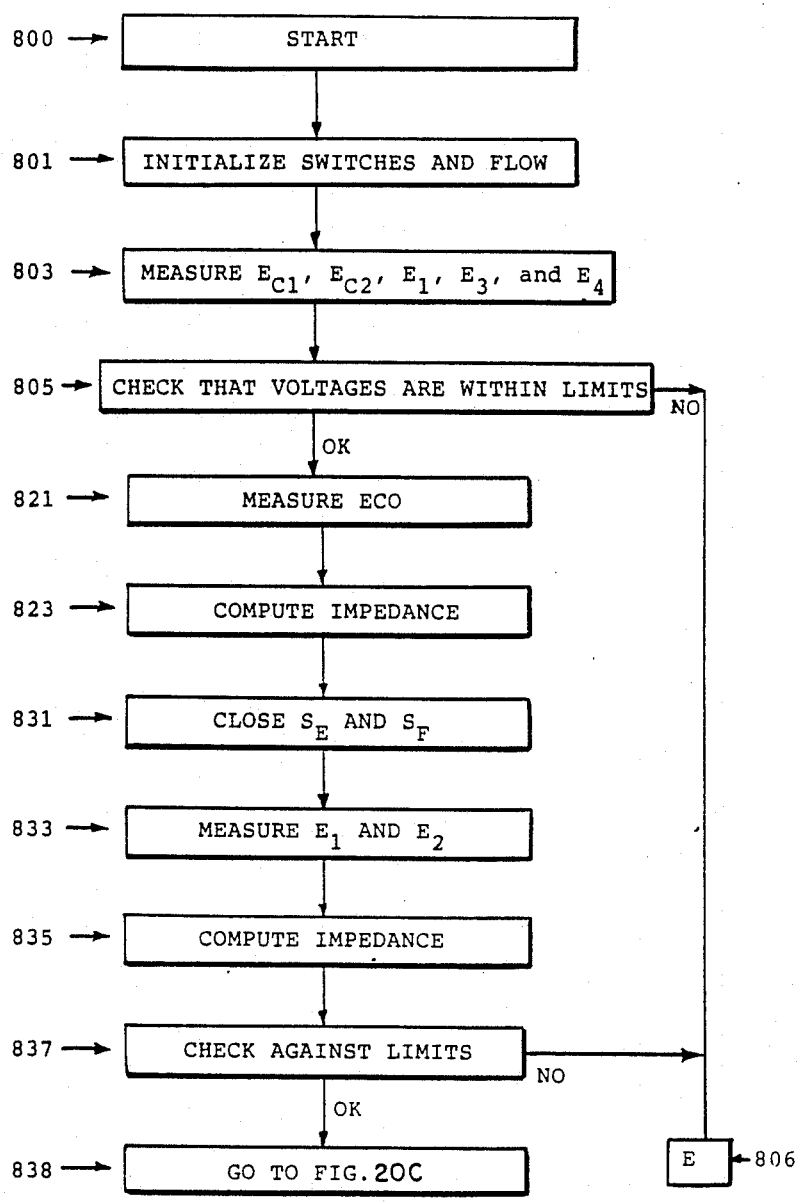
FIGS. 20, 21 and 22 are flow diagrams showing one method by which a measurement of conductivity may be performed by the circuitry described herein.
Figure 20B:
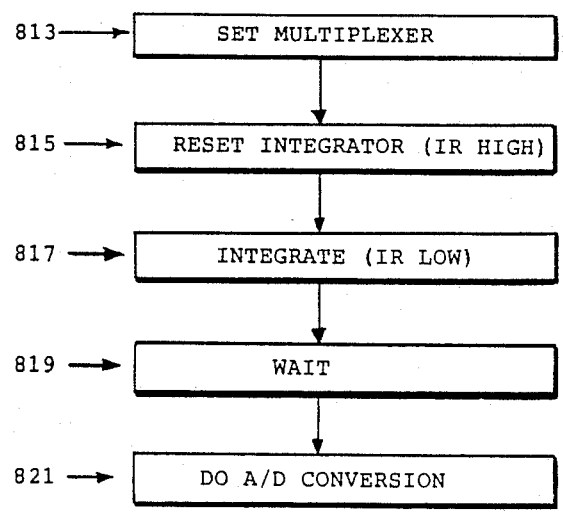
Figure 20C:
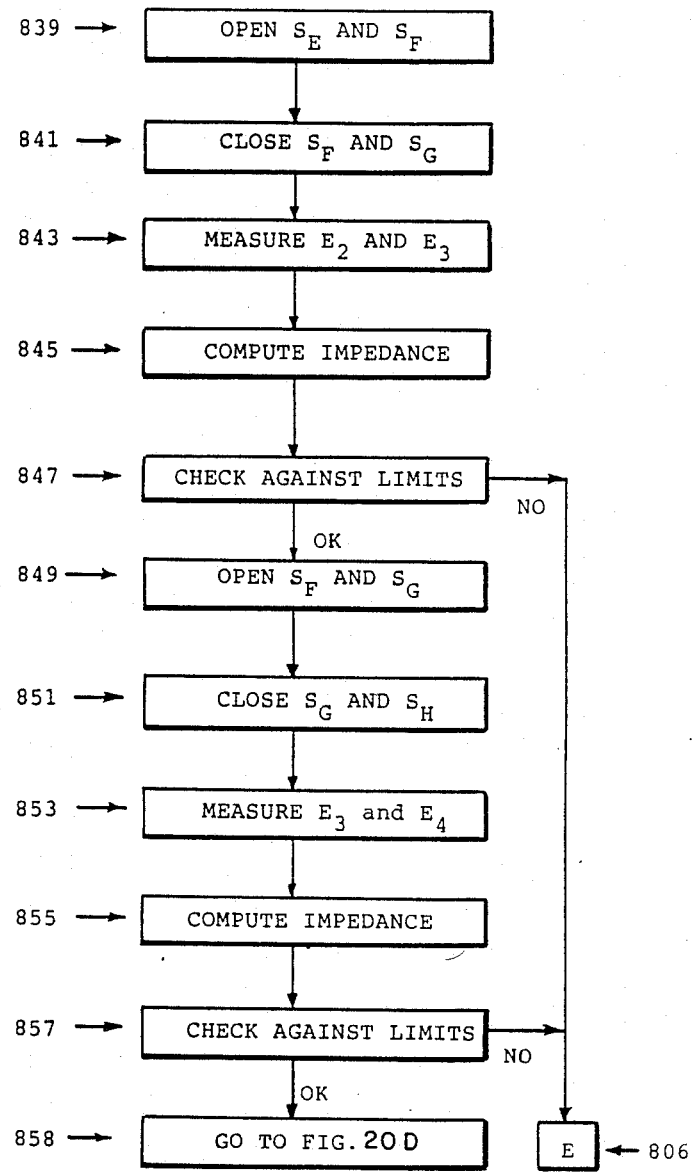
Figure 20D:
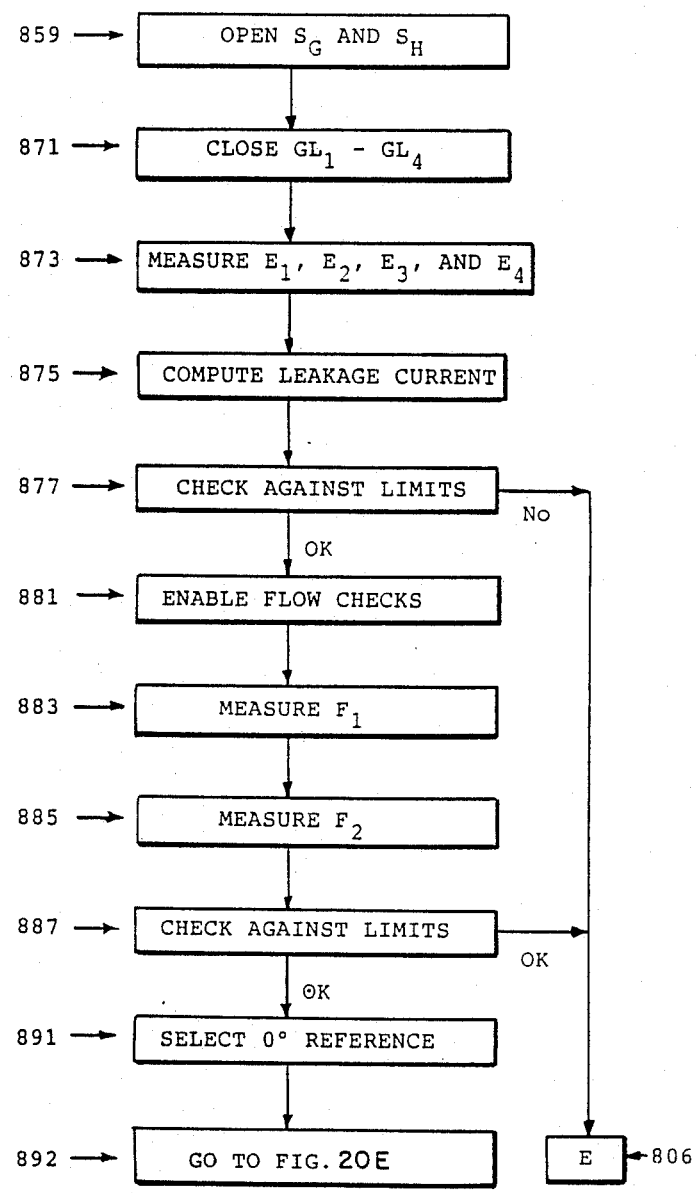
Figure 20E:
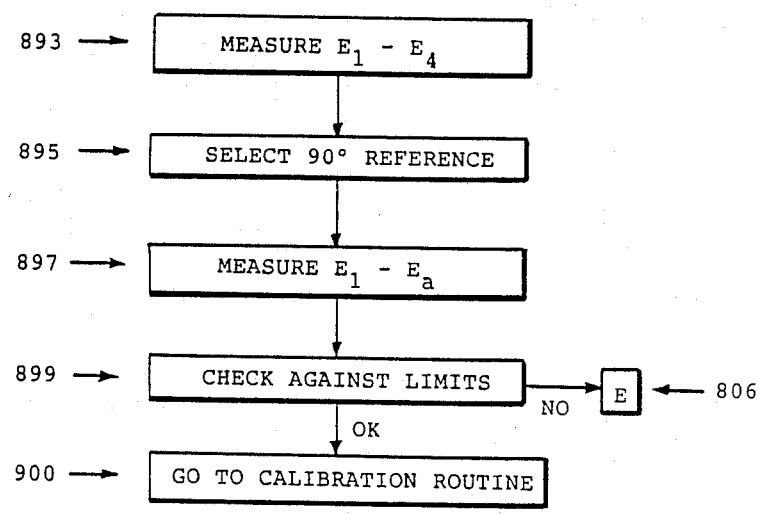
Figure 21A:
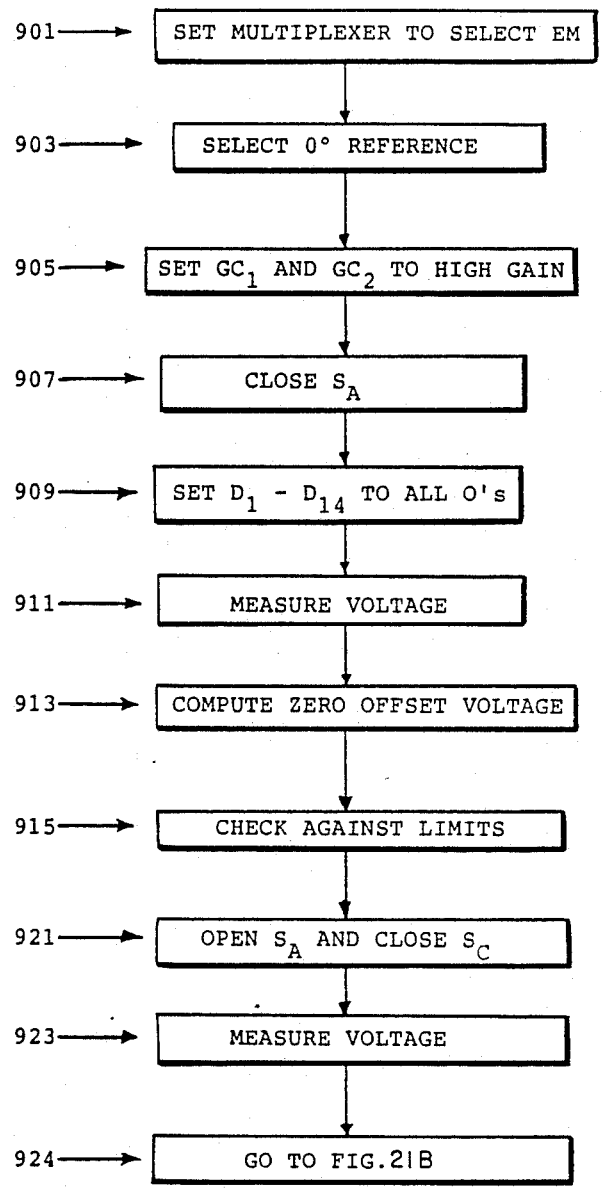
Figure 21:
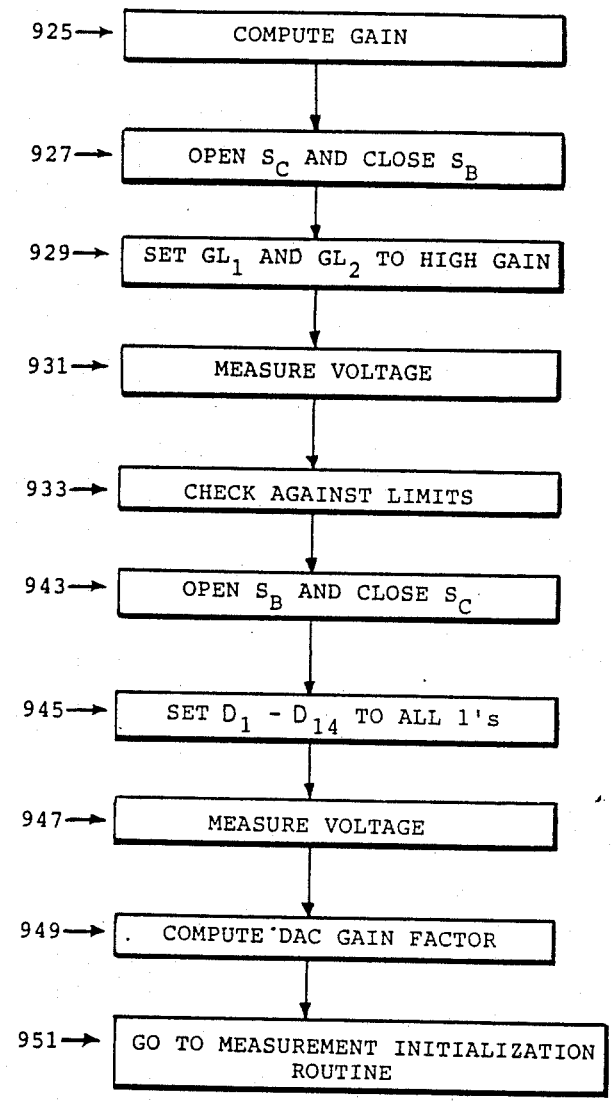
Figure 22A:
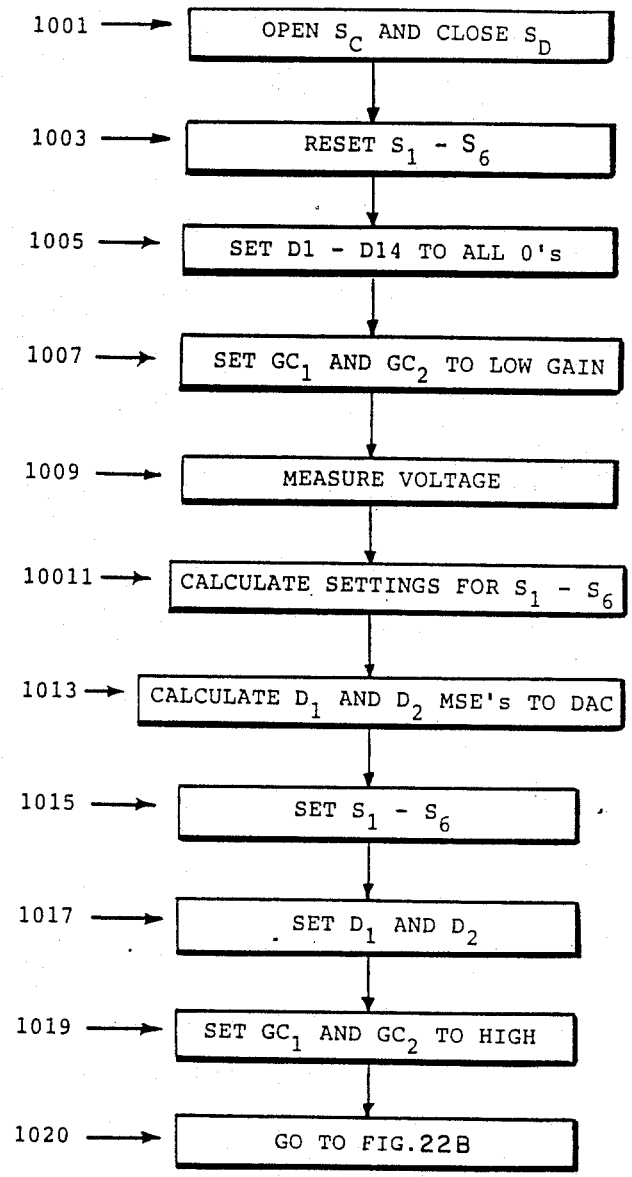
Figure 22:
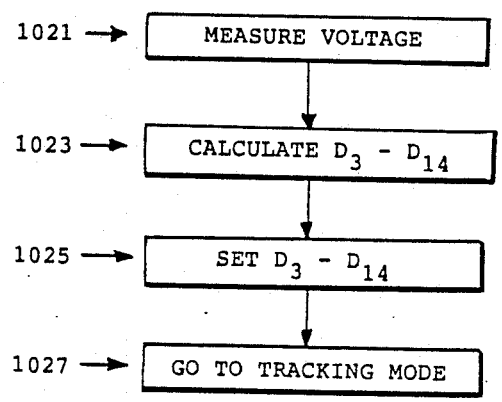
Figure 22C:
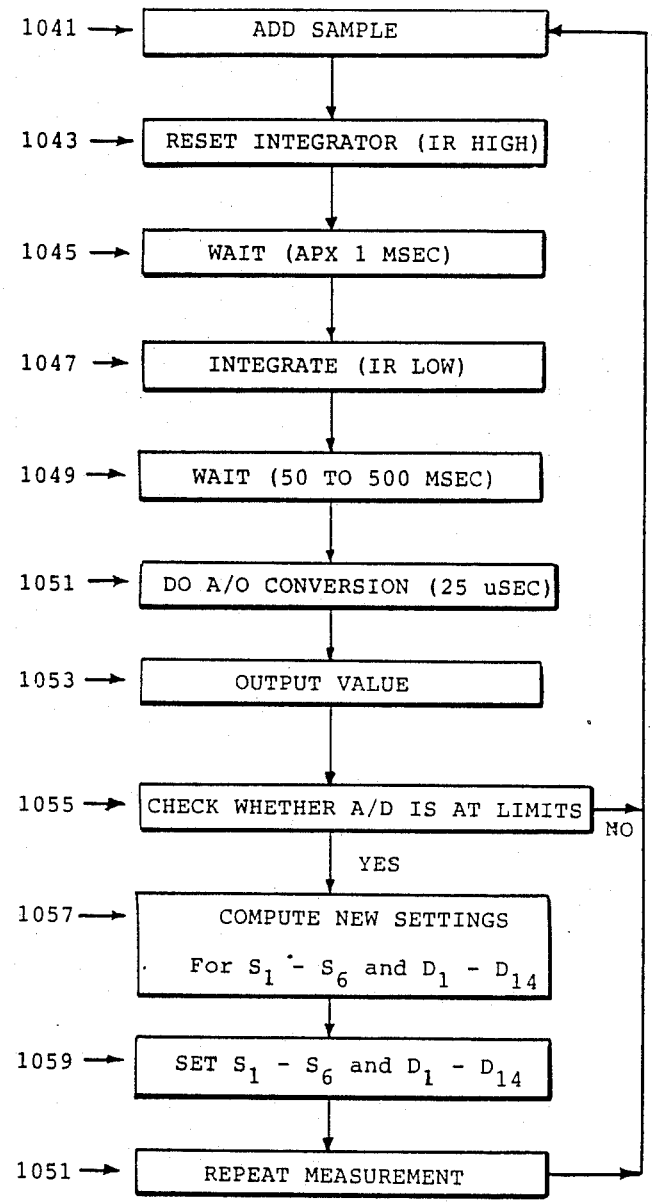

FIGS. 20 through 22 are flow diagrams showing the steps and methods performed by the digital processor controller to carry out a conductivity measurement. It is assumed that to start, the cells and reservoir of the apparatus are filled with electrolyte, that the solution is flowing through the system, and that the material to be analyzed has not yet been added to the electrolyte.

FIG. 20A shows the initial diagnostic routines performed by the instrument prior to making conductivity measurements. First, the processor initializes the machine including setting all switches and, if the flow is under control of the processor, block 801. Switches $S_E$-$S_H$ are all put into their open position. Switch $GC_2$ is set to the high gain position, and the random reference signal is selected by multiplexer 2352 for the initial measurements during which the magnitude of various signals is measured.

Next, the instrument measures the values of $EC_1$ and $EC_2$, and $E_1$ through $E_4$. The digital processor does this by sending signals to multiplexer 2330 which sequentially applies each of these signals to the input of amplifier 2332 and then measuring the voltage, block 803. For each signal, the processor checks to ensure that each of these voltages are within predetermined limits, block 805. If not, the processor goes to an error routine, denoted by branch point E, where an appropriate error message is output to the operator and the measurement process is aborted.

FIG. 20B is a brief flow diagram of how voltage measurements are made during the diagnostic routine, such as those performed in block 803. First, multiplexer 2330 is commanded to select the proper signal, block 813. Next, the IR signal is set high to reset the integrator, block 815. The processor waits for at least 1 millisecond to allow the intgrator capacitor to completely discharge. The IR signal is then set low to start the integration of the demodulated signal, block 817. The processor waits for a predetermined time, block 819, and then commands the A/D converter to convert and measure the output voltage from the integrator, block 821.

Returning to FIG. 20A, if the voltages measured during block 805 are within the proper limits, the processor proceeds to determine the current flowing through the cells. This is done by measuring the $EC_0$ voltage at the output of signal generator 2200, block 821. The processor then computes the value of the cell current from the values of $EC_1$, $EC_0$, and the signal generator resistance selected by $S_R$, block 823.

The processor next checks the impedances between terminals $V_1$ and $V_2$. This is begun by closing switches $S_E$ and $S_F$, block 831, which connects the two 1-kilohm resistors 2242 between terminals $V_1$ and $V_2$. Next $E_1$ and $E_2$ are measured, block 833. From the previously computed value of the current and the values of $E_1$ and $E_2$ with and without the resistors 2242 connected, the impedance between terminals $V_1$ and $V_2$ is computed, block 835. This value is then checked against its limit values, block 837.

If the impedance is within the limits, switches $S_E$ and $S_F$ are opened, block 839, and the above procedure is repeated to measure the impedance between terminals $V_2$ and $V_3$, blocks 841-849, and between $V_3$ and $V_4$, blocks 851-859.

Next the guard electrode leakage currents are checked, blocks 871-877. First, switches $GL_1$ through $GL_4$ are closed, block 871, and the voltages $E_1$ through $E_4$ are measured with the resistors 510 shown in FIG. 17 in series with the guard electrode. From the change in each of the voltages $E_1$ through $E_4$ with and without resistors 510 in series with the guard electrodes, the leakage current for each of the four lines is computed, block 875, and compared against the limit values, block 877.

If the flow rate is checked, this is done next, blocks 881-887. If necessary, the flow measurement apparatus is enabled by the FE signal, block 881. The flow signals F1 and F2 are then measured, blocks 883-885, and checked against their limit values, block 887.

To end the diagnostic routine, a check is made to ensure that the signals from the cells are properly phased, blocks 891-899. This check ensures that a short or other malfunction has not shifted the phase of one of the signals from terminals $V_1$-$V_4$. The previous measurements of $E_1$-$E_4$ were made with the random reference selected by multiplexer 2352 for the demodulation. First, the processor commands multiplexer 2352 to select the 0-degree reference signal, block 891. The values of $E_1$-$E_4$ are then measured, block 893. The multiplexer is then commanded to select the 90-degree reference, block 895. The values of $E_1$-$E_4$ are measured again, block 897. Finally, the measured values are checked to ensure that signals from terminals $V_1$-$V_4$ are within allowable limits, block 899. If so, the processor proceeds to the calibration routines, block 900.

FIG. 21 shows the calibration routines. First, the zero offset error of DAC 2296 is measured, blocks 901-915. To begin, multiplexer 2330 is commanded to select the EM signal for measurement, block 901, and multiplexer 2352 is commanded to select the 0-degree clock signal as the demodulating signal, block 903. Both gain control signals $GC_1$ and $GC_2$ are set to the high gain state, block 905. Switch $S_A$ is closed to provide a ground reference to one input of comparator 2292, block 907. Next, the digital inputs $D_1$-$D_{14}$ to DAC 2296 are all set to zero, block 909. The differential input voltage to comparator 2292 at this point is the difference between ground and the zero output voltage from DAC 2296. This voltage is measured, block 911, and the zero offset error from DAC 2296 is computed, block 913. This value is checked against its limit values, block 915. If the error is within acceptable limits, the offset error value is stored and used to correct later measurements.

Next, the A/D converter is calibrated to determine the output from the A/D converter which is equivalent to one turn of the secondary windings on transformer 2236. With the gain still at high and the DAC output still at 0, switch $S_A$ is opened and switch $S_C$ is closed to connect the output from the two turn winding 2286 to the measurement circuitry, block 921. The voltage is measured, block 923, and the gain from the input of comparator 2292 through the A/D output is computed, block 925.

Next, the gain reduction factors controlled by $GC_1$ and $GC_2$ are computed. First, switch $S_C$ is opened and Switch $S_B$ is closed, block 927. The input to the comparator is now precisely 32 times larger, due to the precision of the outputs from transformer 2236. The processor then sets the $GC_1$ and $GC_2$ signals to select high gain, block 929. The voltage is measured, block 931, and the ratio between the two gain settings is computed and stored, block 935.

The gain of DAC 2296 and resistive divider 2298-299 is then calibrated. Switch $S_B$ is opened and switch $S_C$ is closed to connect the 2-turn winding 2286 to the comparator, block 943. The processor sets the $D_1$-$D_{14}$ inputs to DAC 2296 all high, block 945. The voltage is then measured, block 947. By comparing this voltage with the voltage measured in block 923, the gain factor of the DAC and the 64:1 resistive divider can be computed, block 949. This completes the calibration routine. The various correction factors determined during the calibration are used to determine the actual voltages from the measured voltages in the measurement routines described below.

FIGS. 22A and 22B show the routine by which the conductivity change is measured. First, an initial routine, shown in FIG. 22B, is performed to quickly set switches $S_1$–$S_6$ and the DAC to their initial values. To do this, switch $S_C$ is opened and switch $S_D$ is closed to measure the voltage from the series connection of windings 2270, 2272, and 2274–2284, block 1001. The $D_1$–$D_{14}$ inputs to the DAC are set to 0, block 1003, and switches $S_1$–$S_6$ are set to deselect all six of the selectable windings of transformer 2236, block 1007.

At this point the signal applied to the measurement circuitry is the difference between the test and control cell voltages. This voltage will typically be a fairly large value due to the differences between the bioregions with and without the antiligands in the matrix, or due to other differences between the symmetry of the two fluid channels. Because of this the gain is set to the low value, block 1007, to prevent saturation of the measurement circuitry. The voltage is then measured, block 1009. From this measurement, as corrected by the factors determined during calibration, the processor computes the proper settings for switches $S_1$–$S_6$ and the two MSB's of DAC 2296, blocks 1011 and 1013.

$S_1$–$S_6$ and the MSB's $D_1$ and $D_2$ are set by the processor, blocks 1015 and 1017. The gain is set to high, block 1019, and the voltage is again measured, block 1021. The processor then computes the value of the 12 LSB's of the DAC, block 1023, and the processor sets DAC lines $D_3$–$D_{14}$ to these values, block 1025. At this point, the difference between the voltages to comparator 2292 should be less than one LSB of the DAC output. The processor then goes to the tracking routine shown in FIG. 22B.

At the beginning of the tracking routine, the fluid sample to be analyzed is added to the electrolyte, block 1041. This may be done under control of the processor or manually in response to a prompt from the processor. Next, the integrator is reset. First, the processor sets the IR signal high to reset the integrator, block 1045. The processor waits for a short period of approximately 1 millisecond to allow the integrator capacitor to fully discharge, block 1045. The processor then sets the IR signal low, block 1947, to begin the integration of the voltage being measured.

The integrator is allowed to integrate for a selected period of time, block 1049, typically 50 to 500 milliseconds. At the end of the integration period, the processor commands the D/A converter to do a conversion, block 1051. The conversion takes aproximately 225 microseconds, which is essentially instantaneously in terms of the rate of change of the integrator output signal. The A/D digital output is stored for later processing, block 1053.

Next, the processor checks to see whether the A/D converter is approaching the limits of its dynamic range, block 1055. If not, the processor returns to block 1043, and the above process is repeated. If the A/D is approaching the limits of its measurement range, the processor computes new settings for switches $S_1$–$S_6$ and/or DAC inputs $D_1$–$D_{14}$ which will return the voltage measured by the A/D converter to the center of its measurement range, block 1057, and these values are sent to the switches and DAC, block 1061. The processor then returns to block 1043 and the above process is repeated.

EXAMPLE 9

Figure 23:
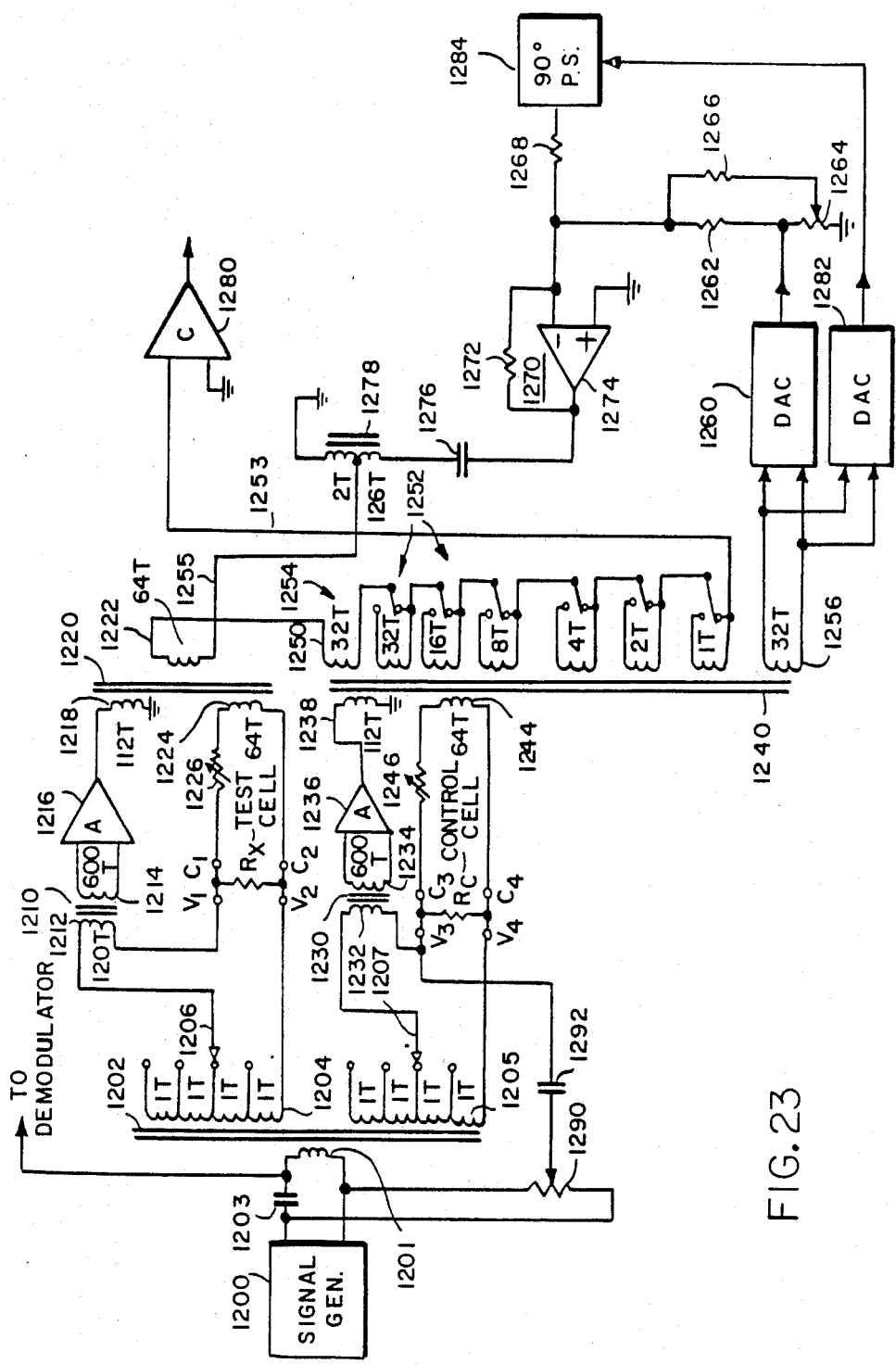
FIG. 23 shows an alternate embodiment for the embodiment shown in FIG. 14.

Another embodiment of the circuitry of an instrument for measuring the relative conductance of a test volume and a control volume is shown in FIG. 23. This circuitry was used in making the measurements in several of the examples set forth in the present patent application, as noted. The circuitry of FIG. 23 is similar in many respects to the circuitry of Example 8, and the explanation below will point out the differences between the circuitry of FIG. 23 and the circuitry already discussed.

The circuitry of FIG. 23 is designed to work with a test and control cell structure in which each cell has its own current path, such as the apparatus of FIG. 5D, which provides individual current electrode pairs for the test cell fluid path and the control cell fluid path. These electrodes are shown schematically in FIG. 5D by electrodes 146 and 148 for the test cell and electrodes 150 and 152 for the control cell. The circuitry of FIG. 23 also works with an apparatus such as that of FIG. 5C, wherein the test and control cells share a common current electrode 144.

In FIG. 23, a signal generator 1200 applies a sine wave signal to an input winding 1201 of a transformer 1202 via a capacitor 1203. In this embodiment, the frequency of signal generator 1200 is 3 kHz. Transformer 1202 has two, identical, output windings 1204 and 1205. Winding 1204 has four output taps, and the output is taken from one of these taps via a 4-pole switch 1206. The primary winding of transformer 1202 has 140 turns on a supermalloy toroidial core, and each of the taps on secondary windings 1204 and 1205 are single turn windings. The two secondary windings provide individual current sources for the test and control cells.

The output from one of the taps on winding 1204, as selected by switch 1206, is applied to one end of the input winding 1212 of a transformer 1210. The other end of winding 1212 is connected to the first voltage measurement terminal $V_1$ of the test cell. The test and control cell resistances are denoted by $R_x$ and $R_c$ respectively. The second voltage terminal $V_2$ of the test cell is connected to the common end of winding 1204.

Transformer 1210 has a 600-turn secondary winding 1214 which drives a high-gain, tuned, AC amplifier 1216. Amplifier 1216 is similar to the AC amplifier shown in FIG. 18, but modified to work at the 3 kHz center frequency. The output of amplifier 1216 drives a 112-turn input winding 1218 to transformer 1220. Transformer 1220 is a precision ratio transformer. A 64-turn feedback winding 1214 is connected in series with a variable resistor 1226 to the two current electrodes $C_1$ and $C_2$. A 64-turn output winding on transformer 1220 provides an output signal.

Transformers 1210 and 1220 and amplifier 1220 are connected to provide a negative feedback loop. Due to the high gain of amplifier 1216 and the negative feedback provided through the transformers, the input to amplifier 1216 can be considered to be a virtual short circuit, and the voltage drop across winding 1212 is essentially zero. Thus the voltage across terminals $V_1$ and $V_2$ is nearly equal to the voltage from transformer winding 1204. The feedback winding 1224 drives a current through resistor 1226 and the test cell resistance $R_x$ to maintain the voltage drop across the voltage terminals $V_1$ and $V_2$ equal to the drive voltage from winding 1204. The current through and the voltage across the test cell is determined by the setting of switch 1206 and value of variable resistor 1226. The value of resistor 1226 is much greater than the test cell impedance to maintain a relatively constant impedance level as the test cell impedance changes. Resistor 1226 is typically on the order of 20–50 kilohms. Resistors 1226 and 1246 are adjusted to obtain a desired signal level from the amplifiers so that the following circuitry does not saturate and to match the amplitudes of the outputs from the test and control cells.

The control cell voltage terminals $V_3$ and $V_4$ and current terminals $C_3$ and $C_4$ are driven by and connected to circuitry identical to the circuitry described above in connection with the test cell, including tapped transformer winding 1205, transformers 1230 and 1240, and amplifier 1236.

Transformers 1220 and 1240 are analagous to transformers 2216 and 2236 shown and described above in reference to FIG. 14. Transformer 1220 has a single 64-turn output winding 1222 which provides a signal representative of the voltage drop across the test cell impedance. Transformer 1240 has a 32-turn winding 1250 and six, binary-weighted windings 1252 having 32, 16, 8, 4, 2, and 1 turns respectively. Six switches 1254 selectively connect windings 1252 in series with a the 64-turn output winding from transformer 1220 and a fixed 32-turn winding 1250 on transformer 1240. These windings allow the control cell output to be scaled over a range of about 0.5 to 1.5 times the test cell output, depending on the setting of switches 1252, with a precision of six bits.

The series connection and phasing of these windings effectively subtracts the control cell output signal, as scaled by the settings of switched 1254, from the test cell output signal. This difference signal is across lines 1253 and 1257 and is applied to comparator circuitry 1280 via an auto-transformer 1278, as explained below. The operation of the circuitry in comparator 1280 is similar to the comparator circuitry shown and described in FIG. 15.

Switches 1254 provide six bits of scaling range. Fourteen additional bits of scaling are provided by a 14-bit multiplying DAC 1260 in a manner similar to that of FIG. 14. DAC 1260 may be implemented by a ICL 7134U unipolar D/A integrated circuit. The output from an independent 32-turn winding 1256 is applied to the input of the DAC 1260. DAC 1260 is controlled by the digital processor, similarly to DAC 2296 in FIG. 14. The output from DAC 1260 is applied via a resistive network including resistors 1262-1268 and a capacitor 1276 to a unity-gain buffer amplifier 1270.

The output from buffer 1270 is applied to one end of the auto-transformer 1278. The other end of auto-transformer 1278 is grounded. The turns ratio of the two sections of the auto-transformer is 128 to 2. This scales the output of the DAC 1260 by a factor of 64 so that one MSB from the DAC is equivalent to the output from a one-half turn winding on transformer 1240. A 10K potentiometer 1269 in conjunction with 2250K resistor 1260 and a 10.2K resistor 1262 all the output from the DAC to be trimmed so that it is exactly equal to one-half turn. Thus switches 1254 and DAC 1260 provide a 20-bit range over which the control cell output can be scaled to track the test cell output.

A second DAC 1282 is also driven by winding 1256. DAC 1282 may be implemented by a ICL 7134B bipolar D/A converter integrated circuit. The output from DAC 1256 is applied via a 90° phase shifter circuit 1284 and a 10K resistor 1268 to buffer amplifier 1270. Thus, the total input to amplifier 1270 is composed of in-phase and quadrature components. During the diagnostic and calibration phases, the digital processor measures the quadrature component in the ouput from the test cell and sets the digital input to DAC 1282 so that the quadrature component is cancelled or reduced to prevent saturation of the following measurement circuitry.

Further quadrature compensation may be optionally added by means of a potentiometer 1290 connected across the output terminals of signal generator 1200 and a capacitor 1292 connecting the wiper of pot 1290 to terminal $V_3$. Typical values for these components are 5 kilohms and 100 pf. The setting of potentiometer 1290 may be adjusted to compensate for small amounts of quadrature error caused by capacitive loading.

The procedures followed in measuring conductivity using the alternate embodiment shown in FIG. 23 are similar to those described above and illustrated in FIGS. 20-22. A source code listing of a program for implementing these procedures with the embodiment of FIG. 23 is attached hereto as Appendix A. This listing is written in Basic and is for controlling a Hewlett-Packard Computer Model 9845 to perform the described measurements.

APPENDIX A

```
10  !  ******* ( 18 OCT 1984 "BS_COR" ( GPIB @ PLOTTING )- *************
20  !
30  !
40  COM Time,A$,T,Bits,Answer$,Stabilise_time,Routine,Ans$,Plot$,Print$,Gain,Bit
s$,I,Av$,Samples,Scale,Scans,Gra$,Hardcopy$,Gain_,Interval,Cycle,B$
50  COM Date_$,Run,Title$,Add_desc1$,Add_desc2$,Biolayer$,Sensor_desc$,U$[25]
60  COM Ratio1,Slope
70  COM SHORT Out2(10000)
80  ON KEY #0 GOSUB Pri
90  ON KEY #1 GOSUB Gra
100 ON KEY #15 GOTO Dump
110 ON KEY #3 GOTO 5900
120 RESET 7
130 PRINTER IS 16
140 Replot$="N"
150 GCLEAR
160 EXIT GRAPHICS
170 IF Cycle=0 THEN GOTO 220
180 PRINT PAGE
190 PRINT "DO YOU WISH TO REPLOT PREVIOUS DATA TO A DIFFERENT SCALE...(Y/N)"
200 INPUT Replot$
```

```
210  IF Replot$="Y" THEN GOSUB Replot
220  PRINT PAGE
230  U$=".....PREVIOUSLY WAS....."
240  PRINT "ENTER SENSOR DESCRIPTION";U$;Sensor_desc$
250  INPUT Sensor_desc$
260  PRINT PAGE
270  PRINT "ENTER BIOLAYER DESCRIPTION";U$;Biolayer$
280  INPUT Biolayer$
290  PRINT PAGE
300  PRINT "ENTER ANY ADDITIONAL DESCRIPTION";U$;Add_desc1$
310  INPUT Add_desc1$
320  PRINT PAGE
330  PRINT "ENTER DATE",Date_$
340  INPUT Date_$
350  PRINT PAGE
360  PRINT "ENTER RUN NUMBER.....PREVIOUS RUN WAS ";Run
370  Run=Run+1
380  PRINT "NEW RUN WILL BE ";Run;" UNLESS ANOTHER IS ENTERED"
390  INPUT Run
400  PRINT PAGE
410  PRINT "ENTER TITLE.....PREVIOUS TITLE WAS.... ";Title$
420  INPUT Title$
430  PRINT PAGE
440  PRINT "DO YOU WISH TO CHANGE ANY KEYBOARD INPUTS.....(Y or N)"
450  INPUT Answer$
460  PRINT PAGE
470  PRINT "DO YOU WANT HARD COPY....(Y/N)"
480  INPUT Hardcopy$
490  PRINT PAGE
500  IF Answer$="N" THEN GOTO Executive
510  PRINT "PRESENT GAIN LEVEL IS ";Gain_;" DO YOU WISH TO CHANGE IT"
520  PRINT "IF NOT PRESS CONT KEY"
530  PRINT "OTHERWISE ENTER DESIRED GAIN LEVEL"
540  PRINT
550  PRINT "ENTER DESIRED GAIN LEVEL"
560  PRINT "Normal gain level is 3 for a stable sensor or where the variations"
570  PRINT "are small.For a situation where the output is varying rapidly"
580  PRINT "use lower gain levels (2 for moderate situations 1 or 0 for"
590  PRINT "more extreme situations"
600  INPUT Gain_
610  PRINT PAGE
620  ! PRINT "ENTER SAMPLING INTERVAL...(Seconds)"
630  ! RINT "Recommended interval is 0.5 Seconds....(DO NOT EXCEED 2 sec)"
640  ! RINT "If you do not want to change it press CONT key."
650  ! INPUT Interval
660  Interval=.5
670  Time=20000*Inte   al
680  Stabilise_time=.5
690  Bits=20
700  PRINT PAGE
710  PRINT "DO YOU WANT ANY DATA AVERAGING.....(Y/N)"
720  INPUT Av$
730  PRINT PAGE
740  IF Av$="N" THEN Samples=1
750  IF Av$="N" THEN GOTO 800
760  PRINT "PRESENT NUMBER OF SAMPLES IS ";Samples;" DO YOU WISH TO CHANGE IT "
770  PRINT "ENTER NUMBER OF SCANS PER AVERAGE"
780  INPUT Samples
790  PRINT PAGE
800  PRINT "SELECT PAIR  A & B OR PAIR C & D...(A=A&B   C=C&D)"
810  INPUT B$
820  IF B$="A" THEN A$="A"
830  IF B$="C" THEN A$="B"
840  GOSUB Unstick
850  OUTPUT 720;"C";A$
860  PRINT PAGE
870  PRINT "DO YOU WANT A GRAPHICAL OUTPUT"
880  INPUT Gra$
890  IF Gra$="Y" THEN GOSUB Plot_data
900  GOTO Executive
910  !
920  !
930  Plot_data:!
```

```
940  PRINT PAGE
950  PRINT "WHAT FULL SCALE SENSITIVITY ON THE GRAPH DO YOU WANT..(ppm)"
960  INPUT Scale
970  PRINT PAGE
980  PRINT "HOW MANY SCANS FULL SCALE DO YOU WANT ON THE TIME AXIS"
990  INPUT Scans
1000 RETURN
1010 !
1020 !
1030 Unstick:!
1040 SET TIMEOUT 7;T/3
1050 ON INT #7 GOSUB Bomb
1060 RETURN
1070 !
1080 !
1090 Init_quad:!
1100 GOSUB Unstick
1110 OUTPUT 720;"R0"
1120 OUTPUT 720;"L";32;",";0
1130 Quad1=Quad2=Qbit=0
1140 RETURN
1150 !
1160 !
1170 Init_ref:!
1180 GOSUB Unstick
1190 OUTPUT 720;"R9"
1200 OUTPUT 720;"L0,0"
1210 OUTPUT 720;"M0"
1220 Data1=Data2=Data3=Bit=0
1230 RETURN
1240 !
1250 !
1260 Set_hi_ref:!
1270 GOSUB Unstick
1280 M=6-Bit
1290 Data1=Data1+2^M
1300 OUTPUT 720;"M";Data1
1310 RETURN
1320 !
1330 !
1340 Set_hi_quad:!
1350 GOSUB Unstick
1360 M=6-Qbit
1370 Quad1=Quad1+2^M
1380 OUTPUT 720;"L";Quad1;",0"
1390 RETURN
1400 !
1410 !
1420 Set_mid_ref:!
1430 GOSUB Unstick
1440 M=12-Bit
1450 Data2=Data2+2^M
1460 OUTPUT 720;"L";Data2;",0"
1470 RETURN
1480 !
1490 !
1500 Set_lo_quad:!
1510 GOSUB Unstick
1520 M=14-Qbit
1530 Quad2=Quad2+2^M
1540 OUTPUT 720;"L";Quad1;",";Quad2
1550 RETURN
1560 !
1570 !
1580 Set_lo_ref:!
1590 GOSUB Unstick
1600 M=20-Bit
1610 Data3=Data3+2^M
1620 OUTPUT 720;"L";Data2;",";Data3
1630 RETURN
1640 !
1650 !
1660 A_to_d:!
1670 SET TIMEOUT 7;T/3
```

```
1680 ON INT #7 GOSUB Bomb
1690 OUTPUT 720;"S";T
1700 SET TIMEOUT 7;T
1710 WAIT T/3
1720 ENTER 720;Y;Z
1730 SYSTEM TIMEOUT OFF
1740 OFF INT #7
1750 Adc=Y-128
1760 RETURN
1770 !
1780 !
1790 Bomb:!
1800 BEEP
1810 SYSTEM TIMEOUT OFF
1820 OFF INT #7
1830 ABORTIO 7
1840 RESET 7
1850 Gerr=Gerr+1
1860 RETURN
1870 !
1880 !
1890 Gain1:!
1900 OUTPUT 720;"G1"
1910 Gain=1
1920 RETURN
1930 !
1940 !
1950 Gain2:!
1960 OUTPUT 720;"G2"
1970 Gain=2
1980 RETURN
1990 !
2000 !
2010 Gain3:!
2020 OUTPUT 720;"G3"
2030 Gain=3
2040 RETURN
2050 !
2060 !
2070 Gain0:!
2080 OUTPUT 720;"G0"
2090 Gain=0
2100 RETURN
2110 !
2120 !
2130 Executive:!
2140 IF Gra$="Y" THEN GOSUB Graph
2150 EXIT GRAPHICS
2160 PRINT PAGE
2170 Ratio2=Cycle=0
2180 PENUP
2190 T=Time/25
2200 DISP "SET GAIN TO LEVEL ";Gain_
2210 ON Gain_+1 GOSUB Gain0,Gain1,Gain2,Gain3
2220 ! WAIT 1000
2230 DISP "INITIALIZE QUADRATURE"
2240 GOSUB Init_quad
2250 ! WAIT 1000
2260 DISP "INITIALIZE REFERENCE"
2270 GOSUB Init_ref
2280 ! WAIT 1000
2290 DISP "DIGITIZE REFERENCE...(PRELIMINARY)"
2300  GOSUB Digitize_ref
2310 DISP "DIGITIZE QUADRATURE....(PRELIMINARY)"
2320 GOSUB Init_quad
2330  GOSUB Quadrature
2340 !
2350 !
2360 Is_quad_ok:!
2370 GOSUB Unstick!
2380 OUTPUT 720;"R0"!
2390 GOSUB A_to_d !                           THIS ROUTINE CHECKS TO SEE THAT
2400 IF ABS(Adc)<126 THEN GOTO 2490!          QUADRATURE HAS BEEN CORRECTLY
```

```
2410 PRINT PAGE !
2420 FOR Z=1 TO 10!
2430 BEEP!
2440 NEXT Z!
2450 DISP "QUADRATURE PROBLEM....QUADRATURE DOES NOT BALANCE"
2460 END
2470 !
2480 !
2490 GOSUB Unstick
2500 OUTPUT 720;"R9"
2510 DISP "INITIALIZE REFERENCE...(PRECALIBRATE)"
2520 ! WAIT 250
2530 GOSUB Init_ref
2540 DISP "DIGITIZE REFERENCE...(PRECALIBRATE)"
2550 GOSUB Digitize_ref
2560 GOSUB Calibrate
2570 DISP "INITIALIZE REFERENCE...(PRE-TRACK)"
2580 GOSUB Init_ref
2590 DISP "DIGITIZE REFERENCE....(PRE-TRACK)"
2600 GOSUB Digitize_ref
2610 IF Gra$="Y" THEN GRAPHICS
2620 Ratio1=(524288+Data1*16384+Data2*256+Data3)/2^20
2630 Delta=ABS(Ratio1-Ratio2)
2640 Ratio2=Ratio1
2650 G=16^(3-Gain)
2660 IF Delta>.0001*_ THEN GOTO 2580
2670 Gerr=0
2680 T=Time/25
2690 K=30000*I/Slope/T/16^(Gain-1)
2700 PRINT PAGE
2710 GOSUB A_to_d
2720 Adc1=Adc
2730 Ratio=(524288+Data1*16384+Data2*256+Data3-Adc*K)/2^20
2740 IF ABS(Ratio-Ratio1)>.01 THEN GOSUB Init_quad
2750 IF ABS(Ratio-Ratio1)>.01 THEN GOSUB Quadrature
2760 IF ABS(Ratio-Ratio1)>.01 THEN Ratio1=Ratio
2770 GOSUB Unstick
2780 OUTPUT 720;"R9"
2790 IF Cycle=0 THEN Aver_ratio=Ratio
2800 IF Cycle=0 THEN Out1=Ratio
2810 Cycle=Cycle+1
2820 DISP Cycle
2830 Aver_ratio=(Samples-1)/Samples*Aver_ratio+Ratio/Samples
2840 Out=INT(10^7*Aver_ratio+.5)/10^7
2850 C=.1*Cycle-INT(.1*Cycle)
2860 IF C=0 THEN GOTO 2880
2870 GOTO 2910
2880 IMAGE "D1=",DD,"|D2=",DDD,"|D3=",DDD,"|Q1=",DD,"|Q2=",DDD,"|Adc=",SDDD,"|Ratio=",D.DDDDDD,"|Ave=",D.DDDDDDD
2890 PRINT USING 2880;Data1,Data2,Data3,Quad1,Quad2,Adc,Ratio,Out
2900 GOSUB Check_quad
2910 Out2(Cycle)=INT((Out-Out1)/Out1*1E7)/10
2920 IF Cycle<10 THEN GOTO 2940
2930 IF Gra$="Y" THEN PLOT Cycle-10,Out2(Cycle)
2940 IF ABS(Adc)>126 THEN GOSUB Init_ref
2950 IF ABS(Adc)>126 THEN GOSUB Digitize_ref
2960 IF Adc>100 THEN GOTO 2990
2970 IF Adc<-100 THEN GOTO 3010
2980 GOTO 2710
2990 Incr=INT(960000/Time)
3000 GOTO 3020
3010 Incr=-INT(960000/Time)
3020 GOSUB Increment_digi
3030 GOTO 2710
3040 !
3050 !
3060 Digitize_ref: !
3070 Bit=Bit+1
3080 IF Bit<7 THEN GOTO 3120
3090 IF Bit<13 THEN GOTO 3140
3100 IF Bit>12 THEN Stage=3
3110 GOTO 3150
3120 Stage=1
```

BALANCED.

```
3130 GOTO 3150
3140 Stage=2
3150 ON Stage GOSUB Set_hi_ref,Set_mid_ref,Set_lo_ref
3160 WAIT Stabilise_time
3170 GOSUB A_to_d
3180 IF Adc<0 THEN GOSUB Bit_off
3190 IF Bit=Bits THEN RETURN
3200 GOTO 3070
3210 !
3220 !
3230 Bit_off:!
3240 ON Stage GOTO Range1,Range2,Range3
3250 !
3260 !
3270 Range1:!
3280 M=6-Bit
3290 Data1=Data1-2^M
3300 OUTPUT 720;"M";" `a1
3310 RETURN
3320 !
3330 !
3340 Range2:!
3350 M=12-Bit
3360 Data2=Data2-2^M
3370 OUTPUT 720;"L";Data2;",0"
3380 RETURN
3390 !
3400 !
3410 Range3:!
3420 M=20-Bit
3430 Data3=Data3-2^M
3440 OUTPUT 720;"L";Data2;",";Data3
3450 RETURN
3460 !
3470 !
3480 Quadrature:!
3490 Qbit=Qbit+1
3500 IF Qbit<7 THEN GOSUB Set_hi_quad
3510 IF Qbit>6 THEN GOSUB Set_lo_quad
3520 WAIT Stabilise_time
3530 GOSUB A_to_d
3540 IF Adc>0 THEN GOSUB Qbit_off
3550 IF Qbit>13 THEN RETURN
3560 GOTO 3490
3570 !
3580 !
3590 Qbit_off:!
3600 IF Qbit<7 THEN GOTO Qbit1
3610 IF Qbit>6 THEN GOTO Qbit2
3620 !
3630 !
3640 Qbit1:!
3650 M=6-Qbit
3660 Quad1=Quad1-2^M
3670 OUTPUT 720;"L";Quad1;",0"
3680 RETURN
3690 !
3700 !
3710 Qbit2:!
3720 M=14-Qbit
3730 Quad2=Quad2-2^M
3740 OUTPUT 720;"L";Quad1;",";Quad2
3750 RETURN
3760 !
3770 !
3780 !
3790 !
3800 Graph:!
3810 PLOTTER IS 13,"GRAPHICS"
3820 GRAPHICS
3830 DEG
3840 MOVE 49*RATIO,1
3850 CSIZE 4
3860 LABEL "SCANS"
```

```
3870 MOVE 2.5*RATIO,50
3880 CSIZE 4
3890 LDIR 90
3900 LABEL "PPM"
3910 A=RATIO*9.5
3920 B=RATIO*97
3930 LOCATE A,B,10,98
3940 SCALE 0,Scans,-Scale,Scale
3950 MOVE 0,0
3960 LINE TYPE 3
3970 DRAW Scans,0
3980 LINE TYPE 1
3990 AXES .2*Scans,.5*Scale,0,-Scale
4000 LDIR 0
4010 LORG 8
4020 CSIZE 3
4030 FOR Y=-Scale TO Scale STEP .5*Scale
4040 MOVE 0,Y
4050 IF Scale<100 THEN LABEL USING "MDD.DX";Y
4060 IF Scale>=100 THEN LABEL USING "MDDDDDDX";Y
4070 NEXT Y
4080 LDIR 0
4090 LORG 6
4100 FOR X=0 TO Scans STEP .2*Scans
4110 MOVE X,-Scale*1.05
4120 LABEL USING "DDDDD";X
4130 NEXT X
4140 RETURN
4150 !
4160 !
4170 !
4180 !
4190 Encode:!
4200 Data=Data1*16384+Data2*256+Data3+Incr
4210 RETURN
4220 !
4230 !
4240 Decode:!
4250 Data1=INT(Data/16384)
4260 Data2=INT((Data-Data1*16384)/256)
4270 Data3=Data-Data1*16384-Data2*256
4280 RETURN
4290 !
4300 !
4310 Set_d_to_a:!
4320 OUTPUT 720;"M";Data1
4330 OUTPUT 720;"L";Data2;",";Data3
4340 RETURN
4350 !
4360 !
4370 Calibrate:!
4380 PRINTER IS 16
4390 PRINT PAGE
4400 PRINT "CALIBRATION DATA"
4410 PRINT "*****************"
4420 PRINT
4430 Calibrate2:!
4440 GOSUB Gain1
4450 I=500
4460 T=I
4470 Acc_zero=0
4480 FOR N=1 TO 10
4490 GOSUB A_to_d
4500 Acc_zero=Acc_zero+Adc
4510 Zero(N)=Adc
4520 IF ABS(Zero(N)-Acc_zero/N)>5 THEN Error_flag=1
4530 NEXT N
4540 IF ABS(Acc_zero)>20 THEN GOTO Try_again
4550 PRINT "Mean Zero=";Acc_zero/10;"         !(Average of 10 samples)"
4560 Incr=30000
4570 GOSUB Encode
4580 GOSUB Decode
4590 GOSUB Set_d_to_a
1600 Acc=0
```

```
4610 FOR N=1 TO 10
4620 GOSUB A_to_d
4630 Acc=Acc+Adc
4640 Accum(N)=Adc
4650 IF ABS(Accum(N)-Acc/N)>5 THEN Error_flag=1
4660 NEXT N
4670 Slope=(Acc-Acc_zero)/10
4680 PRINT "Mean Accum=";Acc/10;"            (Average of 10 samples)"
4690 PRINT "Mean Slope Factor=";Slope;"       (Average of 10 samples)"
4700 WAIT 5000
4710 BEEP
4720 IF Error_flag=0 THEN GOTO 4860
4730 PRINT
4740 PRINT "DURING THIS CALIBRATION RUN ABNORMAL VARIATIONS IN VALUES "
4750 PRINT "WERE DETECTED.THE DATA ARE AS FOLLOWS"
4760 PRINT
4770 PRINT "SAMPLE","ZERO VALUE","FULLSCALE VALUE","SLOPE VALUE"
4780 FOR N=1 TO 10
4790 PRINT N,Zero(N),Accum(N),Accum(N)-Zero(N)
4800 NEXT N
4810 BEEP
4820 PRINT
4830 PRINT "OPERATION SUSPENDED....press CONT KEY if you wish to continue"
4840 PAUSE
4850 PRINT PAGE
4860 ON Gain_+1 GOSUB Gain0,Gain1,Gain2,Gain3
4870 IF Hardcopy$="N" THEN PRINTER IS 16
4880 Incr=-30000
4890 GOSUB Encode
4900 GOSUB Decode
4910 GOSUB Set_d_to_a
4920 BEEP
4930 IF Hardcopy$="N" THEN PRINTER IS 16
4940 RETURN
4950 !
4960 !
4970 Increment_digi:!
4980 GOSUB Encode
4990 GOSUB Decode
5000 GOSUB Set_d_to_a
5010 RETURN
5020 !
5030 !
5040 Pri:!
5050 EXIT GRAPHICS
5060 RETURN
5070 !
5080 !
5090 Gra:!
5100 GRAPHICS
5110 RETURN
5120 !
5130 !
5140 Dump:!
5150 PRINTER IS 16
5160 PRINT PAGE
5170 Add_desc2$=" "
5180 PRINT "ANY ADDITIONAL DESCRIPTION"
5190 INPUT Add_desc2$
5200 PRINTER IS 0
5210 PRINT PAGE
5220 PRINT TAB(25),Title$
5230 DUMP GRAPHICS
5240 PRINT "SENSOR DESCRIPTION:        ";Sensor_desc$
5250 PRINT "BIOLAYER:                  ";Biolayer$
5260 PRINT "DATE:                      ";Date_$
5270 PRINT "RUN NUMBER:                ";Run
5280 PRINT "INITIAL RESISTANCE RATIO:  ";INT(1E6*Rati +.5)/1E6
5290 PRINT "SAMPLES PER SCAN:          ";Samples
5300 PRINT "GAIN LEVEL                 ";Gain_
5310 PRINT "MEAN SLOPE FACTOR:         ";Slope
```

```
5320 PRINT "COMMENTS:"
5330 PRINT Add_desc1$
5340 PRINT Add_desc2$
5350 PRINT
5360 GOTO 10
5370 !
5380 !
5390 Replot:!
5400 GOSUB Plot_data
5410 Base_line=100
5420 Out3=0
5430 PRINT "DO YOU WANT BASE LINE DRIFT CORRECTIONS....(Y=Yes  N=No)"
5440 INPUT Ans$
5450 IF Ans$="Y" THEN GOTO 5480
5460 Drift_per_scan=0
5470 GOTO 5660
5480 PRINT "ENTER No OF SCANS FOR START OF BASE-LINE DRIFT CORRECTION"
5490 PRINT "    (Default value=0 scans)"
5500 INPUT Begin
5510 PRINT
5520 PRINT
5530 PRINT "ENTER No OF SCANS FOR END OF BASE-LINE  DRIFT CORRECTION"
5540 PRINT "   ( Default value=100 scans)"
5550 INPUT End
5560 FOR N=Begin+1 TO .2*(End-Begin)+Begin
5570 Out3=Out3+Out2(N)
5580 NEXT N
5590 Out4=Out3*5/(End-Begin)
5600 Out3=0
5610 FOR N=Begin+1+.8*(End-Begin) TO End
5620 Out3=Out3+Out2(N)
5630 NEXT N
5640 Out5=Out3*5/(End-Begin)
5650 Drift_per_scan=(Out5-Out4)/.8/(End-Begin)
5660 IF Scans>Cycle THEN Scans=Cycle
5670 GOSUB Graph
5680 FOR N=1 TO Scans
5690 PLOT N,Out2(N)-Out2(Begin)-(N-Begin)*Drift_per_scan
5700 NEXT N
5710 GOTO 5710
5720 !
5730 !
5740 Check_quad:!
5750 GOSUB Unstick
5760 OUTPUT 720;"R0"
5770 GOSUB A_to_d
5780 IF ABS(Adc)<126 THEN GOTO 5810
5790 GOSUB Init_quad
5800 GOSUB Quadrature
5810 OUTPUT 720;"R9"
5820 RETURN
5830 !
5840 !
5850 Try_again:!
5860 DISP "RETRYING TO BALANCE QUADRATURE"
5870 FOR Z=1 TO 100
5880 BEEP
5890 NEXT Z
5900 GOSUB Init_quad
5910 GOSUB Quadrature
5920 GOSUB Init_ref
5930 GOSUB Digitize_ref
5940 GOTO Calibrate
5950 !
5960 !
5970 !
5980 !
5990 Sar:!
6000 DISP "INIT-QUAD"
6010 GOSUB Init_quad
6020 DISP "INIT-REF"
6030 GOSUB Init_ref
6040 Bits=20
6050 DISP "DIGITIZE REF"
```

```
6060 GOSUB Digitize_ref
6070 DISP "INIT QUAD    .....(LINE 6025)"
6080 GOSUB Init_quad
6090 DISP "QUADRATURE"
6100 GOSUB Quadrature
6110 DISP "INIT REF   (LINE 6035)"
6120 GOSUB Init_ref
6130 DISP "DIGITIZE REF  (LINE 6038)"
6140 GOSUB Digitize_ref
6150  Ratio=(524288+Data1*16384+Data2*256+Data3)/2^20
6160 PRINT "D1=";Data1,"D2=";Data2,"D3=";Data3,"Ratio=";INT(1E6*Ratio+.5)/1E6
6170 GOTO 6110
6180 !
6190 !
6200 Adj_msb_lsb:!
6210 INPUT "ENTER DESIRED GAIN",G
6220 ON G GOSUB Gain1,Gain2,Gain3
6230 GOSUB Init_ref
6240 GOSUB Digitize_ref
6250 GOSUB Init_quad
6260 GOSUB Quadrature
6270 GOSUB Init_ref
6280 GOSUB Low_data
6290 GOSUB Dig
6300 Adc_low=Adc
6310 GOSUB High_data
6320 GOSUB Dig
6330 Adc_high=Adc
6340 PRINT "LO=";Adc_low,"HI=";Adc_high
6350 GOTO 6280
6360 !
6370 !
6380 Low_data:!
6390 Data1=31
6400 Data2=63
6410 Data3=255
6420 RETURN
6430 !
6440 !
6450 High_data:!
6460 Data1=32
6470 Data2=0
6480 Data3=0
6490 RETURN
6500 !
6510 !
6520 Dig:!
6530 GOSUB Set_d_to_a
6540 GOSUB A_to_d
6550 RETURN
```

What is claimed is:

1. A method for determining the presence of a ligand in a fluid sample comprising:
   (a) localizing antiligand which interacts with said ligand in at least one predetermined region, said predetermined region being at least partially contained within a test volume;
   (b) exposing said predetermined region to said fluid sample; and
   (c) measuring the bulk conductance of said test volume to determine the occurrence of ligand-antiligand interaction in said predetermined region by detecting changes in the bulk conductance of said test volume due to ligand-antiligand interaction in said predetermined region.

2. The method of claim 1, wherein said localization of said antiligand in said predetermined region comprises confining said antiligand within the boundaries of a membrane, said membrane being permeable at least to said ligand.

3. The method of claim 1, wherein said ligand is selected from the group consisting of antigens, cell surface antigens, antigenic determinants, haptens, antibodies, antibody fragments, monovalent antibody fragments, nucleic acid sequences, enzymes, cofactors, enzyme substrates, genetically or chemically altered proteins, receptor protein, permeases, other transport proteins, binding proteins, molecules bound by a permease, transport protein or binding protein, carbohydrates, lectins, metal ions, metal-binding proteins, and other metal-binding substances.

4. The method of claim 1, wherein said antiligand has high affinity for said ligand.

5. The method of claim 1, wherein said antiligand has low affinity for said ligand.

6. The method of claim 1, including the step of forming a complex between an antiligand specific for said ligand to be determined and an amplifying substance.

7. The method of claim 6, wherein said complex is preformed and said ligand in said fluid sample binds to said antiligand component of said complex and further binds to said antiligand in said predetermined region.

8. The method of claim 1, wherein the bulk conductance of said test volume is measured with electrodes which are in contact with an electrolyte.

9. The method of claim 8, wherein four electrodes are used to measure the bulk conductance of said test volume, two of said electrodes providing a current through said test volume whose bulk conductance is being measured and two of said electrodes measuring the voltage drop across said test volume.

10. The method of claim 9, wherein said voltage electrodes are recessed from said current.

11. The method of claim 9, wherein said current electrodes are recessed from said test volume.

12. The method of claim 1, wherein said localization of said antiligand in said predetermined region comprises immobilizing said antiligand on a matrix.

13. The method of claim 12, wherein said matrix is selected from the group consisting of gel beads, gel layers, glass beads, polymeric beads, microporous membranes, porous paper, and mixtures thereof.

14. The method of claim 12, wherein said matrix is contacted with a flowing stream of said fluid sample.

15. The method of claim 14, wherein said contacting comprises causing said fluid sample to flow through said matrix.

16. The method of claim 14, wherein said contacting comprises causing said fluid sample to flow past said matrix.

17. The method of claim 1, wherein said changes in bulk conductance are determined by comparing the bulk conductance of said test volume with the bulk conductance of at least one control volume.

18. The method of claim 17, wherein said control volume does not contain any localized substance therein.

19. The method of claim 17, wherein said fluid sample contains a known concentration of a control ligand, and control antiligand which interacts with said control ligand is localized in at least one predetermined region of said control volume.

20. The method of claim 17, wherein said control volume does not contain antiligand which reacts with said ligand.

21. The method of claim 20, wherein said control volume is substantially free of specific interactions which effect changes in bulk conductance.

22. The method of claim 21, said control volume at least partially containing therein at least one predetermined region, said predetermined region being exposed to said fluid sample and also having localized therein molecules whose physical properties are similar to the physical properties of said antiligand.

23. The method of claim 21, wherein at least one of (a) the bulk conductance of said test volume, and (b) the bulk conductance of a second control volume is further compared with the bulk conductance of said control volume, and wherein said fluid sample contains a known concentration of a control ligand, and control antiligand which interacts with said control ligand is localized in at least one predetermined region of said second control volume.

24. The method claim 1, including the step of forming a complex between a ligand which interacts with said antiligand and an amplifying substance.

25. The method of claim 24, wherein said complex is preformed and added to said fluid sample, said ligand component of said complex being present in a known amount.

26. The method of claim 24, wherein said complex is preformed and prebound to said antiligand in said predetermined region.

27. The method of claim 24, wherein said complex is preformed and compartmentalized in at least one region which is adjacent said predetermined region containing said localized antiligand, said compartment being at least partially within said test volume.

28. The method of claim 24, wherein said complex is formed in said fluid sample, said ligand component of said complex being derived from the ligand present in said fluid sample.

29. The method of claim 28, including the step of adding a known amount of ligand which interacts with said antiligand to said fluid sample containing said complex therein.

30. The method of claim 24, wherein said amplifying substance is a particle selected from the group consisting of antiligand which interacts with said ligand, antiligand which interacts with said ligand bound to a second amplifying substance, macromolecules, cells, small molecules, molecular complexes, latex beads, lipid vesicles, non-conducting polymer beads, other non-conducting particles, magnetic particles, and mixtures thereof.

31. The method of claim 30, wherein said particle is antiligand which interacts with said ligand bound to said second amplifying substance.

32. The method of claim 31, wherein said second amplifying substance can be further reacted to effect a change in the bulk conductance of said test volume.

33. The method of claim 32, wherein said further reaction comprises generation of a gas.

34. A method for determining the presence of a ligand in a fluid sample comprising:
(a) localizing ligand in at least one predetermined region, said predetermined region being at least partially contained within a test volume;
(b) exposing said predetermined region to said fluid sample and to an antiligand which interacts both with said ligand in said fluid sample and said localized ligand; and
(c) measuring the bulk conductance of said test volume to determine the occurrence of ligand-antiligand interaction by detecting changes in the bulk conductance of said test volume.

35. The method of claim 34, wherein said changes in bulk conductance are determined by comparing the bulk conductance of said test volume with the bulk conductance of at least one control volume.

36. The method of claim 34, wherein said localization of said localized ligand comprises confining said ligand within the boudaries of a membrane, said membrane being permeable to at least said antiligand and said ligand present in said fluid sample.

37. The method of claim 34, including the step of forming a complex between antiligand which interacts with said ligand and an amplifying substance.

38. The method of claim 34, including the step of forming a complex between a ligand which interacts with said antiligand and an amplifying substance.

39. The method of claim 34, wherein localization of said localized ligand comprises immobilization on a matrix.

40. The method of claim 39, wherein said matrix is contacted with a flowing stream of said fluid sample.

41. A method for determining the presence of a ligand in a fluid sample comprising:
(a) localizing antiligand which interacts with said ligand in at least one predetermined region, said predetermined region being separate from a test volume;
(b) exposing said predetermined region to said fluid sample; and
(c) measuring the bulk conductance of said test volume to determine the occurrence of ligand-antiligand interaction in said predetermined region by detecting changes in the bulk conductance of said test volume due to ligand-antiligand interaction in said predetermined region.

42. The method of claim 11, including the step of forming a complex between a ligand which interacts with said antiligand and an amplifying substance.

43. The method of claim 42, wherein said complex is preformed and compartmentalized in at least one region which is adjacent said predetermined region containing said localized antiligand, said compartment being at least partially within said test volume.

44. A sensor for determining the presence of a ligand in a fluid sample, said sensor comprising:
(a) means for localizing (i) antiligand which interacts with said ligand or (ii) ligand which interacts with an antiligand, which antiligand also interacts with said ligand in said fluid sample, said localizing means selected from the group consisting of (a) a semipermeable membrane which is permeable at least to said ligand or (b) a matrix material selected from the group consisting of gel beads, gel layers, glass beads, polymeric beads, microporous membranes, porous paper, and mixtures thereof; and
(b) means for measuring the bulk conductance of a test volume which at least partially includes said localizing means.

45. An apparatus for determining the presence of a ligand in a fluid sample, said apparatus comprising:
(a) in at least one predetermined region of said apparatus, means for localizing (i) antiligand which interacts with said ligand or (ii) ligand which interacts with an antiligand, which antiligand also interacts with said ligand in said fluid sample, said localizing means selected from the group consisting of (a) a semipermeable membrane which is permeable at least to said ligand or (b) a matrix material selected from the group consisting of gel beads, gel layers, glass beads, polymeric beads, microporous membranes, porous paper, and mixtures thereof;
(b) means for contacting said fluid sample with said localizing means; and
(c) means for measuring the bulk conductance of a test volume which at least partially contains said predetermined region.

46. The apparatus of claim 45, wherein said region comprises at least one test region for determining the presence of said ligand and at least one control region to provide a comparative basis for making said measurement.

47. The apparatus of claim 45, wherein said test volume essentially entirely includes said localizing means.

48. The apparatus of claim 45, wherein said contacting means comprise a structure having:
(a) an inlet channel for bringing said fluid sample to said localizing means; and
(b) an outlet channel for removing said fluid sample from said localizing means.

49. The apparatus of claim 48, wherein said structure comprises a non-conductive material.

50. The apparatus of claim 45, wherein said non-conductive material is selected from the group consisting of plastic, ceramic, glass, quartz, and mixtures thereof.

51. The apparatus of claim 48, wherein said structure comprises at least three component parts, said first component part comprising said inlet channel, said second component part comprising said outlet channel, and said third component part comprising said localizing means, said first and second component parts being fastened in a sandwiched fashion about said third component part, said third component part being insertable between said first and second component parts.

52. The apparatus of claim 51, further comprising a fluid bath, wherein at least said inlet and outlet channels are submerged in said fluid bath.

53. The apparatus of claim 45, wherein said means for measuring the bulk conductance comprises a plurality of spaced-apart electrodes.

54. The apparatus of claim 53, wherein said apparatus additionally includes a current-modulating material adjacent to said localizing means.

55. The apparatus of claim 53, wherein said localizing means additionally comprises a current modulating material.

56. The apparatus of claim 53, wherein said plurality of electrodes are in contact with an electrolyte.

57. The apparatus of claim 56, wherein said plurality of electrodes comprises two electrodes.

58. The apparatus of claim 57, wherein said plurality of electrodes includes auxiliary electrodes.

59. The apparatus of claim 58, wherein said auxiliary electrodes comprise guard electrodes.

60. The apparatus of claim 56, wherein said plurality of electrodes comprises at least four electrodes.

61. The apparatus of claim 60, wherein two of said electrodes provide a current through said test volume and two measure the drop in voltage across said test volume.

62. The apparatus of claim 61, wherein said plurality of electrodes also includes auxiliary electrodes.

63. The apparatus of claim 62, wherein said auxiliary electrodes comprise guard electrodes.

64. The apparatus of claim 61, wherein each of said current electrodes and each of said voltage electrodes is placed on opposite sides of said localizing means.

65. The apparatus of claim 64, wherein said localizing means essentially entirely includes said test volume.

66. The apparatus of claim 61, wherein said current electrodes are recessed from said test volume.

67. The apparatus of claim 66, wherein said recession comprises placing said current electrodes in chambers, said chambers being in electrical contact with said test volume via conducting channels.

68. The apparatus of claim 67, wherein said conducting channels additionally contain a matrix which retards bubble formation and convection.

69. The apparatus of claim 61, wherein said current electrodes and said voltage electrodes are on the same side of said localizing means.

70. The apparatus of claim 69, wherein said current electrodes and said voltage electrodes lie in the same plane.

71. The apparatus of claim 70, wherein said voltage electrodes are recessed from said current flow.

72. The apparatus of claim 70, wherein said current electrodes are recessed from said test volume.

73. The apparatus of claim 70, wherein said apparatus additionally includes a current-modulating material adjacent to said localizing means.

74. The apparatus of claim 61, wherein said voltage electrodes are recessed from current flow.

75. The apparatus of claim 74, wherein said recession comprises placing said voltage electrodes in chambers, said chambers being in electrical contact with said test volume via conducting channels.

76. The apparatus of claim 75, wherein the width of the opening of said conducting channels adjacent to said test volume ranges from about 25 um to 100 um, and said openings are from about 40 um to 200 um apart with respect to each other.

77. The apparatus of claim 75, wherein said conducting channels additionally contain a matrix which retards bubble formation and convection.

78. The apparatus of claim 77, wherein said localizing means also comprises said matrix contained in said conducting channels.

79. The apparatus of claim 75, wherein the width of the opening of said conducting channels ranges from about 10 um to about 1 mm, and said openings are from about 10 um to about 1 mm apart with respect to each other.

80. The apparatus of claim 79, wherein said test volume ranges up to about 1 ul.

81. The apparatus of claim 79, wherein said test volume is less than about 0.1 ul.

82. The apparatus of claim 79, wherein the thickness of said test volume ranges up to about 1 mm.

83. The apparatus of claim 79, wherein the thickness of said test volume is less than about 0.1 mm.

84. The apparatus of claim 79, wherein the volume of said predetermined region is less than about 0.1 ul.

85. The apparatus of claim 79, wherein the thickness of said predetermined region is less than about 0.1 mm.

* * * * *